(12) United States Patent
Barbas, III et al.

(10) Patent No.: US 7,741,110 B2
(45) Date of Patent: *Jun. 22, 2010

(54) REGULATION OF GENE EXPRESSION USING SINGLE-CHAIN, MONOMERIC, LIGAND DEPENDENT POLYPEPTIDE SWITCHES

(75) Inventors: Carlos F. Barbas, III, Solana Beach, CA (US); Roger Beerli, Adlikon (CH); Ulrich Schopfer, Loerrach (DE)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/280,456

(22) Filed: Nov. 15, 2005

(65) Prior Publication Data

US 2006/0178502 A1 Aug. 10, 2006

Related U.S. Application Data

(63) Continuation of application No. 09/908,153, filed on Jul. 18, 2001, now Pat. No. 7,011,972.

(60) Provisional application No. 60/325,747, filed on Jul. 18, 2000, now abandoned.

(51) Int. Cl.
 *C12N 15/12* (2006.01)
 *C12N 15/62* (2006.01)
 *C12N 15/63* (2006.01)
 *C12N 5/10* (2006.01)
 *C07K 14/435* (2006.01)

(52) U.S. Cl. ............ 435/320.1; 435/325; 530/350; 536/23.4; 536/23.5

(58) Field of Classification Search ............ None
See application file for complete search history.

(56) References Cited

U.S. PATENT DOCUMENTS

| 5,599,904 A | 2/1997 | Evans et al. |
| 5,874,534 A | 2/1999 | Vegeto et al. |
| 7,011,972 B2 | 3/2006 | Barbas et al. |

FOREIGN PATENT DOCUMENTS

| AU | 2005234684 | 12/2005 |
| CA | 2388524 | 5/2001 |
| EP | 0540065 A1 | 5/1993 |
| WO | WO-89/05355 A1 | 6/1989 |
| WO | WO 95/19431 | 7/1995 |
| WO | WO-98/18925 A2 | 5/1998 |
| WO | WO 98/54311 | 12/1998 |
| WO | WO-99/10510 A2 | 3/1999 |
| WO | WO-99/45132 A1 | 9/1999 |
| WO | WO-99/47656 A2 | 9/1999 |
| WO | WO-00/23464 A2 | 4/2000 |
| WO | WO-01/30843 A1 | 5/2001 |
| WO | WO 01/36447 | 5/2001 |
| WO | WO-0206463 A2 | 1/2002 |

OTHER PUBLICATIONS

Bowie et al. (1989) Science 247: 1306-1310.*
Takayama et al. (2001) Experimental Hematology 29: 864-872.*
Evans, R.M., "The Steroid and Thyroid Hormone Receptor Superfamily," Science 240: 889-895 (1988).
Beato, M., "Gene Regulation by Steroid Hormones," Cell 56: 335-344 (1989).
Eilers, M. et al., "Chimaeras of Myc Oncoprotein and Steroid Receptors Cause Hormone-Dependent Transformation of Cells," Nature 340: 66-68 (1989).
Carson-Jurica, M.A. et al., "Steroid Receptor Family: Structure and Functions," Endocrine Rev. 11: 201-220 (1990).
Labow, M.A. et al., "Conversion of the lac Repressor into an Allosterically Regulated Transcriptional Activator for Mammalian Cells," Mol. Cell. Biol. 10: 3343-3356 (1990).
Baim, S.et al., "A Chimeric Mammalian Transactivator Based on the lac Repressor that is Regulated by..." Proc. Natl. Acad. Sci. USA 88: 5072-5076 (1991).
Superti-Furga et al., "Hormone-Dependent Transcriptional Regulation and Cellular Transformation by Fos-Steroid Receptor..." Proc. Natl. Acad. Sci. USA 88: 5114-5118 (1991).
Vegeto et al., "The Mechanism of RU486 Antagonism is Dependent on the Conformation of the Carboxy-Terminal Tail of the Human Progesterone..." Cell 69: 703-713 (1992).
Gossen, M. & Bujard, H., "Tight Control of Gene Expression in Mammalian Cells by Tetracycline-Responsive Promoters," Proc. Natl. Acad.Sci. USA 89: 5547-5551 (1992).
Christopherson, K.S. et al., "Ecdysteroid-Dependent Regulation of Genes in Mammalian Cells by a Drosophila Ecdysone..." Proc. Natl. Acad. Sci. USA 89: 6314-6318 (1992).
Louvion, J.F. et al., "Fusion of GAL4-VP16 to a Steroid-Binding Domain Provides a Tool for Gratuitous Induction of Galactose-Responsive Genes..." Gene 131: 129-134 (1993).
Braselmann, S. et al., "A Selective Transcriptional Induction System for Mammalian Cells Based on Gal4-Estrogen Receptor..." Proc. Natl. Acad. Sci. USA 90: 1657-1661 (1993).
Samuels, M.L. et al., "Conditional Transformation of Cells and Rapid Activation of the Mitogen-Activated Protein Kinase Cascad..." Mol. Cell. Biol. 13: 6241-6252 (1993).
Wang, Y. et al., "A Regulatory System for Use in Gene Transfer," Proc. Natl. Acad. Sci. USA 91: 8180-8184 (1994).
Gossen, M. et al., "Transcriptional Activation by Tetracyclines in Mammalian Cells," Science 268: 1766-1769 (1995).
Littlewood, T.D. et al., "A Modified Oestrogen Receptor Ligand-Binding Domain as an Improved Switch for the Regulation..." Nucl. Acids Res. 23: 1686-1690 (1995).

(Continued)

*Primary Examiner*—Michael Pak
(74) *Attorney, Agent, or Firm*—Schwegman, Lundberg & Woessner, P.A.

(57) ABSTRACT

Single chain, monomeric polypeptide gene switches are provided. The gene switches include ligand binding domains and at least one functional domain. Preferred functional domains are DNA binding domains and transcriptional regulating domains. Methods of regulating gene function using the switches are also provided.

102 Claims, 17 Drawing Sheets

OTHER PUBLICATIONS

No, D. et al., "Ecdysone-Inducible Gene Expression in Mammalian Cells and Transgenic Mice," Proc. Natl. Acad. Sci. USA 93: 3346-3351 (1996).

Rivera, V.M. et al., "A Humanized System for Pharmacologic Control of Gene Expression," Nature Med. 2: 1028-1032 (1996).

Pratt, W.B. & Toft, D. O. "Steroid Receptor Interactions with Heat Shock Protein and Immunophilin Chaperones," Endocrine Rev. 18: 306-360 (1997).

Wang, Y. et al., "Positive and Negative Regulation of Gene Expression in Eukaryotic Cells with an Inducible Transcriptional Regulator," Gene Therapy 4: 432-441 (1997).

Janknecht, R. & Hunter, T. "Convergence of MAP Kinase Pathways on the Ternary Complex Factor Sap-1a," EMBO J. 16: 1620-1627 (1997).

Darnell, J.E. Jr.,"STATs and Gene Regulation," Science 277 1630-1635 (1997).

Beerli, et al., "Toward Controlling Gene Expression at Will: Specific Regulation of the erbB-2/HER-2 Promoter . . ." Proc. Natl. Acad. Sci. USA 95: 14628-14633 (1998).

Segal et al., "Toward Controlling Gene Expression at Will: Selection and Design of Zinc Finger Domains Recognizing . . . " Proc. Natl. Acad. Sci. USA 96: 2758-2763 (1999).

Beerli et al., "Positive and Negative Regulation of Endogenous Genes by Designed Transcription Factors," Proc. Natl. Acad. Sci. USA 97: 1495-1500 (2000).

Lee et al., "Three-Dimensional Solution Structure of a Single Zinc Finger DNA-Binding Domain," Science 245: 635-637 (1989).

Pavletich & Pabo, "Zinc Finger-DNA Recognition: Crystal Structure of a Zif268-DNA Complex at 2.1 Å," Science 252: 809-817 (1991).

Elrod-Erickson, M. et al., "Zif268 Protein-DNA Complex Refined at 1.6 Å: A Model System for Understanding Zinc Finger-DNA Interactions," Structure 4: 1171-1180 (1996).

Swirnoff, A.H. & Milbrandt, J. "DNA-Binding Specificity of NGFI-A and Related Zinc Finger Transcription Factors," Mol. Cell. Biol. 15: 2275-2287 (1995).

Liu et al., "Design of Polydactyl Zinc-Finger Proteins for Unique Addressing within Complex Genomes," Proc. Natl. Acad. Sci. USA 94: 5525-5530 (1997).

Margolin, J.F. et al., "Krüppel-Associated Boxes Are Potent Transcriptional Repression Domains," Proc. Natl. Acad. Sci. USA 91: 4509-4513 (1994).

Ayer, D.E. et al., "Mad Proteins Contain a Dominant Transcription Repression Domain," Mol. Cell. Biol. 16: 5772-5781 (1996).

Desjarlais, J.R & Berg, J.M. "Use of a Zinc-Finger Consensus Sequence Framework and Specificity Rules to Design . . . " Proc. Natl. Acad. Sci. USA 90: 2256-2260 (1993).

Kim, J. & Pabo, C.O., "Transcriptional Repression by Zinc Finger Peptides: Exploring the Potential for Applications in Gene Therapy," J. Biol. Chem. 272: 29795-29800 (1997).

Wu, H. et al., "Building Zinc Fingers by Selection: Toward a Therapeutic Application," Proc. Natl. Acad. Sci. USA 92: 344-348 (1995).

Aumais, J.P. et al., "Function of Directly Repeated Half-Sites as Response Elements for Steroid Hormone Receptors," J. Biol. Chem. 271: 12568-12577 (1996).

Sadowski, I. et al., "GAL4-VP16 Is an Unusually Potent Transcriptional Activator," Nature 335: 563-564(1988).

Yamamoto, T. et al., "Similarity of Protein Encoded by the Human c-erb-B-2 Gene to Epidermal Growth Factor Receptor," Nature 319: 230-234 (1986).

Yao et al., "Functional Ecdysone Receptor is the Product of EcR and Ultraspiracle Genes," Nature 366: 476-479 (1993).

Nakanishi, K. "Past and Present Studies with Ponasterones, the First Insect Molting Hormones from Plants," Steroids 57: 649-657 (1992).

M.L. Whitelaw et al., "Definition of a Novel Ligand Binding Domain of a Nuclear bHLH Receptor: Co-Localization of,Ligand . . . " EMBO J. 12: 4169-4179 (1993).

M.L. Whitelaw et al., "Identification of Transactivation and Repression Functions of the Dioxin Receptor . . . " Mol. Cell. Biol. 14: 8343-8355 (1994).

"U.S. Appl. No. 09/908,153, Notice of Allowance mailed Mar. 29, 2005", 10 pgs.

"U.S. Appl. No. 09/908,153, Response filed Aug. 10, 2004 to Restriction Requirement mailed Jun. 29, 2004", 8 pgs.

"U.S. Appl. No. 09/908,153, Restriction Requirement mailed Jun. 29, 2004", 7 pgs.

"Canadian Application Serial No. 2,415,726, Request for Examination and Voluntary Amendment filed Jul. 10, 2006", 25 pgs.

"European Application Serial No. 01951681.4, Communication mailed Jan. 19, 2004", 5 pgs.

"European Application Serial No. 01951681.4, Communication mailed Jan. 25, 2006", 3 pgs.

"European Application Serial No. 01951681.4, Communication mailed Oct. 16, 2006", 2 pgs.

"European Application Serial No. 01951681.4, Communication under Rule 51(4) mailed Feb. 16, 2007", 6 pgs.

"European Application Serial No. 01951681.4, Invitation pursuant to Article 96(2) and Rule 51(2) EPC mailed Feb. 1, 2005", 2 pgs.

"European Application Serial No. 01951681.4, Response filed May 25, 2005 to Communication mailed Jan. 19, 2004", 9 pgs.

"European Application Serial No. 01951681.4, Response filed Jun. 23, 2006 to Communication mailed Jan. 25, 2006", 7 pgs.

"European Application Serial No. 01951681.4, Response filed Jun. 26, 2007 to Communication under Rule 51(4) mailed Feb. 16, 2007", 10 pgs.

"European Application Serial No. 01951681.4, Response filed Aug. 13, 2004 to Communication mailed Jan. 19, 2004", 27 pgs.

"European Application Serial No. 01951681.4, Response filed Dec. 20, 2006 to Communication mailed Oct. 16, 2006", 16 pgs.

"European Application Serial No. 07019198.6, Communication mailed Feb. 18, 2009", 3 pgs.

"European Application Serial No. 07019198.6, Extended European Search Report mailed May 20, 2008", 9 pgs.

"European Application Serial No. 07019198.6, Response filed Jan. 13, 2009 to Extended European Search Report mailed May 20, 2008", 19 pgs.

"International Application Serial No. PCT/EP01/08190, International Preliminary Examination Report mailed Jun. 7, 2002", 2 pgs.

"International Application Serial No. PCT/EP01/08190, International Search Report mailed Jun. 7, 2002", 4 pgs.

"Israel Application Serial No. 153833, Response filed Sep. 11, 2008 to Office Action mailed May 11, 2008", (w/ English Translation), 11 pgs.

"Israel Application Serial No. 153833, Response filed Oct. 15, 2007 to Office Action mailed May 7, 2007", (w/ English Translation), 11 pgs.

"Japanese Application Serial No. 2002-512356, Final Rejection issued Feb. 24, 2009", (w/ English Translation), 5 pgs.

"Japanese Application Serial No. 2002-512356, Official Action mailed Jun. 3, 2008", (w/ English Translation), 3 pgs.

"Japanese Application Serial No. 2002-512356, Response filed Sep. 3, 2008 to Official Action mailed Jun. 3, 2008", (w/ English Translation of Claims), 14 pgs.

"Ligand Binding Domain", [online]. [retrieved Aug. 9, 2004]. Retrieved from the Internet: <URL: http://www.ks.uiuc.edu/Research/smd_imd/rar_dna/, (modified 2004), 4 pgs.

"Nuclear Hormone Receptors", [online]. [retrieved Aug. 9, 2004]. Retrieved from the Internet: <URL: http://www.ks.uiuc.edu/Research/pro_DNA/ster_horm_rec/, 4 pgs.

Beerli, R. R, et al., "Chemically regulated zinc finger transcription factors", J Biol Chem., 275(42), (2000), 32617-32627.

Brzozowski, A. M., et al., "Molecular basis of agonism in the oestrogen receptor", Nature, 389, (1997), 753-758.

Burcin, M. M., et al., "A Regulatory System for Target Gene Expression", Frontiers in Bioscience, 3, (1998), 1-7.

Carey, M., et al., "An amino-terminal fragment of GAL4 binds DNA as a dimer.", J Mol Biol., 209(3), (Oct. 5, 1989), 423-32.

Chambraud, B., et al., "Several Regions of Human Estrogen Receptor Are Involved in the Formation of Receptor-Heat Shock Protein 90 Complexes", The Journal of Biological Chemistry, 265(33), (1990), 20686-20691.

Elbi, C., et al., "Recruitment of Dioxin Receptor to Active Transcription Sites", Molecular Biology of the Cell, 13, (2001), 2001-2015.

Kato, S., et al., "A new signaling pathway of dioxin receptor ligands through targeted protein degradation", *AATEX*, 14, (2007), 487-494.

Laudet, V., "Evolution of the nuclear receptor superfamily: early diversification from an ancestral orphan receptor", *Journal of Molecular Endocrinology*, 19, (1997), 207-226.

Mendonca, S. D; et al., "Nuclear Hormone Receptors and Evolution", *American Zoologist*, 39(4), (1999), 704-713.

Schoenmakers, E., et al., "Differential DNA binding by the androgen and glucocorticoid receptors involves the second Zn-finger and a C-terminal extension of the DNA-binding domains", *Biochemical Journal*, vol. 31(3), (Aug. 1, 1999), 515-521.

Zhang, Z., et al., "Genomic Analysis of the Nuclear Receptor Family: New Insights Into Structure, Regulation, and Evolution From the Rat Genome", *Genome Research*, 14, (2004), 580-590.

"European Application No.07019198.6, Office Action mailed Jul. 16, 2009", 3 pgs.

"Israeli Application Serial No. 153833, Office Action mailed May 25, 2009", 4 pgs.

"Canada Application Serial No. 2415726, Office Action mailed Aug. 27, 2009", 3 pgs.

\* cited by examiner

B3                              antiparallel β sheet       α helix

F1 (GAC)    AQAALEPKEKPYACPECGKSFSDPGNLVRHQRTHTGEK

F2 (GGG)                 PYKCPECGKSFSRSDKLVRHQRTHTGEK

F3 (GGA)                 PYKCPECGKSFSQSSHLVRHQRTHTGKKTSGQAG

N1                              antiparallel β sheet       α helix

F1 (GTA)    AQAALEPKEKPYACPECGKSFSQSSSLVRHQRTHTGEK

F2 (GAA)                 PYKCPECGKSFSQSSNLVRHQRTHTGEK

F3 (GGG)                 PYKCPECGKSFSRSDKLVRHQRTHTGKKTSGQAG

FIG. 1A

A
B
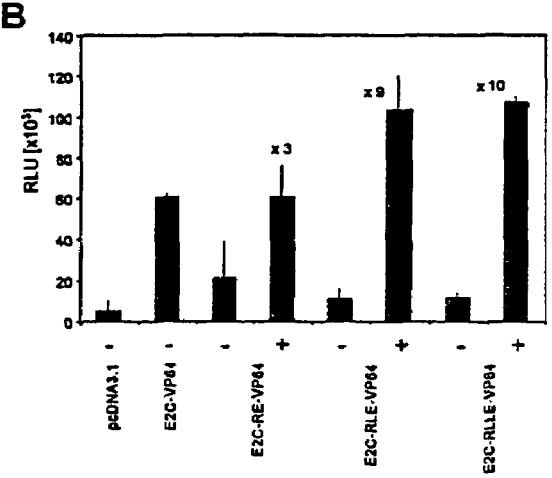
FIG. 3

```
            10               20              30              40              50              60
NNG GCC CAG GCG GCC CTC GAG CCC GGG GAG AAG CCC TAT GCT TGT CCG GAA TGT GGT AAG
NNC CGG GTC CGC CGG GAG CTC GGG CCC CTC TTC GGG ATA CGA ACA GGC CTT ACA CCA TTC
 X   A   Q   A   A   L   E   P   G   E   K   P   Y   A   C   P   E   C   G   K>

70               80              90             100             110             120
TCC TTC AGT CGC AGC GAT GTG CTG GTG CGC CAC CAG CGT ACC CAC ACG GGT GAA AAA CCG
AGG AAG TCA GCG TCG CTA CAC GAC CAC GCG GTG GTC GCA TGG GTG TGC CCA CTT TTT GGC
 S   F   S   R   S   D   V   L   V   R   H   Q   R   T   H   T   G   E   K   P>

130              140             150             160             170             180
TAT AAA TGC CCA GAG TGC GGC AAA TCT TTT AGC CGC AGC GAT GAT CTG GTT CGC CAT CAA
ATA TTT ACG GGT CTC ACG CCG TTT AGA AAA TCG GCG TCG CTA CTA GAC CAA GCG GTA GTT
 Y   K   C   P   E   C   G   K   S   F   S   R   S   D   D   L   V   R   H   Q>

190              200             210             220             230             240
CGC ACT CAT ACT GGC GAG AAG CCA TAC AAA TGT CCA GAA TGT GGC AAG TCT TTC TCC CAG
GCG TGA GTA TGA CCG CTC TTC GGT ATG TTT ACA GGT CTT ACA CCG TTC AGA AAG AGG GTC
 R   T   H   T   G   E   K   P   Y   K   C   P   E   C   G   K   S   F   S   Q>

250              260             270             280             290             300
TCT AGC CAC CTG GTT CGC CAC CAA CGT ACT CAC ACC GGG GAG AAG CCC TAT GCT TGT CCG
AGA TCG GTG GAC CAA GCG GTG GTT GCA TGA GTG TGG CCC CTC TTC GGG ATA CGA ACA GGC
 S   S   H   L   V   R   H   Q   R   T   H   T   G   E   K   P   Y   A   C   P>

310              320             330             340             350             360
GAA TGT GGT AAG TCC TTC AGC CGC AGC GAT AAC CTG GTG CGC CAC CAG CGT ACC CAC ACG
CTT ACA CCA TTC AGG AAG TCG GCG TCG CTA TTG GAC CAC GCG GTG GTC GCA TGG GTG TGC
 E   C   G   K   S   F   S   R   S   D   N   L   V   R   H   Q   R   T   H   T>

370              380             390             400             410             420
GGT GAA AAA CCG TAT AAA TGC CCA GAG TGC GGC AAA TCT TTT AGC CAG GCC GGC CAC CTG
CCA CTT TTT GGC ATA TTT ACG GGT CTC ACG CCG TTT AGA AAA TCG GTC CGG CCG GTG GAC
 G   E   K   P   Y   K   C   P   E   C   G   K   S   F   S   Q   A   G   H   L>

430              440             450             460             470             480
GCC AGC CAT CAA CGC ACT CAT ACT GGC GAG AAG CCA TAC AAA TGT CCA GAA TGT GGC AAG
CGG TCG GTA GTT GCG TGA GTA TGA CCG CTC TTC GGT ATG TTT ACA GGT CTT ACA CCG TTC
 A   S   H   Q   R   T   H   T   G   E   K   P   Y   K   C   P   E   C   G   K>

490              500             510             520             530             540
TCT TTC AGT GAT TGT CGT GAT CTT GCG AGG CAC CAA CGT ACT CAC ACC GGT AAA AAA ACT
AGA AAG TCA CTA ACA GCA CTA GAA CGC TCC GTG GTT GCA TGA GTG TGG CCA TTT TTT TGA
 S   F   S   D   C   R   D   L   A   R   H   Q   R   T   H   T   G   K   K   T>

550
AGT GGC CAG GCC GGC CNN
TCA CCG GTC CGG CCG GNN
 S   G   Q   A   G   X>
```

FIG. 4

```
              10              20              30              40              50              60
NNN GCC CAG GCG GCC CTC GAG CCC TAT GCT TGC CCT GTC GAG TCC TGC GAT CGC CGC TTT
NNN CGG GTC CGC CGG GAG CTC GGG ATA CGA ACG GGA CAG CTC AGG ACG CTA GCG GCG AAA
 X   A   Q   A   A   L   E   P   Y   A   C   P   V   E   S   C   D   R   R   F>

70              80              90             100             110             120
TCT AAG TCG GCT GAT CTG AAG CGC CAT ATC CGC ATC CAC ACA GGC CAG AAG CCC TTC CAG
AGA TTC AGC CGA CTA GAC TTC GCG GTA TAG GCG TAG GTG TGT CCG GTC TTC GGG AAG GTC
 S   K   S   A   D   L   K   R   H   I   R   I   H   T   G   Q   K   P   F   Q>

130             140             150             160             170             180
TGT CGA ATA TGC ATG CGT AAC TTC AGT CGT AGT GAC CAC CTT ACC ACC CAC ATC CGC ACC
ACA GCT TAT ACG TAC GCA TTG AAG TCA GCA TCA CTG GTG GAA TGG TGG GTG TAG GCG TGG
 C   R   I   C   M   R   N   F   S   R   S   D   H   L   T   T   H   I   R   T>

190             200             210             220             230             240
CAC ACA GGC GAG AAG CCT TTT GCC TGT GAC ATT TGT GGG AGG AAG TTT GCC AGG AGT GAT
GTG TGT CCG CTC TTC GGA AAA CGG ACA CTG TAA ACA CCC TCC TTC AAA CGG TCC TCA CTA
 H   T   G   E   K   P   F   A   C   D   I   C   G   R   K   F   A   R   S   D>

250             260             270             280             290             300
GAA CGC AAG AGG CAT ACC AAA ATC CAT ACC GGT GAG AAG CCC TAT GCT TGC CCT GTC GAG
CTT GCG TTC TCC GTA TGG TTT TAG GTA TGG CCA CTC TTC GGG ATA CGA ACG GGA CAG CTC
 E   R   K   R   H   T   K   I   H   T   G   E   K   P   Y   A   C   P   V   E>

310             320             330             340             350             360
TCC TGC GAT CGC CGC TTT TCT AAG TCG GCT GAT CTG AAG CGC CAT ATC CGC ATC CAC ACA
AGG ACG CTA GCG GCG AAA AGA TTC AGC CGA CTA GAC TTC GCG GTA TAG GCG TAG GTG TGT
 S   C   D   R   R   F   S   K   S   A   D   L   K   R   H   I   R   I   H   T>

370             380             390             400             410             420
GGC CAG AAG CCC TTC CAG TGT CGA ATA TGC ATG CGT AAC TTC AGT CGT AGT GAC CAC CTT
CCG GTC TTC GGG AAG GTC ACA GCT TAT ACG TAC GCA TTG AAG TCA GCA TCA CTG GTG GAA
 G   Q   K   P   F   Q   C   R   I   C   M   R   N   F   S   R   S   D   H   L>

430             440             450             460             470             480
ACC ACC CAC ATC CGC ACC CAC ACA GGC GAG AAG CCT TTT GCC TGT GAC ATT TGT GGG AGG
TGG TGG GTG TAG GCG TGG GTG TGT CCG CTC TTC GGA AAA CGG ACA CTG TAA ACA CCC TCC
 T   T   H   I   R   T   H   T   G   E   K   P   F   A   C   D   I   C   G   R>

490             500             510             520             530             540
AAG TTT GCC AGG AGT GAT GAA CGC AAG AGG CAT ACC AAA ATC CAT TTA AGA CAG AAG GAC
TTC AAA CGG TCC TCA CTA CTT GCG TTC TCC GTA TGG TTT TAG GTA AAT TCT GTC TTC CTG
 K   F   A   R   S   D   E   R   K   R   H   T   K   I   H   L   R   Q   K   D>

550             560
TCT AGA ACT AGT GGC CAG GCC GGC CNN
AGA TCT TGA TCA CCG GTC CGG CCG GNN
 S   R   T   S   G   Q   A   G   X>
```

FIG. 5

```
         10           20           30           40           50           60
NH₂-GCC CAG GCG GCC CTC GAG CCC GGG GAG AAG CCC TAT GCT TGT CCG GAA TGT GGT AAG
NH₂-CGG GTC CGC CGG GAG CTC GGG CCC CTC TTC GGG ATA CGA ACA GGC CTT ACA CCA TTC
    X   A   Q   A   A   L   E   P   G   E   K   P   Y   A   C   P   E   C   G   K>

70           80           90          100          110          120
    TCC TTC AGC ACC AGT GGC CAC CTG GTG CGC CAC CAG CGT ACC CAC ACG GGT GAA AAA CCG
    AGG AAG TCG TGG TCA CCG GTG GAC CAC GCG GTG GTC GCA TGG GTG TGC CCA CTT TTT GGC
    S   F   S   T   S   G   H   L   V   R   H   Q   R   T   H   T   G   E   K   P>

130          140          150          160          170          180
    TAT AAA TGC CCA GAG TGC GGC AAA TCT TTT AGT CGC AGC GAT GTG CTG GTG CGC CAT CAA
    ATA TTT ACG GGT CTC ACG CCG TTT AGA AAA TCA GCG TCG CTA CAC GAC CAC GCG GTA GTT
    Y   K   C   P   E   C   G   K   S   F   S   R   S   D   V   L   V   R   H   Q>

190          200          210          220          230          240
    CGC ACT CAT ACT GGC GAG AAG CCA TAC AAA TGT CCA GAA TGT GGC AAG TCT TTC TCA CGT
    GCG TGA GTA TGA CCG CTC TTC GGT ATG TTT ACA GGT CTT ACA CCG TTC AGA AAG AGT GCA
    R   T   H   T   G   E   K   P   Y   K   C   P   E   C   G   K   S   F   S   R>

250          260          270          280          290          300
    TCA GAC GAC TTG GTC CGT CAC CAA CGT ACT CAC ACC GGG GAG AAG CCC TAT GCT TGT CCG
    AGT CTG CTG AAC CAG GCA GTG GTT GCA TGA GTG TGG CCC CTC TTC GGG ATA CGA ACA GGC
    S   D   D   L   V   R   H   Q   R   T   H   T   G   E   K   P   Y   A   C   P>

310          320          330          340          350          360
    GAA TGT GGT AAG TCC TTC AGT GAT CCT GGC AAC CTG GTT CGC CAC CAG CGT ACC CAC ACG
    CTT ACA CCA TTC AGG AAG TCA CTA GGA CCG TTG GAC CAA GCG GTG GTC GCA TGG GTG TGC
    E   C   G   K   S   F   S   D   P   G   N   L   V   R   H   Q   R   T   H   T>

370          380          390          400          410          420
    GGT GAA AAA CCG TAT AAA TGC CCA GAG TGC GGC AAA TCT TTT AGT CGC TCC GAT AAA CTG
    CCA CTT TTT GGC ATA TTT ACG GGT CTC ACG CCG TTT AGA AAA TCA GCG AGG CTA TTT GAC
    G   E   K   P   Y   K   C   P   E   C   G   K   S   F   S   R   S   D   K   L>

430          440          450          460          470          480
    GTG CGC CAT CAA CGC ACT CAT ACT GGC GAG AAG CCA TAC AAA TGT CCA GAA TGT GGC AAG
    CAC GCG GTA GTT GCG TGA GTA TGA CCG CTC TTC GGT ATG TTT ACA GGT CTT ACA CCG TTC
    V   R   H   Q   R   T   H   T   G   E   K   P   Y   K   C   P   E   C   G   K>

490          500          510          520          530          540
    TCT TTC TCC CAG TCT AGC CAC CTG GTT CGC CAC CAA CGT ACT CAC ACC GGT AAA AAA ACT
    AGA AAG AGG GTC AGA TCG GTG GAC CAA GCG GTG GTT GCA TGA GTG TGG CCA TTT TTT TGA
    S   F   S   Q   S   S   H   L   V   R   H   Q   R   T   H   T   G   K   K   T>

550
AGT GGC CAG GCC GGC C-NH₂
TCA CCG GTC CGG CCG G-NH₂
    S   G   Q   A   G   X>
```

FIG. 6

```
GGGCGCGCCCAGGAAACTATGACCTTCAAAGACGTTGAAGTTACCTTCTCTCAGGACGAATGGGGTTGGC
TGGACTCCGCTCAGCGTAACCTGTACCGTGACGTTATGCTGGAAAACTACCGCAACATGGCTTCCCTGGT
TGGCGGCGGCCGCGGTGGTCAGGAAACTATGACCTTCAAAGACGTTGAAGTTACCTTCTCTCAGGACGAA
TGGGGTTGGCTGGACTCCGCTCAGCGTAACCTGTACCGTGACGTTATGCTGGAAAACTACCGCAACATGG
CTTCCCTGGTTGGCTTAATTAAC
```

FIG. 7

```
GGGCGCGCCGCTGCCGTGCGCATGAACATCCAGATGCTGCTCGAAGCCGCTGATTATCTGGAACGCCGGG
AGCGCGAAGCCGAGCACGGCTACGCCAGCATGCTGCCATATGGCGGCCGCGGTGGTGCCGCTGCCGTGCG
CATGAACATCCAGATGCTGCTCGAAGCCGCTGATTATCTGGAACGCCGGGAGCGCGAAGCCGAGCACGGC
TACGCCAGCATGCTGCCATATTTAATTAAC
```

```
            10          20          30          40          50          60
GGA TCC GCC ACC ATG GCC CAG GCG GCC CTC GAG CCC GGG GAG AAG CCC TAT GCT TGT CCG
CCT AGG CGG TGG TAC CGG GTC CGC CGG GAG CTC GGG CCC CTC TTC GGG ATA CGA ACA GGC
 G   S   A   T   M   A   Q   A   A   L   E   P   G   E   K   P   Y   A   C   P>

70          80          90         100         110         120
GAA TGT GGT AAG TCC TTC AGT AGG AAG GAT TCG CTT GTG AGG CAC CAG CGT ACC CAC ACG
CTT ACA CCA TTC AGG AAG TCA TCC TTC CTA AGC GAA CAC TCC GTG GTC GCA TGG GTG TGC
 E   C   G   K   S   F   S   R   K   D   S   L   V   R   H   Q   R   T   H   T>

130         140         150         160         170         180
GGT GAA AAA CCG TAT AAA TGC CCA GAG TGC GGC AAA TCT TTT AGT CAG TCG GGG GAT CTT
CCA CTT TTT GGC ATA TTT ACG GGT CTC ACG CCG TTT AGA AAA TCA GTC AGC CCC CTA GAA
 G   E   K   P   Y   K   C   P   E   C   G   K   S   F   S   Q   S   G   D   L>

190         200         210         220         230         240
AGG CGT CAT CAA CGC ACT CAT ACT GGC GAG AAG CCA TAC AAA TGT CCA GAA TGT GGC AAG
TCC GCA GTA GTT GCG TGA GTA TGA CCG CTC TTC GGT ATG TTT ACA GGT CTT ACA CCG TTC
 R   R   H   Q   R   T   H   T   G   E   K   P   Y   K   C   P   E   C   G   K>

250         260         270         280         290         300
TCT TTC AGT GAT TGT CGT GAT CTT GCG AGG CAC CAA CGT ACT CAC ACC GGG GAG AAG CCC
AGA AAG TCA CTA ACA GCA CTA GAA CGC TCC GTG GTT GCA TGA GTG TGG CCC CTC TTC GGG
 S   F   S   D   C   R   D   L   A   R   H   Q   R   T   H   T   G   E   K   P>

310         320         330         340         350         360
TAT GCT TGT CCG GAA TGT GGT AAG TCC TTC TCT CAG AGC TCT CAC CTG GTG CGC CAC CAG
ATA CGA ACA GGC CTT ACA CCA TTC AGG AAG AGA GTC TCG AGA GTG GAC CAC GCG GTG GTC
 Y   A   C   P   E   C   G   K   S   F   S   Q   S   S   H   L   V   R   H   Q>

370         380         390         400         410         420
CGT ACC CAC ACG GGT GAA AAA CCG TAT AAA TGC CCA GAG TGC GGC AAA TCT TTT AGT GAC
GCA TGG GTG TGC CCA CTT TTT GGC ATA TTT ACG GGT CTC ACG CCG TTT AGA AAA TCA CTG
 R   T   H   T   G   E   K   P   Y   K   C   P   E   C   G   K   S   F   S   D>

430         440         450         460         470         480
TGC CGC GAC CTT GCT CGC CAT CAA CGC CAT CAT ACT GGC GAG AAG CCA TAC AAA TGT CCA
ACG GCG CTG GAA CGA GCG GTA GTT GCG TGA GTA TGA CCG CTC TTC GGT ATG TTT ACA GGT
 C   R   D   L   A   R   H   Q   R   T   H   T   G   E   K   P   Y   K   C   P>

490         500         510         520         530         540
GAA TGT GGC AAG TCT TTC AGC CGC TCT GAC AAG CTG GTG CGT CAC CAA CGT ACT CAC ACC
CTT ACA CCG TTC AGA AAG TCG GCG AGA CTG TTC GAC CAC GCA GTG GTT GCA TGA GTG TGG
 E   C   G   K   S   F   S   R   S   D   K   L   V   R   H   Q   R   T   H   T>

550         560         570         580         590         600
GGT AAA AAA ACT AGT GGC CAG GCC GGC CGC CGA AAT GAA ATG GGT GCT TCA GGA GAC ATG
CCA TTT TTT TGA TCA CCG GTC CGG CCG GCG GCT TTA CTT TAC CCA CGA AGT CCT CTG TAC
 G   K   K   T   S   G   Q   A   G   R   R   N   E   M   G   A   S   G   D   M>

610         620         630         640         650         660
AGG GCT GCC AAC CTT TGG CCA AGC CCT CTT GTG ATT AAG CAC ACT AAG AAG AAT AGC CCT
TCC CGA CGG TTG GAA ACC GGT TCG GGA GAA CAC TAA TTC GTG TGA TTC TTC TTA TCG GGA
 R   A   A   N   L   W   P   S   P   L   V   I   K   H   T   K   K   N   S   P>

670         680         690         700         710         720
GCC TTG TCC TTG ACA GCT GAC CAG ATG GTC AGT GCC TTG TTG GAT GCT GAA CCG CCC ATG
CGG AAC AGG AAC TGT CGA CTG GTC TAC CAG TCA CGG AAC AAC CTA CGA CTT GGC GGG TAC
 A   L   S   L   T   A   D   Q   M   V   S   A   L   L   D   A   E   P   P   M>

730         740         750         760         770         780
ATC TAT TCT GAA TAT GAT CCT TCT AGA CCC TTC AGT GAA GCC TCA ATG ATG GGC TTA TTG
```

FIG. 9-2

```
TAG ATA AGA CTT ATA CTA GGA AGA TCT GGG AAG TCA CTT CGG AGT TAC TAC CCG AAT AAC
 I   Y   S   E   Y   D   P   S   R   P   F   S   E   A   S   M   M   G   L   L>

790         800         810         820         830         840
ACC AAC CTA GCA GAT AGG GAG CTG GTT CAT ATG ATC AAC TGG GCA AAG AGA GTG CCA GGC
TGG TTG GAT CGT CTA TCC CTC GAC CAA GTA TAC TAG TTG ACC CGT TTC TCT CAC GGT CCG
 T   N   L   A   D   R   E   L   V   H   M   I   N   W   A   K   R   V   P   G>

850         860         870         880         890         900
TTT GGG GAC TTG AAT CTC CAT GAT CAG GTC CAC CTT CTC GAG TGT GCC TGG CTG GAG ATT
AAA CCC CTG AAC TTA GAG GTA CTA GTC CAG GTG GAA GAG CTC ACA CGG ACC GAC CTC TAA
 F   G   D   L   N   L   H   D   Q   V   H   L   L   E   C   A   W   L   E   I>

910         920         930         940         950         960
CTG ATG ATT GGT CTC GTC TGG CGC TCC ATG GAA CAC CCG GGG AAG CTC CTG TTT GCT CCT
GAC TAC TAA CCA GAG CAG ACC GCG AGG TAC CTT GTG GGC CCC TTC GAG GAC AAA CGA GGA
 L   M   I   G   L   V   W   R   S   M   E   H   P   G   K   L   L   F   A   P>

970         980         990        1000        1010        1020
AAC TTG CTC CTG GAC AGG AAT CAA GGT AAA TGT GTG GAA GGC ATG GTG GAG ATC TTT GAC
TTG AAC GAG GAC CTG TCC TTA GTT CCA TTT ACA CAC CTT CCG TAC CAC CTC TAG AAA CTG
 N   L   L   L   D   R   N   Q   G   K   C   V   E   G   M   V   E   I   F   D>

1030        1040        1050        1060        1070        1080
ATG TTG CTT GCT ACG TCA AGT CGG TTC CGC ATG ATG AAC CTG CAG GGT GAA GAG TTT GTG
TAC AAC GAA CGA TGC AGT TCA GCC AAG GCG TAC TAC TTG GAC GTC CCA CTT CTC AAA CAC
 M   L   L   A   T   S   S   R   F   R   M   M   N   L   Q   G   E   E   F   V>

1090        1100        1110        1120        1130        1140
TGC CTC AAA TCC ATC ATT TTG CTT AAT TCC GGA GTG TAC ACG TTT CTG TCC AGC ACC TTG
ACG GAG TTT AGG TAG TAA AAC GAA TTA AGG CCT CAC ATG TGC AAA GAC AGG TCG TGG AAC
 C   L   K   S   I   I   L   L   N   S   G   V   Y   T   F   L   S   S   T   L>

1150        1160        1170        1180        1190        1200
AAG TCT CTG GAA GAG AAG GAC CAC ATC CAC CGT GTC CTG GAC AAG ATC ACA GAC ACT TTG
TTC AGA GAC CTT CTC TTC CTG GTG TAG GTG GCA CAG GAC CTG TTC TAG TGT CTG TGA AAC
 K   S   L   E   E   K   D   H   I   H   R   V   L   D   K   I   T   D   T   L>

1210        1220        1230        1240        1250        1260
ATC CAC CTG ATG GCC AAA GCT GGC CTG ACT CTG CAG CAG CAG CAT CGC CGC CTA GCT CAG
TAG GTG GAC TAC CGG TTT CGA CCG GAC TGA GAC GTC GTC GTC GTA GCG GCG GAT CGA GTC
 I   H   L   M   A   K   A   G   L   T   L   Q   Q   Q   H   R   R   L   A   Q>

1270        1280        1290        1300        1310        1320
CTC CTT CTC ATT CTT TCC CAT ATC CGG CAC ATG AGT AAC AAA GGC ATG GAG CAT CTC TAC
GAG GAA GAG TAA GAA AGG GTA TAG GCC GTG TAC TCA TTG TTT CCG TAC CTC GTA GAG ATG
 L   L   L   I   L   S   H   I   R   H   M   S   N   K   G   M   E   H   L   Y>

1330        1340        1350        1360        1370        1380
AAC ATG AAA TGC AAG AAC GTT GTG CCC CTC TAT GAC CTG CTC CTG GAG ATG TTG GAT GCC
TTG TAC TTT ACG TTC TTG CAA CAC GGG GAG ATA CTG GAC GAG GAC CTC TAC AAC CTA CGG
 N   M   K   C   K   N   V   V   P   L   Y   D   L   L   L   E   M   L   D   A>

1390        1400        1410        1420        1430        1440
CAC CGC CTT CAT GCC CCA GCC AGT CGC ATG GGA GTG CCC CCA GAG GAG CCC AGC CAG ACC
GTG GCG GAA GTA CGG GGT CGG TCA GCG TAC CCT CAC GGG GGT CTC CTC GGG TCG GTC TGG
 H   R   L   H   A   P   A   S   R   M   G   V   P   P   E   E   P   S   Q   T>

1450        1460        1470        1480        1490        1500
CAG CTG GCC ACC ACC AGC TCC ACT TCA GCA CAT TCC TTA CAA ACC TAC TAC ATA CCC CCG
GTC GAC CGG TGG TGG TCG AGG TGA AGT CGT GTA AGG AAT GTT TGG ATG ATG TAT GGG GGC
 Q   L   A   T   T   S   S   T   S   A   H   S   L   Q   T   Y   Y   I   P   P>

```
GAA GCA GAG GGC TTC CCC AAC ACG ATC TCC TCT GGT GGC GGT GGC TCG GGC GGT GGT GGG
CTT CGT CTC CCG AAG GGG TTG TGC TAG AGG AGA CCA CCG CCA CCG AGC CCG CCA CCA CCC
 E   A   E   G   F   P   N   T   I   S   S   G   G   G   S   G   G   G  G>

1570        1580        1590        1600        1610        1620
GGT GGT TCC ACT AGC TCT TCC AAT GAA ATG GGT GCT TCA GGA GAC ATG AGG GCT GCC AAC
CCA CCA AGG TGA TCG AGA AGG TTA CTT TAC CCA CGA AGT CCT CTG TAC TCC CGA CGG TTG
 G   G   S   T   S   S   S   N   E   M   G   A   S   G   D   M   R   A   A   N>

1630        1640        1650        1660        1670        1680
CTT TGG CCA AGC CCT CTT GTG ATT AAG CAC ACT AAG AAG AAT AGC CCT GCC TTG TCC TTG
GAA ACC GGT TCG GGA GAA CAC TAA TTC GTG TGA TTC TTC TTA TCG GGA CGG AAC AGG AAC
 L   W   P   S   P   L   V   I   K   H   T   K   K   N   S   P   A   L   S   L>

1690        1700        1710        1720        1730        1740
ACA GCT GAC CAG ATG GTC AGT GCC TTG TTG GAT GCT GAA CCG CCC ATG ATC TAT TCT GAA
TGT CGA CTG GTC TAC CAG TCA CGG AAC AAC CTA CGA CTT GGC GGG TAC TAG ATA AGA CTT
 T   A   D   Q   M   V   S   A   L   L   D   A   E   P   P   M   I   Y   S   E>

1750        1760        1770        1780        1790        1800
TAT GAT CCT TCT AGA CCC TTC AGT GAA GCC TCA ATG ATG GGC TTA TTG ACC AAC CTA GCA
ATA CTA GGA AGA TCT GGG AAG TCA CTT CGG AGT TAC TAC CCG AAT AAC TGG TTG GAT CGT
 Y   D   P   S   R   P   F   S   E   A   S   M   M   G   L   L   T   N   L   A>

1810        1820        1830        1840        1850        1860
GAT AGG GAG CTG GTT CAT ATG ATC AAC TGG GCA AAG AGA GTG CCA GGC TTT GGG GAC TTG
CTA TCC CTC GAC CAA GTA TAC TAG TTG ACC CGT TTC TCT CAC GGT CCG AAA CCC CTG AAC
 D   R   E   L   V   H   M   I   N   W   A   K   R   V   P   G   F   G   D   L>

1870        1880        1890        1900        1910        1920
AAT CTC CAT GAT CAG GTC CAC CTT CTC GAG TGT GCC TGG CTG GAG ATT CTG ATG ATT GGT
TTA GAG GTA CTA GTC CAG GTG GAA GAG CTC ACA CGG ACC GAC CTC TAA GAC TAC TAA CCA
 N   L   H   D   Q   V   H   L   L   E   C   A   W   L   E   I   L   M   I   G>

1930        1940        1950        1960        1970        1980
CTC GTC TGG CGC TCC ATG GAA CAC CCG GGG AAG CTC CTG TTT GCT CCT AAC TTG CTC CTG
GAG CAG ACC GCG AGG TAC CTT GTG GGC CCC TTC GAG GAC AAA CGA GGA TTG AAC GAG GAC
 L   V   W   R   S   M   E   H   P   G   K   L   L   F   A   P   N   L   L   L>

1990        2000        2010        2020        2030        2040
GAC AGG AAT CAA GGT AAA TGT GTG GAA GGC ATG GTG GAG ATC TTT GAC ATG TTG CTT GCT
CTG TCC TTA GTT CCA TTT ACA CAC CTT CCG TAC CAC CTC TAG AAA CTG TAC AAC GAA CGA
 D   R   N   Q   G   K   C   V   E   G   M   V   E   I   F   D   M   L   L   A>

2050        2060        2070        2080        2090        2100
ACG TCA AGT CGG TTC CGC ATG ATG AAC CTG CAG GGT GAA GAG TTT GTG TGC CTC AAA TCC
TGC AGT TCA GCC AAG GCG TAC TAC TTG GAC GTC CCA CTT CTC AAA CAC ACG GAG TTT AGG
 T   S   S   R   F   R   M   M   N   L   Q   G   E   E   F   V   C   L   K   S>

2110        2120        2130        2140        2150        2160
ATC ATT TTG CTT AAT TCC GGA GTG TAC ACG TTT CTG TCC AGC ACC TTG AAG TCT CTG GAA
TAG TAA AAC GAA TTA AGG CCT CAC ATG TGC AAA GAC AGG TCG TGG AAC TTC AGA GAC CTT
 I   I   L   L   N   S   G   V   Y   T   F   L   S   S   T   L   K   S   L   E>

2170        2180        2190        2200        2210        2220
GAG AAG GAC CAC ATC CAC CGT GTC CTG GAC AAG ATC ACA GAC ACT TTG ATC CAC CTG ATG
CTC TTC CTG GTG TAG GTG GCA CAG GAC CTG TTC TAG TGT CTG TGA AAC TAG GTG GAC TAC
 E   K   D   H   I   H   R   V   L   D   K   I   T   D   T   L   I   H   L   M>

2230        2240        2250        2260        2270        2280
GCC AAA GCT GGC CTG ACT CTG CAG CAG CAG CAT CGC CGC CTA GCT CAG CTC CTT CTC ATT
CGG TTT CGA CCG GAC TGA GAC GTC GTC GTC GTA GCG GCG GAT CGA GTC GAG GAA GAG TAA
 A   K   A   G   L   T   L   Q   Q   Q   H   R   R   L   A   Q   L   L   L   I>
```

FIG. 9-4

```
       2290        2300        2310        2320        2330        2340
CTT TCC CAT ATC CGG CAC ATG AGT AAC AAA GGC ATG GAG CAT CTC TAC AAC ATG AAA TGC
GAA AGG GTA TAG GCC GTG TAC TCA TTG TTT CCG TAC CTC GTA GAG ATG TTG TAC TTT ACG
 L   S   H   I   R   H   M   S   N   K   G   M   E   H   L   Y   N   M   K   C>

2350        2360        2370        2380        2390        2400
AAG AAC GTT GTG CCC CTC TAT GAC CTG CTC CTG GAG ATG TTG GAT GCC CAC CGC CTT CAT
TTC TTG CAA CAC GGG GAG ATA CTG GAC GAG GAC CTC TAC AAC CTA CGG GTG GCG GAA GTA
 K   N   V   V   P   L   Y   D   L   L   L   E   M   L   D   A   H   R   L   H>

2410        2420        2430        2440        2450        2460
GCC CCA GCC AGT CGC ATG GGA GTG CCC CCA GAG GAG CCC AGC CAG ACC CAG CTG GCC ACC
CGG GGT CGG TCA GCG TAC CCT CAC GGG GGT CTC CTC GGG TCG GTC TGG GTC GAC CGG TGG
 A   P   A   S   R   M   G   V   P   P   E   E   P   S   Q   T   Q   L   A   T>

2470        2480        2490        2500        2510        2520
ACC AGC TCC ACT TCA GCA CAT TCC TTA CAA ACC TAC TAC ATA CCC CCG GAA GCA GAG GGC
TGG TCG AGG TGA AGT CGT GTA AGG AAT GTT TGG ATG ATG TAT GGG GGC CTT CGT CTC CCG
 T   S   S   T   S   A   H   S   L   Q   T   Y   Y   I   P   P   E   A   E   G>

2530        2540        2550        2560        2570        2580
TTC CCC AAC ACG ATC GGG CGC GCC GAC GCG CTG GAC GAT TTC GAT CTC GAC ATG CTG GGT
AAG GGG TTG TGC TAG CCC GCG CGG CTG CGC GAC CTG CTA AAG CTA GAG CTG TAC GAC CCA
 F   P   N   T   I   G   R   A   D   A   L   D   D   F   D   L   D   M   L   G>

2590        2600        2610        2620        2630        2640
TCT GAT GCC CTC GAT GAC TTT GAC CTG GAT ATG TTG GGA AGC GAC GCA TTG GAT GAC TTT
AGA CTA CGG GAG CTA CTG AAA CTG GAC CTA TAC AAC CCT TCG CTG CGT AAC CTA CTG AAA
 S   D   A   L   D   D   F   D   L   D   M   L   G   S   D   A   L   D   D   F>

2650        2660        2670        2680        2690        2700
GAT CTG GAC ATG CTC GGC TCC GAT GCT CTG GAC GAT TTC GAT CTC GAT ATG TTA ATT AAC
CTA GAC CTG TAC GAG CCG AGG CTA CGA GAC CTG CTA AAG CTA GAG CTA TAC AAT TAA TTG
 D   L   D   M   L   G   S   D   A   L   D   D   F   D   L   D   M   L   I   N>

2710        2720        2730
TAC CCG TAC GAC GTT CCG GAC TAC GCT TCT TGA GAA TTC
ATG GGC ATG CTG CAA GGC CTG ATG CGA AGA ACT CTT AAG
 Y   P   Y   D   V   P   D   Y   A   S   *   E   F>
```

FIG. 10-1

```
            10              20              30              40              50              60
GGA TCC GCC ACC ATG GCC CAG GCG GCC CTC GAG CCC GGG GAG AAG CCC TAT GCT TGT CCG
CCT AGG CGG TGG TAC CGG GTC CGC CGG GAG CTC GGG CCC CTC TTC GGG ATA CGA ACA GGC
 G   S   A   T   M   A   Q   A   A   L   E   P   G   E   K   P   Y   A   C   P>

70              80              90             100             110             120
GAA TGT GGT AAG TCC TTC AGT AGG AAG GAT TCG CTT GTG AGG CAC CAG CGT ACC CAC ACG
CTT ACA CCA TTC AGG AAG TCA TCC TTC CTA AGC GAA CAC TCC GTG GTC GCA TGG GTG TGC
 E   C   G   K   S   F   S   R   K   D   S   L   V   R   H   Q   R   T   H   T>

130             140             150             160             170             180
GGT GAA AAA CCG TAT AAA TGC CCA GAG TGC GGC AAA TCT TTT AGT CAG TCG GGG GAT CTT
CCA CTT TTT GGC ATA TTT ACG GGT CTC ACG CCG TTT AGA AAA TCA GTC AGC CCC CTA GAA
 G   E   K   P   Y   K   C   P   E   C   G   K   S   F   S   Q   S   G   D   L>

190             200             210             220             230             240
AGG CGT CAT CAA CGC ACT CAT ACT GGC GAG AAG CCA TAC AAA TGT CCA GAA TGT GGC AAG
TCC GCA GTA GTT GCG TGA GTA TGA CCG CTC TTC GGT ATG TTT ACA GGT CTT ACA CCG TTC
 R   R   H   Q   R   T   H   T   G   E   K   P   Y   K   C   P   E   C   G   K>

250             260             270             280             290             300
TCT TTC AGT GAT TGT CGT GAT CTT GCG AGG CAC CAA CGT ACT CAC ACC GGG GAG AAG CCC
AGA AAG TCA CTA ACA GCA CTA GAA CGC TCC GTG GTT GCA TGA GTG TGG CCC CTC TTC GGG
 S   F   S   D   C   R   D   L   A   R   H   Q   R   T   H   T   G   E   K   P>

310             320             330             340             350             360
TAT GCT TGT CCG GAA TGT GGT AAG TCC TTC TCT CAG AGC TCT CAC CTG GTG CGC CAC CAG
ATA CGA ACA GGC CTT ACA CCA TTC AGG AAG AGA GTC TCG AGA GTG GAC CAC GCG GTG GTC
 Y   A   C   P   E   C   G   K   S   F   S   Q   S   S   H   L   V   R   H   Q>

370             380             390             400             410             420
CGT ACC CAC ACG GGT GAA AAA CCG TAT AAA TGC CCA GAG TGC GGC AAA TCT TTT AGT GAC
GCA TGG GTG TGC CCA CTT TTT GGC ATA TTT ACG GGT CTC ACG CCG TTT AGA AAA TCA CTG
 R   T   H   T   G   E   K   P   Y   K   C   P   E   C   G   K   S   F   S   D>

430             440             450             460             470             480
TGC CGC GAC CTT GCT CGC CAT CAA CGC ACT CAT ACT GGC GAG AAG CCA TAC AAA TGT CCA
ACG GCG CTG GAA CGA GCG GTA GTT GCG TGA GTA TGA CCG CTC TTC GGT ATG TTT ACA GGT
 C   R   D   L   A   R   H   Q   R   T   H   T   G   E   K   P   Y   K   C   P>

490             500             510             520             530             540
GAA TGT GGC AAG TCT TTC AGC CGC TCT GAC AAG CTG GTG CGT CAC CAA CGT ACT CAC ACC
CTT ACA CCG TTC AGA AAG TCG GCG AGA CTG TTC GAC CAC GCA GTG GTT GCA TGA GTG TGG
 E   C   G   K   S   F   S   R   S   D   K   L   V   R   H   Q   R   T   H   T>

550             560             570             580             590             600
GGT AAA AAA ACT AGT GGC CAG GCC GGC CGC CGA AAT GAA ATG GGT GCT TCA GGA GAC ATG
CCA TTT TTT TGA TCA CCG GTC CGG CCG GCT GCT TTA CTT TAC CCA CGA AGT CCT CTG TAC
 G   K   K   T   S   G   Q   A   G   R   R   N   E   M   G   A   S   G   D   M>

610             620             630             640             650             660
AGG GCT GCC AAC CTT TGG CCA AGC CCT CTT GTG ATT AAG CAC ACT AAG AAG AAT AGC CCT
TCC CGA CGG TTG GAA ACC GGT TCG GGA GAA CAC TAA TTC GTG TGA TTC TTC TTA TCG GGA
 R   A   A   N   L   W   P   S   P   L   V   I   K   H   T   K   K   N   S   P>

670             680             690             700             710             720
GCC TTG TCC TTG ACA GCT GAC CAG ATG GTC AGT GCC TTG TTG GAT GCT GAA CCG CCC ATG
CGG AAC AGG AAC TGT CGA CTG GTC TAC CAG TCA CGG AAC AAC CTA CGA CTT GGC GGG TAC
 A   L   S   L   T   A   D   Q   M   V   S   A   L   L   D   A   E   P   P   M>

730             740             750             760             770             780
ATC TAT TCT GAA TAT GAT CCT TCT AGA CCC TTC AGT GAA GCC TCA ATG ATG GGC TTA TTG
```

FIG. 10-2

```
    TAG ATA AGA CTT ATA CTA GGA AGA TCT GGG AAG TCA CTT CGG AGT TAC TAC CCG AAT AAC
     I   Y   S   E   Y   D   P   S   R   P   F   S   E   A   S   M   M   G   L   L>

790         800         810         820         830         840
    ACC AAC CTA GCA GAT AGG GAG CTG GTT CAT ATG ATC AAC TGG GCA AAG AGA GTG CCA GGC
    TGG TTG GAT CGT CTA TCC CTC GAC CAA GTA TAC TAG TTG ACC CGT TTC TCT CAC GGT CCG
     T   N   L   A   D   R   E   L   V   H   M   I   N   W   A   K   R   V   P   G>

850         860         870         880         890         900
    TTT GGG GAC TTG AAT CTC CAT GAT CAG GTC CAC CTT CTC GAG TGT GCC TGG CTG GAG ATT
    AAA CCC CTG AAC TTA GAG GTA CTA GTC CAG GTG GAA GAG CTC ACA CGG ACC GAC CTC TAA
     F   G   D   L   N   L   H   D   Q   V   H   L   L   E   C   A   W   L   E   I>

910         920         930         940         950         960
    CTG ATG ATT GGT CTC GTC TGG CGC TCC ATG GAA CAC CCG GGG AAG CTC CTG TTT GCT CCT
    GAC TAC TAA CCA GAG CAG ACC GCG AGG TAC CTT GTG GGC CCC TTC GAG GAC AAA CGA GGA
     L   M   I   G   L   V   W   R   S   M   E   H   P   G   K   L   L   F   A   P>

970         980         990        1000        1010        1020
    AAC TTG CTC CTG GAC AGG AAT CAA GGT AAA TGT GTG GAA GGC ATG GTG GAG ATC TTT GAC
    TTG AAC GAG GAC CTG TCC TTA GTT CCA TTT ACA CAC CTT CCG TAC CAC CTC TAG AAA CTG
     N   L   L   L   D   R   N   Q   G   K   C   V   E   G   M   V   E   I   F   D>

1030        1040        1050        1060        1070        1080
    ATG TTG CTT GCT ACG TCA AGT CGG TTC CGC ATG ATG AAC CTG CAG GGT GAA GAG TTT GTG
    TAC AAC GAA CGA TGC AGT TCA GCC AAG GCG TAC TAC TTG GAC GTC CCA CTT CTC AAA CAC
     M   L   L   A   T   S   S   R   F   R   M   M   N   L   Q   G   E   E   F   V>

1090        1100        1110        1120        1130        1140
    TGC CTC AAA TCC ATC ATT TTG CTT AAT TCC GGA GTG TAC ACG TTT CTG TCC AGC ACC TTG
    ACG GAG TTT AGG TAG TAA AAC GAA TTA AGG CCT CAC ATG TGC AAA GAC AGG TCG TGG AAC
     C   L   K   S   I   I   L   L   N   S   G   V   Y   T   F   L   S   S   T   L>

1150        1160        1170        1180        1190        1200
    AAG TCT CTG GAA GAG AAG GAC CAC ATC CAC CGT GTC CTG GAC AAG ATC ACA GAC ACT TTG
    TTC AGA GAC CTT CTC TTC CTG GTG TAG GTG GCA CAG GAC CTG TTC TAG TGT CTG TGA AAC
     K   S   L   E   E   K   D   H   I   H   R   V   L   D   K   I   T   D   T   L>

1210        1220        1230        1240        1250        1260
    ATC CAC CTG ATG GCC AAA GCT GGC CTG ACT CTG CAG CAG CAG CAT CGC CGC CTA GCT CAG
    TAG GTG GAC TAC CGG TTT CGA CCG GAC TGA GAC GTC GTC GTC GTA GCG GCG GAT CGA GTC
     I   H   L   M   A   K   A   G   L   T   L   Q   Q   Q   H   R   R   L   A   Q>

1270        1280        1290        1300        1310        1320
    CTC CTT CTC ATT CTT TCC CAT ATC CGG CAC ATG AGT AAC AAA GGC ATG GAG CAT CTC TAC
    GAG GAA GAG TAA GAA AGG GTA TAG GCC GTG TAC TCA TTG TTT CCG TAC CTC GTA GAG ATG
     L   L   L   I   L   S   H   I   R   H   M   S   N   K   G   M   E   H   L   Y>

1330        1340        1350        1360        1370        1380
    AAC ATG AAA TGC AAG AAC GTT GTG CCC CTC TAT GAC CTG CTC CTG GAG ATG TTG GAT GCC
    TTG TAC TTT ACG TTC TTG CAA CAC GGG GAG ATA CTG GAC GAG GAC CTC TAC AAC CTA CGG
     N   M   K   C   K   N   V   V   P   L   Y   D   L   L   L   E   M   L   D   A>

1390        1400        1410        1420        1430        1440
    CAC CGC CTT CAT GCC CCA GCC AGT CGC ATG GGA GTG CCC CCA GAG GAG CCC AGC CAG ACC
    GTG GCG GAA GTA CGG GGT CGG TCA GCG TAC CCT CAC GGG GGT CTC CTC GGG TCG GTC TGG
     H   R   L   H   A   P   A   S   R   M   G   V   P   P   E   E   P   S   Q   T>

1450        1460        1470        1480        1490        1500
    CAG CTG GCC ACC ACC AGC TCC ACT TCA GCA CAT TCC TTA CAA ACC TAC TAC ATA CCC CCG
    GTC GAC CGG TGG TGG TCG AGG TGA AGT CGT GTA AGG AAT GTT TGG ATG ATG TAT GGG GGC
     Q   L   A   T   T   S   S   T   S   A   H   S   L   Q   T   Y   Y   I   P   P>

```
GAA GCA GAG GGC TTC CCC AAC ACG ATC TCC TCT GGT GGC GGT GGC TCG GGC GGT GGT GGC
CTT CGT CTC CCG AAG GGG TTG TGC TAG AGG AGA CCA CCG CCA CCG AGC CCG CCA CCA CCG
 E   A   E   G   F   P   N   T   I   S   S   G   G   G   S   G   G   G   G>

1570        1580        1590        1600        1610        1620
GGT GGT TCC ACT AGC GGC GGT GGC GGT GGC TCC TCT GGT GGC GGT GGC GGT TCT TCC AAT
CCA CCA AGG TGA TCG CCG CCA CCG CCA CCG AGG AGA CCA CCG CCA CCG CCA AGA AGG TTA
 G   G   S   T   S   G   G   G   G   G   S   S   G   G   G   G   G   S   S   N>

1630        1640        1650        1660        1670        1680
GAA ATG GGT GCT TCA GGA GAC ATG AGG GCT GCC AAC CTT TGG CCA AGC CCT CTT GTG ATT
CTT TAC CCA CGA AGT CCT CTG TAC TCC CGA CGG TTG GAA ACC GGT TCG GGA GAA CAC TAA
 E   M   G   A   S   G   D   M   R   A   A   N   L   W   P   S   P   L   V   I>

1690        1700        1710        1720        1730        1740
AAG CAC ACT AAG AAG AAT AGC CCT GCC TTG TCC TTG ACA GCT GAC CAG ATG GTC AGT GCC
TTC GTG TGA TTC TTC TTA TCG GGA CGG AAC AGG AAC TGT CGA CTG GTC TAC CAG TCA CGG
 K   H   T   K   K   N   S   P   A   L   S   L   T   A   D   Q   M   V   S   A>

1750        1760        1770        1780        1790        1800
TTG TTG GAT GCT GAA CCG CCC ATG ATC TAT TCT GAA TAT GAT CCT TCT AGA CCC TTC AGT
AAC AAC CTA CGA CTT GGC GGG TAC TAG ATA AGA CTT ATA CTA GGA AGA TCT GGG AAG TCA
 L   L   D   A   E   P   P   M   I   Y   S   E   Y   D   P   S   R   P   F   S>

1810        1820        1830        1840        1850        1860
GAA GCC TCA ATG ATG GGC TTA TTG ACC AAC CTA GCA GAT AGG GAG CTG GTT CAT ATG ATC
CTT CGG AGT TAC TAC CCG AAT AAC TGG TTG GAT CGT CTA TCC CTC GAC CAA GTA TAC TAG
 E   A   S   M   M   G   L   L   T   N   L   A   D   R   E   L   V   H   M   I>

1870        1880        1890        1900        1910        1920
AAC TGG GCA AAG AGA GTG CCA GGC TTT GGG GAC TTG AAT CTC CAT GAT CAG GTC CAC CTT
TTG ACC CGT TTC TCT CAC GGT CCG AAA CCC CTG AAC TTA GAG GTA CTA GTC CAG GTG GAA
 N   W   A   K   R   V   P   G   F   G   D   L   N   L   H   D   Q   V   H   L>

1930        1940        1950        1960        1970        1980
CTC GAG TGT GCC TGG CTG GAG ATT CTG ATG ATT GGT CTC GTC TGG CGC TCC ATG GAA CAC
GAG CTC ACA CGG ACC GAC CTC TAA GAC TAC TAA CCA GAG CAG ACC GCG AGG TAC CTT GTG
 L   E   C   A   W   L   E   I   L   M   I   G   L   V   W   R   S   M   E   H>

1990        2000        2010        2020        2030        2040
CCG GGG AAG CTC CTG TTT GCT CCT AAC TTG CTC CTG GAC AGG AAT CAA GGT AAA TGT GTG
GGC CCC TTC GAG GAC AAA CGA GGA TTG AAC GAG GAC CTG TCC TTA GTT CCA TTT ACA CAC
 P   G   K   L   L   F   A   P   N   L   L   L   D   R   N   Q   G   K   C   V>

2050        2060        2070        2080        2090        2100
GAA GGC ATG GTG GAG ATC TTT GAC ATG TTG CTT GCT ACG TCA AGT CGG TTC CGC ATG ATG
CTT CCG TAC CAC CTC TAG AAA CTG TAC AAC GAA CGA TGC AGT TCA GCC AAG GCG TAC TAC
 E   G   M   V   E   I   F   D   M   L   L   A   T   S   S   R   F   R   M   M>

2110        2120        2130        2140        2150        2160
AAC CTG CAG GGT GAA GAG TTT GTG TGC CTC AAA TCC ATC ATT TTG CTT AAT TCC GGA GTG
TTG GAC GTC CCA CTT CTC AAA CAC ACG GAG TTT AGG TAG TAA AAC GAA TTA AGG CCT CAC
 N   L   Q   G   E   E   F   V   C   L   K   S   I   I   L   L   N   S   G   V>

2170        2180        2190        2200        2210        2220
TAC ACG TTT CTG TCC AGC ACC TTG AAG TCT CTG GAA GAG AAG GAC CAC ATC CAC CGT GTC
ATG TGC AAA GAC AGG TCG TGG AAC TTC AGA GAC CTT CTC TTC CTG GTG TAG GTG GCA CAG
 Y   T   F   L   S   S   T   L   K   S   L   E   E   K   D   H   I   H   R   V>

2230        2240        2250        2260        2270        2280
CTG GAC AAG ATC ACA GAC ACT TTG ATC CAC CTG ATG GCC AAA GCT GGC CTG ACT CTG CAG
GAC CTG TTC TAG TGT CTG TGA AAC TAG GTG GAC TAC CGG TTT CGA CCG GAC TGA GAC GTC
 L   D   K   I   T   D   T   L   I   H   L   M   A   K   A   G   L   T   L   Q>
```

FIG. 10-4

```
      2290        2300        2310        2320        2330        2340
CAG CAG CAT CGC CGC CTA GCT CAG CTC CTT CTC ATT CTT TCC CAT ATC CGG CAC ATG AGT
GTC GTC GTA GCG GCG GAT CGA GTC GAG GAA GAG TAA GAA AGG GTA TAG GCC GTG TAC TCA
 Q   Q   H   R   R   L   A   Q   L   L   L   I   L   S   H   I   R   H   M   S>

2350        2360        2370        2380        2390        2400
AAC AAA GGC ATG GAG CAT CTC TAC AAC ATG AAA TGC AAG AAC GTT GTG CCC CTC TAT GAC
TTG TTT CCG TAC CTC GTA GAG ATG TTG TAC TTT ACG TTC TTG CAA CAC GGG GAG ATA CTG
 N   K   G   M   E   H   L   Y   N   M   K   C   K   N   V   V   P   L   Y   D>

2410        2420        2430        2440        2450        2460
CTG CTC CTG GAG ATG TTG GAT GCC CAC CGC CTT CAT GCC CCA GCC AGT CGC ATG GGA GTG
GAC GAG GAC CTC TAC AAC CTA CGG GTG GCG GAA GTA CGG GGT CGG TCA GCG TAC CCT CAC
 L   L   L   E   M   L   D   A   H   R   L   H   A   P   A   S   R   M   G   V>

2470        2480        2490        2500        2510        2520
CCC CCA GAG GAG CCC AGC CAG ACC CAG CTG GCC ACC ACC AGC TCC ACT TCA GCA CAT TCC
GGG GGT CTC CTC GGG TCG GTC TGG GTC GAC CGG TGG TGG TCG AGG TGA AGT CGT GTA AGG
 P   P   E   E   P   S   Q   T   Q   L   A   T   T   S   S   T   S   A   H   S>

2530        2540        2550        2560        2570        2580
TTA CAA ACC TAC TAC ATA CCC CCG GAA GCA GAG GGC TTC CCC AAC ACG ATC GGG CGC GCC
AAT GTT TGG ATG ATG TAT GGG GGC CTT CGT CTC CCG AAG GGG TTG TGC TAG CCC GCG CGG
 L   Q   T   Y   Y   I   P   P   E   A   E   G   F   P   N   T   I   G   R   A>

2590        2600        2610        2620        2630        2640
GAC GCG CTG GAC GAT TTC GAT CTC GAC ATG CTG GGT TCT GAT GCC CTC GAT GAC TTT GAC
CTG CGC GAC CTG CTA AAG CTA GAG CTG TAC GAC CCA AGA CTA CGG GAG CTA CTG AAA CTG
 D   A   L   D   D   F   D   L   D   M   L   G   S   D   A   L   D   D   F   D>

2650        2660        2670        2680        2690        2700
CTG GAT ATG TTG GGA AGC GAC GCA TTG GAT GAC TTT GAT CTG GAC ATG CTC GGC TCC GAT
GAC CTA TAC AAC CCT TCG CTG CGT AAC CTA CTG AAA CTA GAC CTG TAC GAG CCG AGG CTA
 L   D   M   L   G   S   D   A   L   D   D   F   D   L   D   M   L   G   S   D>

2710        2720        2730  PacI  2740        2750        2760
GCT CTG GAC GAT TTC GAT CTC GAT ATG TTA ATT AAC TAC CCG TAC GAC GTT CCG GAC TAC
CGA GAC CTG CTA AAG CTA GAG CTA TAC AAT TAA TTG ATG GGC ATG CTG CAA GGC CTG ATG
 A   L   D   D   F   D   L   D   M   L   I   N   Y   P   Y   D   V   P   D   Y>

2770
GCT TCT TGA GAA TTC
CGA AGA ACT CTT AAG
 A   S   *   E   F>
```

SEQUENCE LISTING

```
<160> NUMBER OF SEQ ID NOS: 53

<210> SEQ ID NO 1
<211> LENGTH: 58
<212> TYPE: DNA
<213> ORGANISM: Unknown
<220> FEATURE:
<223> OTHER INFORMATION: Synthesized
<220> FEATURE:
<221> NAME/KEY: misc_feature
<222> LOCATION: 19-23
<223> OTHER INFORMATION: Some or all may be missing

<400> SEQUENCE: 1
gagggtaccg cgtgggcgaa aaagcgtggg cgagtcgact ctagagggta tataatgg      58

<210> SEQ ID NO 2
<211> LENGTH: 58
<212> TYPE: DNA
<213> ORGANISM: Unknown
<220> FEATURE:
<223> OTHER INFORMATION: Synthesized
<220> FEATURE:
```

```
<221> NAME/KEY: misc_feature
<222> LOCATION: 19-23
<223> OTHER INFORMATION: Some or all may be missing

<400> SEQUENCE: 2
gagggtaccg cgtgggcgaa aaacgcccac gcagtcgact ctagagggta tataatgg        58

<210> SEQ ID NO 3
<211> LENGTH: 58
<212> TYPE: DNA
<213> ORGANISM: Unknown
<220> FEATURE:
<223> OTHER INFORMATION: Synthesized
<220> FEATURE:
<221> NAME/KEY: misc_feature
<222> LOCATION: 19-23
<223> OTHER INFORMATION: Some or all may be missing

<400> SEQUENCE: 3
gagggtaccc gcccacgcaa aaagcgtggg cgagtcgact ctagagggta tataatgg        58

<210> SEQ ID NO 4
<211> LENGTH: 22
<212> TYPE: DNA
<213> ORGANISM: Unknown
<220> FEATURE:
<223> OTHER INFORMATION: Synthesized

<400> SEQUENCE: 4
ctttatgttt ttggcgtctt cc                                               22

<210> SEQ ID NO 5
<211> LENGTH: 63
<212> TYPE: DNA
<213> ORGANISM: Unknown
<220> FEATURE:
<223> OTHER INFORMATION: Synthesized

<400> SEQUENCE: 5
gaggaggagg aggctagcgc caccatgggg cgcgccggcg ctcccccgac cgatgtcagc      60
ctg                                                                    63

<210> SEQ ID NO 6
<211> LENGTH: 55
<212> TYPE: DNA
<213> ORGANISM: Unknown
<220> FEATURE:
<223> OTHER INFORMATION: Synthesized

<400> SEQUENCE: 6
gaggaggagg agaagcttgt taattaaacc gtactcgtca attccaaggg catcg           55

<210> SEQ ID NO 7
<211> LENGTH: 76
<212> TYPE: DNA
<213> ORGANISM: Unknown
<220> FEATURE:
<223> OTHER INFORMATION: Synthesized

<400> SEQUENCE: 7
gaggaggagg agaagcttaa ctttgcgttt cttttttcggg ttaattaaac cgtactcgtc     60
aattccaagg gcatcg                                                      76

<210> SEQ ID NO 8
<211> LENGTH: 47
```

```
<212> TYPE: DNA
<213> ORGANISM: Unknown
<220> FEATURE:
<223> OTHER INFORMATION: Synthesized

<400> SEQUENCE: 8
gaggaggagg agaagcttgg ggccacggcg gccctcgagc cctatgc                47

<210> SEQ ID NO 9
<211> LENGTH: 44
<212> TYPE: DNA
<213> ORGANISM: Unknown
<220> FEATURE:
<223> OTHER INFORMATION: Synthesized

<400> SEQUENCE: 9
gaggagggat cccctggcc ggcctggcca ctagttctag agtc                    44

<210> SEQ ID NO 10
<211> LENGTH: 65
<212> TYPE: DNA
<213> ORGANISM: Unknown
<220> FEATURE:
<223> OTHER INFORMATION: Synthesized

<400> SEQUENCE: 10
gaggagggat ccccaacttt gcgtttcttt ttcggctggc cggcctggcc actagttcta   60
gagtc                                                              65

<210> SEQ ID NO 11
<211> LENGTH: 47
<212> TYPE: DNA
<213> ORGANISM: Unknown
<220> FEATURE:
<223> OTHER INFORMATION: Synthesized

<400> SEQUENCE: 11
gaggaggagg agggatccag tcagagttgt gagagcactg gatgctg                47

<210> SEQ ID NO 12
<211> LENGTH: 48
<212> TYPE: DNA
<213> ORGANISM: Unknown
<220> FEATURE:
<223> OTHER INFORMATION: Synthesized

<400> SEQUENCE: 12
gaggaggaat tctcaagcaa taacttcaga catcatttct ggaaattc                48

<210> SEQ ID NO 13
<211> LENGTH: 60
<212> TYPE: DNA
<213> ORGANISM: Unknown
<220> FEATURE:
<223> OTHER INFORMATION: Synthesized

<400> SEQUENCE: 13
gaggaggagg aggagggccg gccgcgtcga ccaggtcaga gttgtgagag cactggatgc   60

<210> SEQ ID NO 14
<211> LENGTH: 60
<212> TYPE: DNA
<213> ORGANISM: Unknown
<220> FEATURE:
<223> OTHER INFORMATION: Synthesized
```

```
<400> SEQUENCE: 14
gaggaggagg aggagggcgc gccccgtcga cccagcaata acttcagaca tcatttctgg    60

<210> SEQ ID NO 15
<211> LENGTH: 52
<212> TYPE: DNA
<213> ORGANISM: Unknown
<220> FEATURE:
<223> OTHER INFORMATION: Synthesized

<400> SEQUENCE: 15
gaggaggagg aggagggccg gccgccgaaa tgaaatgggt gcttcaggag ac            52

<210> SEQ ID NO 16
<211> LENGTH: 51
<212> TYPE: DNA
<213> ORGANISM: Unknown
<220> FEATURE:
<223> OTHER INFORMATION: Synthesized

<400> SEQUENCE: 16
gaggaggagg aggagggcgc gcccgatcgt gttggggaag ccctctgctt c             51

<210> SEQ ID NO 17
<211> LENGTH: 50
<212> TYPE: DNA
<213> ORGANISM: Unknown
<220> FEATURE:
<223> OTHER INFORMATION: Synthesized

<400> SEQUENCE: 17
gaggaggagg aggagttaat taagatcgtg ttggggaagc cctctgcttc               50

<210> SEQ ID NO 18
<211> LENGTH: 54
<212> TYPE: DNA
<213> ORGANISM: Unknown
<220> FEATURE:
<223> OTHER INFORMATION: Synthesized

<400> SEQUENCE: 18
gaggaggagg agggatccgc caccatgcga aatgaaatgg gtgcttcagg agac          54

<210> SEQ ID NO 19
<211> LENGTH: 90
<212> TYPE: DNA
<213> ORGANISM: Unknown
<220> FEATURE:
<223> OTHER INFORMATION: Synthesized

<400> SEQUENCE: 19
gaggaggagg aggaggagac tagtggaacc acccccacca ccgcccgagc caccgccacc    60
agaggagatc gtgttgggga agccctctgc                                    90

<210> SEQ ID NO 20
<211> LENGTH: 90
<212> TYPE: DNA
<213> ORGANISM: Unknown
<220> FEATURE:
<223> OTHER INFORMATION: Synthesized

<400> SEQUENCE: 20
gaggaggagg aggaggaggc tagcggcggt ggcggtggct cctctggtgg cggtggcggt    60
tcttccaatg aaatgggtgc ttcaggagac                                    90
```

<210> SEQ ID NO 21
<211> LENGTH: 54
<212> TYPE: DNA
<213> ORGANISM: Unknown
<220> FEATURE:
<223> OTHER INFORMATION: Synthesized

<400> SEQUENCE: 21
gaggaggagg aggaggaggc tagctcttcc aatgaaatgg gtgcttcagg agac        54

<210> SEQ ID NO 22
<211> LENGTH: 41
<212> TYPE: DNA
<213> ORGANISM: Unknown
<220> FEATURE:
<223> OTHER INFORMATION: Synthesized

<400> SEQUENCE: 22
gaggaggagg gccggccggg aagccgtgca ggaggagcgg c                      41

<210> SEQ ID NO 23
<211> LENGTH: 88
<212> TYPE: DNA
<213> ORGANISM: Unknown
<220> FEATURE:
<223> OTHER INFORMATION: Synthesized

<400> SEQUENCE: 23
gaggaggagg aggagactag tggaaccacc cccaccaccg cccgagccac cgccaccaga  60
ggaagtcatt tggtgcggcg cctccagc                                    88

<210> SEQ ID NO 24
<211> LENGTH: 52
<212> TYPE: DNA
<213> ORGANISM: Unknown
<220> FEATURE:
<223> OTHER INFORMATION: Synthesized

<400> SEQUENCE: 24
gaggaggagg aggctagctc ttccggtggc ggccaagact tgttaagaa gg           52

<210> SEQ ID NO 25
<211> LENGTH: 88
<212> TYPE: DNA
<213> ORGANISM: Unknown
<220> FEATURE:
<223> OTHER INFORMATION: Synthesized

<400> SEQUENCE: 25
gaggaggagg aggctagcgg cggtggcggt ggctcctctg gtggcggtgg cggttcttcc  60
ggtggcggcc aagactttgt taagaagg                                    88

<210> SEQ ID NO 26
<211> LENGTH: 45
<212> TYPE: DNA
<213> ORGANISM: Unknown
<220> FEATURE:
<223> OTHER INFORMATION: Synthesized

<400> SEQUENCE: 26
gaggaggagg gcgcgcccgg catgaacgtc ccagatctcc tcgag                  45

<210> SEQ ID NO 27

```
<211> LENGTH: 68
<212> TYPE: DNA
<213> ORGANISM: Unknown
<220> FEATURE:
<223> OTHER INFORMATION: Synthesized

<400> SEQUENCE: 27
gaggaggagg aggagactag tagagccacc gccccttca gaaccgcccg agccaccgcc    60
accagagg                                                           68

<210> SEQ ID NO 28
<211> LENGTH: 72
<212> TYPE: DNA
<213> ORGANISM: Unknown
<220> FEATURE:
<223> OTHER INFORMATION: Synthesized

<400> SEQUENCE: 28
gaggaggagg aggctagcgg gggttcggag ggtggcgggt ctgagggtgg gggtggttcc    60
actagctctt cc                                                       72

<210> SEQ ID NO 29
<211> LENGTH: 18
<212> TYPE: DNA
<213> ORGANISM: Unknown
<220> FEATURE:
<223> OTHER INFORMATION: Synthesized

<400> SEQUENCE: 29
ggggccggag ccgcagtg                                                 18

<210> SEQ ID NO 30
<211> LENGTH: 7
<212> TYPE: PRT
<213> ORGANISM: Unknown
<220> FEATURE:
<223> OTHER INFORMATION: Synthesized

<400> SEQUENCE: 30

Pro Lys Lys Lys Arg Lys Val
 1               5

<210> SEQ ID NO 31
<211> LENGTH: 558
<212> TYPE: DNA
<213> ORGANISM: Unknown
<220> FEATURE:
<223> OTHER INFORMATION: Synthesized
<220> FEATURE:
<221> NAME/KEY: misc_feature
<222> LOCATION: 1, 2, 557, 558
<223> OTHER INFORMATION: n = A,T,C or G

<400> SEQUENCE: 31
nnggcccagg cggccctcga gcccggggag aagccctatg cttgtccgga atgtggtaag    60
tccttcagtc gcagcgatgt gctggtgcgc caccagcgta cccacacggg tgaaaaaccg   120
tataaatgcc cagagtgcgg caaatctttt agccgcagcg atgatctggt tcgccatcaa   180
cgcactcata ctggcgagaa gccatacaaa tgtccagaat gtggcaagtc tttctcccag   240
tctagccacc tggttcgcca ccaacgtact cacaccgggg agaagcccta tgcttgtccg   300
gaatgtggta agtccttcag ccgcagcgat aacctggtgc gccaccagcg tacccacacg   360
ggtgaaaaac cgtataaatg cccagagtgc ggcaaatctt ttagccaggc cggccacctg   420
```

| gccagccatc aacgcactca tactggcgag aagccataca aatgtccaga atgtggcaag | 480 |
| tctttcagtg attgtcgtga tcttgcgagg caccaacgta ctcacaccgg taaaaaaact | 540 |
| agtggccagg ccggccnn | 558 |

<210> SEQ ID NO 32
<211> LENGTH: 186
<212> TYPE: PRT
<213> ORGANISM: Unknown
<220> FEATURE:
<223> OTHER INFORMATION: Synthesized
<220> FEATURE:
<221> NAME/KEY: VARIANT
<222> LOCATION: 1, 186
<223> OTHER INFORMATION: Xaa = Any Amino Acid

<400> SEQUENCE: 32

Xaa Ala Gln Ala Ala Leu Glu Pro Gly Glu Lys Pro Tyr Ala Cys Pro
 1               5                  10                  15
Glu Cys Gly Lys Ser Phe Ser Arg Ser Asp Val Leu Val Arg His Gln
             20                  25                  30
Arg Thr His Thr Gly Glu Lys Pro Tyr Lys Cys Pro Glu Cys Gly Lys
         35                  40                  45
Ser Phe Ser Arg Ser Asp Asp Leu Val Arg His Gln Arg Thr His Thr
     50                  55                  60
Gly Glu Lys Pro Tyr Lys Cys Pro Glu Cys Gly Lys Ser Phe Ser Gln
 65                  70                  75                  80
Ser Ser His Leu Val Arg His Gln Arg Thr His Thr Gly Glu Lys Pro
                 85                  90                  95
Tyr Ala Cys Pro Glu Cys Gly Lys Ser Phe Ser Arg Ser Asp Asn Leu
            100                 105                 110
Val Arg His Gln Arg Thr His Thr Gly Glu Lys Pro Tyr Lys Cys Pro
        115                 120                 125
Glu Cys Gly Lys Ser Phe Ser Gln Ala Gly His Leu Ala Ser His Gln
    130                 135                 140
Arg Thr His Thr Gly Glu Lys Pro Tyr Lys Cys Pro Glu Cys Gly Lys
145                 150                 155                 160
Ser Phe Ser Asp Cys Arg Asp Leu Ala Arg His Gln Arg Thr His Thr
                165                 170                 175
Gly Lys Lys Thr Ser Gly Gln Ala Gly Xaa
            180                 185

<210> SEQ ID NO 33
<211> LENGTH: 567
<212> TYPE: DNA
<213> ORGANISM: Unknown
<220> FEATURE:
<223> OTHER INFORMATION: Synthesized
<220> FEATURE:
<221> NAME/KEY: misc_feature
<222> LOCATION: 1, 2, 566, 567
<223> OTHER INFORMATION: n = A,T,C or G

<400> SEQUENCE: 33

| nnggcccagg cggccctcga gccctatgct tgccctgtcg agtcctgcga tcgccgcttt | 60 |
| tctaagtcgg ctgatctgaa gcgccatatc cgcatccaca caggccagaa gcccttccag | 120 |
| tgtcgaatat gcatgcgtaa cttcagtcgt agtgaccacc ttaccaccca catccgcacc | 180 |
| cacacaggcg agaagccttt tgcctgtgac atttgtggga ggaagtttgc caggagtgat | 240 |
| gaacgcaaga ggcataccaa aatccatacc ggtgagaagc cctatgcttg ccctgtcgag | 300 |

```
tcctgcgatc gccgcttttc taagtcggct gatctgaagc gccatatccg catccacaca    360
ggccagaagc ccttccagtg tcgaatatgc atgcgtaact tcagtcgtag tgaccacctt    420
accacccaca tccgcaccca cacaggcgag aagccttttg cctgtgacat ttgtgggagg    480
aagtttgcca ggagtgatga acgcaagagg cataccaaaa tccatttaag acagaaggac    540
tctagaacta gtggccaggc cggccnn                                        567
```

```
<210> SEQ ID NO 34
<211> LENGTH: 189
<212> TYPE: PRT
<213> ORGANISM: Unknown
<220> FEATURE:
<223> OTHER INFORMATION: Synthesized
<220> FEATURE:
<221> NAME/KEY: VARIANT
<222> LOCATION: 1, 189
<223> OTHER INFORMATION: Xaa = Any Amino Acid

<400> SEQUENCE: 34

Xaa Ala Gln Ala Ala Leu Glu Pro Tyr Ala Cys Pro Val Glu Ser Cys
 1               5                  10                  15

Asp Arg Arg Phe Ser Lys Ser Ala Asp Leu Lys Arg His Ile Arg Ile
            20                  25                  30

His Thr Gly Gln Lys Pro Phe Gln Cys Arg Ile Cys Met Arg Asn Phe
        35                  40                  45

Ser Arg Ser Asp His Leu Thr Thr His Ile Arg Thr His Thr Gly Glu
    50                  55                  60

Lys Pro Phe Ala Cys Asp Ile Cys Gly Arg Lys Phe Ala Arg Ser Asp
65                  70                  75                  80

Glu Arg Lys Arg His Thr Lys Ile His Thr Gly Glu Lys Pro Tyr Ala
                85                  90                  95

Cys Pro Val Glu Ser Cys Asp Arg Arg Phe Ser Lys Ser Ala Asp Leu
            100                 105                 110

Lys Arg His Ile Arg Ile His Thr Gly Gln Lys Pro Phe Gln Cys Arg
        115                 120                 125

Ile Cys Met Arg Asn Phe Ser Arg Ser Asp His Leu Thr Thr His Ile
    130                 135                 140

Arg Thr His Thr Gly Glu Lys Pro Phe Ala Cys Asp Ile Cys Gly Arg
145                 150                 155                 160

Lys Phe Ala Arg Ser Asp Glu Arg Lys Arg His Thr Lys Ile His Leu
                165                 170                 175

Arg Gln Lys Asp Ser Arg Thr Ser Gly Gln Ala Gly Xaa
            180                 185
```

```
<210> SEQ ID NO 35
<211> LENGTH: 558
<212> TYPE: DNA
<213> ORGANISM: Unknown
<220> FEATURE:
<223> OTHER INFORMATION: Synthesized
<220> FEATURE:
<221> NAME/KEY: misc_feature
<222> LOCATION: 1, 2, 557, 558
<223> OTHER INFORMATION: n = A,T,C or G

<400> SEQUENCE: 35
nnggcccagg cggccctcga gcccggggag aagccctatg cttgtccgga atgtggtaag     60
tccttcagca ccagtggcca cctggtgcgc caccagcgta cccacacggg tgaaaaaccg    120
```

-continued

```
tataaatgcc cagagtgcgg caaatctttt agtcgcagcg atgtgctggt gcgccatcaa    180
cgcactcata ctggcgagaa gccatacaaa tgtccagaat gtggcaagtc tttctcacgt    240
tcagacgact tggtccgtca ccaacgtact cacaccgggg agaagcccta tgcttgtccg    300
gaatgtggta agtccttcag tgatcctggc aacctggttc gccaccagcg tacccacacg    360
ggtgaaaaac cgtataaatg cccagagtgc ggcaaatctt ttagtcgctc cgataaactg    420
gtgcgccatc aacgcactca tactggcgag aagccataca aatgtccaga atgtggcaag    480
tctttctccc agtctagcca cctggttcgc caccaacgta ctcacaccgg taaaaaaact    540
agtggccagg ccggccnn                                                 558
```

<210> SEQ ID NO 36
<211> LENGTH: 186
<212> TYPE: PRT
<213> ORGANISM: Unknown
<220> FEATURE:
<223> OTHER INFORMATION: Synthesized
<220> FEATURE:
<221> NAME/KEY: VARIANT
<222> LOCATION: 1, 186
<223> OTHER INFORMATION: Xaa = Any Amino Acid

<400> SEQUENCE: 36

Xaa Ala Gln Ala Ala Leu Glu Pro Gly Glu Lys Pro Tyr Ala Cys Pro
1               5                   10                  15

Glu Cys Gly Lys Ser Phe Ser Thr Ser Gly His Leu Val Arg His Gln
            20                  25                  30

Arg Thr His Thr Gly Glu Lys Pro Tyr Lys Cys Pro Glu Cys Gly Lys
        35                  40                  45

Ser Phe Ser Arg Ser Asp Val Leu Val Arg His Gln Arg Thr His Thr
    50                  55                  60

Gly Glu Lys Pro Tyr Lys Cys Pro Glu Cys Gly Lys Ser Phe Ser Arg
65                  70                  75                  80

Ser Asp Asp Leu Val Arg His Gln Arg Thr His Thr Gly Glu Lys Pro
                85                  90                  95

Tyr Ala Cys Pro Glu Cys Gly Lys Ser Phe Ser Asp Pro Gly Asn Leu
            100                 105                 110

Val Arg His Gln Arg Thr His Thr Gly Glu Lys Pro Tyr Lys Cys Pro
        115                 120                 125

Glu Cys Gly Lys Ser Phe Ser Arg Ser Asp Lys Leu Val Arg His Gln
    130                 135                 140

Arg Thr His Thr Gly Glu Lys Pro Tyr Lys Cys Pro Glu Cys Gly Lys
145                 150                 155                 160

Ser Phe Ser Gln Ser Ser His Leu Val Arg His Gln Arg Thr His Thr
                165                 170                 175

Gly Lys Lys Thr Ser Gly Gln Ala Gly Xaa
            180                 185

<210> SEQ ID NO 37
<211> LENGTH: 303
<212> TYPE: DNA
<213> ORGANISM: Unknown
<220> FEATURE:
<223> OTHER INFORMATION: Synthesized

<400> SEQUENCE: 37

```
gggcgcgccc aggaaactat gaccttcaaa gacgttgaag ttaccttctc tcaggacgaa    60
tggggttggc tggactccgc tcagcgtaac ctgtaccgtg acgttatgct ggaaaactac    120
```

```
cgcaacatgg cttccctggt tggcggcggc cgcggtggtc aggaaactat gaccttcaaa    180
gacgttgaag ttaccttctc tcaggacgaa tggggttggc tggactccgc tcagcgtaac    240
ctgtaccgtg acgttatgct ggaaaactac cgcaacatgg cttccctggt tggcttaatt    300
aac                                                                  303
```

```
<210> SEQ ID NO 38
<211> LENGTH: 240
<212> TYPE: DNA
<213> ORGANISM: Unknown
<220> FEATURE:
<223> OTHER INFORMATION: Synthesized

<400> SEQUENCE: 38
gggcgcgccg ctgccgtgcg catgaacatc cagatgctgc tcgaagccgc tgattatctg     60
gaacgccggg agcgcgaagc cgagcacggc tacgccagca tgctgccata tggcggccgc    120
ggtggtgccg ctgccgtgcg catgaacatc cagatgctgc tcgaagccgc tgattatctg    180
gaacgccggg agcgcgaagc cgagcacggc tacgccagca tgctgccata tttaattaac    240
```

```
<210> SEQ ID NO 39
<211> LENGTH: 2739
<212> TYPE: DNA
<213> ORGANISM: Unknown
<220> FEATURE:
<223> OTHER INFORMATION: Synthesized

<400> SEQUENCE: 39
ggatccgcca ccatgggcca ggcggccctc gagcccgggg agaagcccta tgcttgtccg     60
gaatgtggta agtccttcag taggaaggat tcgcttgtga ggcaccagcg tacccacacg    120
ggtgaaaaac cgtataaatg cccagagtgc ggcaaatctt ttagtcagtc ggggatctt    180 aggcgtcatc aacgcactca tactggcgag aagcctataca aatgtccaga atgtggcaag    240
tctttcagtg attgtcgtga tcttgcgagg caccaacgta tcacaccgg ggagaagccc    300 tatgcttgtc cggaatgtgg taagtccttc tctcagagct ctcacctggt gcgccaccag    360
cgtacccaca cgggtgaaaa accgtataaa tgcccagagt gcggcaaatc ttttagtgac    420
tgccgcgacc ttgctcgcca tcaacgcact catactggcg agaagccata caaatgtcca    480
gaatgtggca agtctttcag ccgctctgac aagctggtgc gtcaccaacg tactcacacc    540
ggtaaaaaaa ctagtggcca ggccggccgc cgaaatgaaa tgggtgcttc aggagacatg    600
agggctgcca acctttggcc aagccctctt gtgattaagc acactaagaa gaatagccct    660
gccttgtcct tgacagctga ccagatggtc agtgccttgt tggatgctga accgcccatg    720
atctattctg aatatgatcc ttctagaccc ttcagtgaag cctcaatgat gggcttattg    780
accaacctag cagataggga gctggttcat atgatcaact gggcaaagag agtgccaggc    840 tttgggggact tgaatctcca tgatcaggtc caccttctcg agtgtgcctg gctggagatt    900
ctgatgattg tctcgtctg cgcgctccat ggaacacccgg ggaagctcct gttttgctcct    960 aacttgctcc tggacaggaa tcaaggtaaa tgtgtggaag catggtgga gatctttgac    1020 atgttgcttg ctacgtcaag tcggttccgc atgatgaacc tgcagggtga agagtttgtg    1080
tgcctcaaat ccatcatttt gcttaattcc ggagtgtaca cgtttctgtc cagcaccttg    1140
aagtctctgg aagagaagga ccacatccac cgtgtcctgg acaagatcac agacactttg    1200
atccacctga tggccaaagc tggcctgact ctgcagcagc agcatcgccg cctagctcag    1260
```

```
ctccttctca ttctttccca tatccggcac atgagtaaca aaggcatgga gcatctctac    1320
aacatgaaat gcaagaacgt tgtgcccctc tatgacctgc tcctggagat gttggatgcc    1380
caccgccttc atgccccagc cagtcgcatg ggagtgcccc cagaggagcc cagccagacc    1440
cagctggcca ccaccagctc cacttcagca cattccttac aaacctacta catacccccg    1500
gaagcagagg gcttccccaa cacgatctcc tctggtggcg gtggctcggg cggtggtggg    1560
ggtggttcca ctagctcttc caatgaaatg ggtgcttcag agacatgag ggctgccaac     1620
ctttggccaa gccctcttgt gattaagcac actaagaaga atagccctgc cttgtccttg    1680
acagctgacc agatggtcag tgccttgttg atgctgaac cgcccatgat ctattctgaa     1740
tatgatcctt ctagacccct cagtgaagcc tcaatgatgg gcttattgac caacctagca    1800
gatagggagc tggttcatat gatcaactgg gcaaagagag tgccaggctt tggggacttg    1860
aatctccatg atcaggtcca ccttctcgag tgtgcctggc tggagattct gatgattggt    1920
ctcgtctggc gctccatgga cacccgggg aagctcctgt tgctcctaa cttgctcctg       1980
gacaggaatc aaggtaaatg tgtggaaggc atggtggaga tctttgacat gttgcttgct    2040
acgtcaagtc ggttccgcat gatgaacctg cagggtgaag agtttgtgtg cctcaaatcc    2100
atcattttgc ttaattccgg agtgtacacg tttctgtcca gcaccttgaa gtctctggaa    2160
gagaaggacc acatccaccg tgtcctggac aagatcacag acactttgat ccacctgatg    2220
gccaaagctg gcctgactct gcagcagcag catcgccgcc tagctcagct ccttctcatt    2280
ctttcccata tccggcacat gagtaacaaa ggcatggagc atctctacaa catgaaatgc    2340
aagaacgttg tgcccctcta tgacctgctc ctggagatgt tggatgccca ccgccttcat    2400
gcccagcca gtcgcatggg agtgcccccca gaggagccca gccagaccca gctggccacc    2460
accagctcca cttcagcaca ttccttacaa acctactaca taccccccgga agcagagggc   2520
ttccccaaca cgatcgggcg cgccgacgcg ctggacgatt cgatctcga catgctgggt    2580
tctgatgccc tcgatgactt tgacctggat atgttgggaa gcgacgcatt ggatgacttt    2640
gatctggaca tgctcggctc cgatgctctg gacgatttcg atctcgatat gttaattaac    2700
tacccgtacg acgttccgga ctacgcttct tgagaattc                           2739
```

<210> SEQ ID NO 40
<211> LENGTH: 910
<212> TYPE: PRT
<213> ORGANISM: Unknown
<220> FEATURE:
<223> OTHER INFORMATION: Synthesized

<400> SEQUENCE: 40

```
Gly Ser Ala Thr Met Ala Gln Ala Ala Leu Glu Pro Gly Glu Lys Pro
 1               5                  10                  15

Tyr Ala Cys Pro Glu Cys Gly Lys Ser Phe Ser Arg Lys Asp Ser Leu
            20                  25                  30

Val Arg His Gln Arg Thr His Thr Gly Glu Lys Pro Tyr Lys Cys Pro
        35                  40                  45

Glu Cys Gly Lys Ser Phe Ser Gln Ser Gly Asp Leu Arg Arg His Gln
    50                  55                  60

Arg Thr His Thr Gly Glu Lys Pro Tyr Lys Cys Pro Glu Cys Gly Lys
65                  70                  75                  80

Ser Phe Ser Asp Cys Arg Asp Leu Ala Arg His Gln Arg Thr His Thr
                85                  90                  95

Gly Glu Lys Pro Tyr Ala Cys Pro Glu Cys Gly Lys Ser Phe Ser Gln
```

-continued

```
                100                 105                 110
Ser Ser His Leu Val Arg His Gln Arg Thr His Thr Gly Glu Lys Pro
        115                 120                 125
Tyr Lys Cys Pro Glu Cys Gly Lys Ser Phe Ser Asp Cys Arg Asp Leu
        130                 135             140
Ala Arg His Gln Arg Thr His Thr Gly Glu Lys Pro Tyr Lys Cys Pro
145                 150                 155                 160
Glu Cys Gly Lys Ser Phe Ser Arg Ser Asp Lys Leu Val Arg His Gln
                165                 170                 175
Arg Thr His Thr Gly Lys Lys Thr Ser Gly Gln Ala Gly Arg Arg Asn
            180                 185                 190
Glu Met Gly Ala Ser Gly Asp Met Arg Ala Ala Asn Leu Trp Pro Ser
        195                 200                 205
Pro Leu Val Ile Lys His Thr Lys Lys Asn Ser Pro Ala Leu Ser Leu
        210                 215                 220
Thr Ala Asp Gln Met Val Ser Ala Leu Leu Asp Ala Glu Pro Pro Met
225                 230                 235                 240
Ile Tyr Ser Glu Tyr Asp Pro Ser Arg Pro Phe Ser Glu Ala Ser Met
                245                 250                 255
Met Gly Leu Leu Thr Asn Leu Ala Asp Arg Glu Leu Val His Met Ile
                260                 265                 270
Asn Trp Ala Lys Arg Val Pro Gly Phe Gly Asp Leu Asn Leu His Asp
        275                 280                 285
Gln Val His Leu Leu Glu Cys Ala Trp Leu Glu Ile Leu Met Ile Gly
    290                 295                 300
Leu Val Trp Arg Ser Met Glu His Pro Gly Lys Leu Leu Phe Ala Pro
305                 310                 315                 320
Asn Leu Leu Asp Arg Asn Gln Gly Lys Cys Val Glu Gly Met Val
                325                 330                 335
Glu Ile Phe Asp Met Leu Leu Ala Thr Ser Ser Arg Phe Arg Met Met
            340                 345                 350
Asn Leu Gln Gly Glu Glu Phe Val Cys Leu Lys Ser Ile Ile Leu Leu
        355                 360                 365
Asn Ser Gly Val Tyr Thr Phe Leu Ser Ser Thr Leu Lys Ser Leu Glu
    370                 375                 380
Glu Lys Asp His Ile His Arg Val Leu Asp Lys Ile Thr Asp Thr Leu
385                 390                 395                 400
Ile His Leu Met Ala Lys Ala Gly Leu Thr Leu Gln Gln Gln His Arg
                405                 410                 415
Arg Leu Ala Gln Leu Leu Leu Ile Leu Ser His Ile Arg His Met Ser
            420                 425                 430
Asn Lys Gly Met Glu His Leu Tyr Asn Met Lys Cys Lys Asn Val Val
        435                 440                 445
Pro Leu Tyr Asp Leu Leu Leu Glu Met Leu Asp Ala His Arg Leu His
        450                 455                 460
Ala Pro Ala Ser Arg Met Gly Val Pro Pro Glu Glu Pro Ser Gln Thr
465                 470                 475                 480
Gln Leu Ala Thr Thr Ser Ser Thr Ser Ala His Ser Leu Gln Thr Tyr
                485                 490                 495
Tyr Ile Pro Pro Glu Ala Glu Gly Phe Pro Asn Thr Ile Ser Ser Gly
            500                 505                 510
Gly Gly Gly Ser Gly Gly Gly Gly Gly Ser Thr Ser Ser Ser Asn
        515                 520                 525
```

```
Glu Met Gly Ala Ser Gly Asp Met Arg Ala Ala Asn Leu Trp Pro Ser
    530                 535                 540

Pro Leu Val Ile Lys His Thr Lys Lys Asn Ser Pro Ala Leu Ser Leu
545                 550                 555                 560

Thr Ala Asp Gln Met Val Ser Ala Leu Leu Asp Ala Glu Pro Pro Met
                565                 570                 575

Ile Tyr Ser Glu Tyr Asp Pro Ser Arg Pro Phe Ser Glu Ala Ser Met
                580                 585                 590

Met Gly Leu Leu Thr Asn Leu Ala Asp Arg Glu Leu Val His Met Ile
            595                 600                 605

Asn Trp Ala Lys Arg Val Pro Gly Phe Gly Asp Leu Asn Leu His Asp
        610                 615                 620

Gln Val His Leu Leu Glu Cys Ala Trp Leu Glu Ile Leu Met Ile Gly
625                 630                 635                 640

Leu Val Trp Arg Ser Met Glu His Pro Gly Lys Leu Leu Phe Ala Pro
                645                 650                 655

Asn Leu Leu Leu Asp Arg Asn Gln Gly Lys Cys Val Glu Gly Met Val
                660                 665                 670

Glu Ile Phe Asp Met Leu Leu Ala Thr Ser Ser Arg Phe Arg Met Met
            675                 680                 685

Asn Leu Gln Gly Glu Glu Phe Val Cys Leu Lys Ser Ile Ile Leu Leu
        690                 695                 700

Asn Ser Gly Val Tyr Thr Phe Leu Ser Ser Thr Leu Lys Ser Leu Glu
705                 710                 715                 720

Glu Lys Asp His Ile His Arg Val Leu Asp Lys Ile Thr Asp Thr Leu
                725                 730                 735

Ile His Leu Met Ala Lys Ala Gly Leu Thr Leu Gln Gln Gln His Arg
            740                 745                 750

Arg Leu Ala Gln Leu Leu Leu Ile Leu Ser His Ile Arg His Met Ser
        755                 760                 765

Asn Lys Gly Met Glu His Leu Tyr Asn Met Lys Cys Lys Asn Val Val
770                 775                 780

Pro Leu Tyr Asp Leu Leu Leu Glu Met Leu Asp Ala His Arg Leu His
785                 790                 795                 800

Ala Pro Ala Ser Arg Met Gly Val Pro Pro Glu Glu Pro Ser Gln Thr
                805                 810                 815

Gln Leu Ala Thr Thr Ser Ser Thr Ser Ala His Ser Leu Gln Thr Tyr
                820                 825                 830

Tyr Ile Pro Pro Glu Ala Glu Gly Phe Pro Asn Thr Ile Gly Arg Ala
            835                 840                 845

Asp Ala Leu Asp Asp Phe Asp Leu Asp Met Leu Gly Ser Asp Ala Leu
        850                 855                 860

Asp Asp Phe Asp Leu Asp Met Leu Gly Ser Asp Ala Leu Asp Asp Phe
865                 870                 875                 880

Asp Leu Asp Met Leu Gly Ser Asp Ala Leu Asp Asp Phe Asp Leu Asp
                885                 890                 895

Met Leu Ile Asn Tyr Pro Tyr Asp Val Pro Asp Tyr Ala Ser
                900                 905                 910

<210> SEQ ID NO 41
<211> LENGTH: 2775
<212> TYPE: DNA
<213> ORGANISM: Unknown
<220> FEATURE:
```

<223> OTHER INFORMATION: Synthesized

<400> SEQUENCE: 41

```
ggatccgcca ccatggccca ggcggccctc gagcccgggg agaagcccta tgcttgtccg     60
gaatgtggta agtccttcag taggaaggat tcgcttgtga ggcaccagcg tacccacacg    120
ggtgaaaaac cgtataaatg cccagagtgc ggcaaatctt ttagtcagtc gggggatctt    180
aggcgtcatc aacgcactca tactggcgag aagccataca aatgtccaga atgtggcaag    240
tctttcagtg attgtcgtga tcttgcgagg caccaacgta ctcacaccgg ggagaagccc    300
tatgcttgtc cggaatgtgg taagtccttc tctcagagct ctcacctggt gcgccaccag    360
cgtacccaca cgggtgaaaa accgtataaa tgcccagagt gcggcaaatc ttttagtgac    420
tgccgcgacc ttgctcgcca tcaacgcact catactggcg agaagccata caaatgtcca    480
gaatgtggca agtctttcag ccgctctgac aagctggtgc gtcaccaacg tactcacacc    540
ggtaaaaaaa ctagtggcca ggccggccgc cgaaatgaaa tgggtgcttc aggagacatg    600
agggctgcca acctttggcc aagccctctt gtgattaagc acactaagaa gaatagccct    660
gccttgtcct tgacagctga ccagatggtc agtgccttgt tggatgctga accgcccatg    720
atctattctg aatatgatcc ttctagaccc ttcagtgaag cctcaatgat gggcttattg    780
accaacctag cagatagyga gctggttcat atgatcaact gggcaaagag agtgccaggc    840
tttggggact tgaatctcca tgatcaggtc accttctcg agtgtgcctg gctggagatt    900
ctgatgattg tctcgtctg gcgctccatg gaacacccgg ggaagctcct gtttgctcct    960
aacttgctcc tggacaggaa tcaaggtaaa tgtgtggaag gcatggtgga gatctttgac   1020
atgttgcttg ctacgtcaag tcggttccgc atgatgaacc tgcagggtga agagtttgtg   1080
tgcctcaaat ccatcatttt gcttaattcc ggagtgtaca cgtttctgtc cagcaccttg   1140
aagtctctgg aagagaagga ccacatccac cgtgtcctgg acaagatcac agacactttg   1200
atccacctga tggccaaagc tggcctgact ctgcagcagc agcatcgccg cctagctcag   1260
ctccttctca ttctttccca tatccggcac atgagtaaca aaggcatgga gcatctctac   1320
aacatgaaat gcaagaacgt tgtgcccctc tatgacctgc tcctggagat gttggatgcc   1380
caccgccttc atgccccagc cagtcgcatg ggagtgcccc cagaggagcc cagcagacc    1440
cagctggcca ccaccagctc cacttcagca cattccttac aaacctacta catacccccg   1500
gaagcagagg gcttccccaa cacgatctcc tctggtggcg gtggctcggg cggtggtggg   1560
ggtggttcca ctagcggcgg tggcggtggc tcctctggtg gcggtggcgg ttcttccaat   1620
gaaatgggtg cttcaggaga catgagggct gccaaccttt ggccaagccc tcttgtgatt   1680
aagcacacta agaagaatag ccctgccttg tccttgacag ctgaccagat ggtcagtgcc   1740
ttgttggatg ctgaaccgcc catgatctat tctgaatatg atccttctag acccttcagt   1800
gaagcctcaa tgatgggctt attgaccaac ctagcagata gggagctggt tcatatgatc   1860
aactgggcaa agagagtgcc aggctttggg gacttgaatc tccatgatca ggtccacctt   1920
ctcgagtgtg cctggctgga gattctgatg attggtctcg tctggcgctc catgaacac    1980
ccggggaagc tcctgtttgc tcctaacttg ctcctggaca ggaatcaagg taaatgtgtg   2040
gaaggcatgt ggagatcttt gacatgttg cttgctacgt caagtcggtt ccgcatgatg   2100
aacctgcagg gtgaagagtt tgtgtgcctc aaatccatca ttttgcttaa ttccggagtg   2160
tacacgtttc tgtccagcac cttgaagtct ctggaagaga aggaccacat ccaccgtgtc   2220
ctggacaaga tcacagacac tttgatccac ctgatggcca aagctggcct gactctgcag   2280
```

```
cagcagcatc gccgcctagc tcagctcctt ctcattcttt cccatatccg gcacatgagt    2340
aacaaaggca tggagcatct ctacaacatg aaatgcaaga acgttgtgcc cctctatgac    2400
ctgctcctgg agatgttgga tgcccaccgc cttcatgccc cagccagtcg catgggagtg    2460
cccccagagg agcccagcca gacccagctg gccaccacca gctccacttc agcacattcc    2520
ttacaaacct actacatacc cccggaagca gagggcttcc ccaacacgat cgggcgcgcc    2580
gacgcgctgg acgatttcga tctcgacatg ctgggttctg atgccctcga tgactttgac    2640
ctggatatgt tgggaagcga cgcattggat gactttgatc tggacatgct cggctccgat    2700
gctctggacg atttcgatct cgatatgtta attaactacc cgtacgacgt tccggactac    2760
gcttcttgag aattc                                                     2775
```

<210> SEQ ID NO 42
<211> LENGTH: 922
<212> TYPE: PRT
<213> ORGANISM: Unknown
<220> FEATURE:
<223> OTHER INFORMATION: Synthesized

<400> SEQUENCE: 42

```
Gly Ser Ala Thr Met Ala Gln Ala Ala Leu Glu Pro Gly Lys Pro
 1               5                  10                  15

Tyr Ala Cys Pro Glu Cys Gly Lys Ser Phe Ser Arg Lys Asp Ser Leu
                20                  25                  30

Val Arg His Gln Arg Thr His Thr Gly Glu Lys Pro Tyr Lys Cys Pro
            35                  40                  45

Glu Cys Gly Lys Ser Phe Ser Gln Ser Gly Asp Leu Arg Arg His Gln
        50                  55                  60

Arg Thr His Thr Gly Glu Lys Pro Tyr Lys Cys Pro Glu Cys Gly Lys
65                  70                  75                  80

Ser Phe Ser Asp Cys Arg Asp Leu Ala Arg His Gln Arg Thr His Thr
                85                  90                  95

Gly Glu Lys Pro Tyr Ala Cys Pro Glu Cys Gly Lys Ser Phe Ser Gln
            100                 105                 110

Ser Ser His Leu Val Arg His Gln Arg Thr His Thr Gly Glu Lys Pro
        115                 120                 125

Tyr Lys Cys Pro Glu Cys Gly Lys Ser Phe Ser Asp Cys Arg Asp Leu
    130                 135                 140

Ala Arg His Gln Arg Thr His Thr Gly Glu Lys Pro Tyr Lys Cys Pro
145                 150                 155                 160

Glu Cys Gly Lys Ser Phe Ser Arg Ser Asp Lys Leu Val Arg His Gln
                165                 170                 175

Arg Thr His Thr Gly Lys Lys Thr Ser Gly Gln Ala Gly Arg Arg Asn
            180                 185                 190

Glu Met Gly Ala Ser Gly Asp Met Arg Ala Ala Asn Leu Trp Pro Ser
        195                 200                 205

Pro Leu Val Ile Lys His Thr Lys Lys Asn Ser Pro Ala Leu Ser Leu
    210                 215                 220

Thr Ala Asp Gln Met Val Ser Ala Leu Leu Asp Ala Glu Pro Pro Met
225                 230                 235                 240

Ile Tyr Ser Glu Tyr Asp Pro Ser Arg Pro Phe Ser Glu Ala Ser Met
                245                 250                 255

Met Gly Leu Leu Thr Asn Leu Ala Asp Arg Glu Leu Val His Met Ile
            260                 265                 270
```

```
Asn Trp Ala Lys Arg Val Pro Gly Phe Gly Asp Leu Asn Leu His Asp
            275                 280                 285

Gln Val His Leu Leu Glu Cys Ala Trp Leu Glu Ile Leu Met Ile Gly
            290                 295                 300

Leu Val Trp Arg Ser Met Glu His Pro Gly Lys Leu Leu Phe Ala Pro
305                 310                 315                 320

Asn Leu Leu Leu Asp Arg Asn Gln Gly Lys Cys Val Glu Gly Met Val
            325                 330                 335

Glu Ile Phe Asp Met Leu Leu Ala Thr Ser Ser Arg Phe Arg Met Met
            340                 345                 350

Asn Leu Gln Gly Glu Glu Phe Val Cys Leu Lys Ser Ile Ile Leu Leu
            355                 360                 365

Asn Ser Gly Val Tyr Thr Phe Leu Ser Ser Thr Leu Lys Ser Leu Glu
            370                 375                 380

Glu Lys Asp His Ile His Arg Val Leu Asp Lys Ile Thr Asp Thr Leu
385                 390                 395                 400

Ile His Leu Met Ala Lys Ala Gly Leu Thr Leu Gln Gln Gln His Arg
            405                 410                 415

Arg Leu Ala Gln Leu Leu Leu Ile Leu Ser His Ile Arg His Met Ser
            420                 425                 430

Asn Lys Gly Met Glu His Leu Tyr Asn Met Lys Cys Lys Asn Val Val
            435                 440                 445

Pro Leu Tyr Asp Leu Leu Leu Glu Met Leu Asp Ala His Arg Leu His
            450                 455                 460

Ala Pro Ala Ser Arg Met Gly Val Pro Pro Glu Glu Pro Ser Gln Thr
465                 470                 475                 480

Gln Leu Ala Thr Thr Ser Ser Thr Ser Ala His Ser Leu Gln Thr Tyr
            485                 490                 495

Tyr Ile Pro Pro Glu Ala Glu Gly Phe Pro Asn Thr Ile Ser Ser Gly
            500                 505                 510

Gly Gly Gly Ser Gly Gly Gly Gly Gly Ser Thr Ser Gly Gly Gly
            515                 520                 525

Gly Gly Ser Ser Gly Gly Gly Gly Ser Ser Asn Glu Met Gly Ala
            530                 535                 540

Ser Gly Asp Met Arg Ala Ala Asn Leu Trp Pro Ser Pro Leu Val Ile
545                 550                 555                 560

Lys His Thr Lys Lys Asn Ser Pro Ala Leu Ser Leu Thr Ala Asp Gln
            565                 570                 575

Met Val Ser Ala Leu Leu Asp Ala Glu Pro Pro Met Ile Tyr Ser Glu
            580                 585                 590

Tyr Asp Pro Ser Arg Pro Phe Ser Glu Ala Ser Met Met Gly Leu Leu
            595                 600                 605

Thr Asn Leu Ala Asp Arg Glu Leu Val His Met Ile Asn Trp Ala Lys
            610                 615                 620

Arg Val Pro Gly Phe Gly Asp Leu Asn Leu His Asp Gln Val His Leu
625                 630                 635                 640

Leu Glu Cys Ala Trp Leu Glu Ile Leu Met Ile Gly Leu Val Trp Arg
            645                 650                 655

Ser Met Glu His Pro Gly Lys Leu Leu Phe Ala Pro Asn Leu Leu Leu
            660                 665                 670

Asp Arg Asn Gln Gly Lys Cys Val Glu Gly Met Val Glu Ile Phe Asp
            675                 680                 685
```

```
Met Leu Leu Ala Thr Ser Ser Arg Phe Arg Met Met Asn Leu Gln Gly
        690                 695                 700

Glu Glu Phe Val Cys Leu Lys Ser Ile Ile Leu Leu Asn Ser Gly Val
705                 710                 715                 720

Tyr Thr Phe Leu Ser Ser Thr Leu Lys Ser Leu Glu Glu Lys Asp His
                725                 730                 735

Ile His Arg Val Leu Asp Lys Ile Thr Asp Thr Leu Ile His Leu Met
            740                 745                 750

Ala Lys Ala Gly Leu Thr Leu Gln Gln Gln His Arg Arg Leu Ala Gln
        755                 760                 765

Leu Leu Leu Ile Leu Ser His Ile Arg His Met Ser Asn Lys Gly Met
770                 775                 780

Glu His Leu Tyr Asn Met Lys Cys Lys Asn Val Val Pro Leu Tyr Asp
785                 790                 795                 800

Leu Leu Leu Glu Met Leu Asp Ala His Arg Leu His Ala Pro Ala Ser
                805                 810                 815

Arg Met Gly Val Pro Pro Glu Glu Pro Ser Gln Thr Gln Leu Ala Thr
            820                 825                 830

Thr Ser Ser Thr Ser Ala His Ser Leu Gln Thr Tyr Tyr Ile Pro Pro
        835                 840                 845

Glu Ala Glu Gly Phe Pro Asn Thr Ile Gly Arg Ala Asp Ala Leu Asp
850                 855                 860

Asp Phe Asp Leu Asp Met Leu Gly Ser Asp Ala Leu Asp Asp Phe Asp
865                 870                 875                 880

Leu Asp Met Leu Gly Ser Asp Ala Leu Asp Asp Phe Asp Leu Asp Met
                885                 890                 895

Leu Gly Ser Asp Ala Leu Asp Asp Phe Asp Leu Asp Met Leu Ile Asn
            900                 905                 910

Tyr Pro Tyr Asp Val Pro Asp Tyr Ala Ser
        915                 920

<210> SEQ ID NO 43
<211> LENGTH: 2775
<212> TYPE: DNA
<213> ORGANISM: Unknown
<220> FEATURE:
<223> OTHER INFORMATION: Synthesized

<400> SEQUENCE: 43
gaattctcaa gaagcgtagt ccggaacgtc gtacgggtag ttaattaaca tatcgagatc      60
gaaatcgtcc agagcatcgg agccgagcat gtccagatca aagtcatcca atgcgtcgct     120
tcccaacata tccaggtcaa agtcatcgag ggcatcagaa cccagcatgt cgagatcgaa     180
atcgtccagc gcgtcggcgc gcccgatcgt gttggggaag ccctctgctt ccggggtat      240 gtagtaggtt tgtaaggaat gtgctgaagt ggagctggtg gtggccagct gggtctggct     300
gggctcctct gggggcactc ccatgcgact ggctggggca tgaaggcggt gggcatccaa     360
catctccagg agcaggtcat agaggggcac aacgttcttg catttcatgt tgtagagatg     420
ctccatgcct tgttactca tgtgccggat atgggaaaga atgagaagga gctgagctag     480
gcggcgatgc tgctgctgca gagtcaggcc agctttggcc atcaggtgga tcaaagtgtc     540
tgtgatcttg tccaggacac ggtggatgtg gtccttctct tccagagact tcaaggtgct     600
ggacagaaac gtgtacactc cggaattaag caaaatgatg gatttgaggc acacaaactc     660
ttcaccctgc aggttcatca tgcggaaccg acttgacgta gcaagcaaca tgtcaaagat     720
```

```
ctccaccatg ccttccacac atttaccttg attcctgtcc aggagcaagt taggagcaaa    780
caggagcttc cccgggtgtt ccatggagcg ccagacgaga ccaatcatca gaatctccag    840
ccaggcacac tcgagaaggt ggacctgatc atggagattc aagtccccaa agcctggcac    900
tctctttgcc cagttgatca tatgaaccag ctccctatct gctaggttgg tcaataagcc    960
catcattgag gcttcactga agggtctaga aggatcatat tcagaataga tcatgggcgg   1020
ttcagcatcc aacaaggcac tgaccatctg gtcagctgtc aaggacaagg cagggctatt   1080
cttcttagtg tgcttaatca caagagggct tggccaaagg ttggcagccc tcatgtctcc   1140
tgaagcaccc atttcattgg aagaaccgcc accgccacca gaggagccac cgccaccgcc   1200
gctagtggaa ccacccccac caccgcccga gccaccgcca ccagaggaga tcgtgttggg   1260
gaagccctct gcttccgggg gtatgtagta ggtttgtaag gaatgtgctg aagtggagct   1320
ggtggtggcc agctgggtct ggctgggctc ctctggggcc actcccatgc gactggctgg   1380
ggcatgaagg cggtgggcat ccaacatctc caggagcagg tcatagaggg gcacaacgtt   1440
cttgcatttc atgttgtaga gatgctccat gcctttgtta ctcatgtgcc ggatatggga   1500
aagaatgaga aggagctgag ctaggcggcg atgctgctgc tgcagagtca ggccagcttt   1560
ggccatcagg tggatcaaag tgtctgtgat cttgtccagg acacggtgga tgtggtcctt   1620
ctcttccaga gacttcaagg tgctggacag aaacgtgtac actccggaat taagcaaaat   1680
gatggatttg aggcacacaa actcttcacc ctgcaggttc atcatgcgga accgacttga   1740
cgtagcaagc aacatgtcaa agatctccac catgccttcc acacatttac cttgattcct   1800
gtccaggagc aagttaggag caaacaggag cttccccggg tgttccatgg agcgccagac   1860
gagaccaatc atcagaatct ccagccaggc acactcgaga aggtggacct gatcatggag   1920
attcaagtcc ccaaagcctg gcactctctt tgcccagttg atcatatgaa ccagctccct   1980
atctgctagg ttggtcaata agcccatcat tgaggcttca ctgaagggtc tagaaggatc   2040
atattcagaa tagatcatgg gcggttcagc atccaacaag gcactgacca tctggtcagc   2100
tgtcaaggac aaggcagggc tattcttctt agtgtgctta atcacaagag ggcttggcca   2160
aaggttggca gccctcatgt ctcctgaagc acccatttca tttcggcggc cggcctggcc   2220
actagttttt ttaccggtgt gagtacgttg gtgacgcacc agcttgtcag agcggctgaa   2280
agacttgcca cattctggac atttgtatgg cttctcgcca gtatgagtgc gttgatggcg   2340
agcaaggtcg cggcagtcac taaaagattt gccgcactct gggcatttat acggttttc    2400 acccgtgtgg gtacgctggt ggcgcaccag gtgagagctc tgagagaagg acttaccaca   2460
ttccggacaa gcatagggct tctccccggt gtgagtacgt tggtgcctcg caagatcacg   2520
acaatcactg aaagacttgc cacattctgg acatttgtat ggcttctcgc cagtatgagt   2580
gcgttgatga cgcctaagat cccccgactg actaaaagat ttgccgcact ctgggcattt   2640 atacggttt tcacccgtgt gggtacgctg gtgcctcaca agcgaatcct tcctactgaa   2700
ggacttacca cattccggac aagcataggg cttctccccg ggctcgaggg ccgcctgggc   2760
catggtggcg gatcc                                                   2775
```

<210> SEQ ID NO 44
<211> LENGTH: 2739
<212> TYPE: DNA
<213> ORGANISM: Unknown
<220> FEATURE:
<223> OTHER INFORMATION: Synthesized

<400> SEQUENCE: 44

-continued

```
gaattctcaa gaagcgtagt ccggaacgtc gtacgggtag ttaattaaca tatcgagatc      60
gaaatcgtcc agagcatcgg agccgagcat gtccagatca aagtcatcca atgcgtcgct     120
tcccaacata tccaggtcaa agtcatcgag ggcatcagaa cccagcatgt cgagatcgaa     180
atcgtccagc gcgtcggcgc gcccgatcgt gttggggaag ccctctgctt ccggggggtat    240
gtagtaggtt tgtaaggaat gtgctgaagt ggagctggtg gtggccagct gggtctggct     300
gggctcctct gggggcactc ccatgcgact ggctggggca tgaaggcggt gggcatccaa     360
catctccagg agcaggtcat agaggggcac aacgttcttg catttcatgt tgtagagatg     420
ctccatgcct ttgttactca tgtgccggat atgggaaaga atgagaagga gctgagctag     480
gcggcgatgc tgctgctgca gagtcaggcc agctttggcc atcaggtgga tcaaagtgtc     540
tgtgatcttg tccaggacac ggtggatgtg gtccttctct tccagagact tcaaggtgct     600
ggacagaaac gtgtacactc cggaattaag caaaatgatg gatttgaggc acacaaactc     660
ttcaccctgc aggttcatca tgcggaaccg acttgacgta gcaagcaaca tgtcaaagat     720
ctccaccatg ccttccacac atttaccttg attcctgtcc aggagcaagt taggagcaaa     780
caggagcttc cccgggtgtt ccatggagcg ccagacgaga ccaatcatca gaatctccag     840
ccaggcacac tcgagaaggt ggacctgatc atggagattc aagtccccaa agcctggcac     900
tctctttgcc cagttgatca tatgaaccag ctccctatct gctaggttgg tcaataagcc     960
catcattgag gcttcactga agggtctaga aggatcatat tcagaataga tcatgggcgg    1020
ttcagcatcc aacaaggcac tgaccatctg gtcagctgtc aaggacaagg cagggctatt    1080
cttcttagtg tgcttaatca caagagggct tggccaaagg ttggcagccc tcatgtctcc    1140
tgaagcaccc atttcattgg aagagctagt ggaaccaccc ccaccaccgc ccgagccacc    1200
gccaccagag gagatcgtgt tggggaagcc ctctgcttcc ggggtatgt agtaggtttg     1260
taaggaatgt gctgaagtgg agctggtggt ggccagctgg gtctggctgg ctcctctgg    1320
gggcactccc atgcgactgg ctggggcatg aaggcggtgg gcatccaaca tctccaggag    1380
caggtcatag aggggcacaa cgttcttgca tttcatgttg tagagatgct ccatgccttt    1440
gttactcatg tgccggatat gggaaagaat gagaaggagc tgagctaggc ggcgatgctg    1500
ctgctgcaga gtcaggccag ctttggccat caggtggatc aaagtgtctg tgatcttgtc    1560
caggacacgg tggatgtggt ccttctcttc agagacttc aaggtgctgg acagaaacgt     1620
gtacactccg gaattaagca aaatgatgga tttgaggcac acaaactctt caccctgcag    1680
gttcatcatg cggaaccgac ttgacgtagc aagcaacatg tcaaagatct ccaccatgcc    1740
ttccacacat ttaccttgat tcctgtccag gagcaagtta ggagcaaaca ggagcttccc    1800
cgggtgttcc atggagcgcc agacgagacc aatcatcaga atctccagcc aggcacactc    1860
gagaaggtgg acctgatcat ggagattcaa gtccccaaag cctggcactc tctttgccca    1920
gttgatcata tgaaccagct ccctatctgc taggttggtc aataagccca tcattgaggc    1980
ttcactgaag ggtctagaag gatcatattc agaatagatc atgggcggtt cagcatccaa    2040
caaggcactg accatctggt cagctgtcaa ggacaaggca gggctattct tcttagtgtg    2100
cttaatcaca gagggcttg ccaaaggtt ggcagccctc atgtctcctg aagcacccat      2160
ttcatttcgg cggccggcct ggccactagt ttttttaccg gtgtgagtac gttggtgacg    2220
caccagcttg tcagagcggc tgaaagactt gccacattct ggacatttgt atggcttctc    2280
gccagtatga gtgcgttgat ggcgagcaag gtcgcggcag tcactaaaag atttgccgca    2340
```

```
ctctgggcat ttatacggtt tttcacccgt gtgggtacgc tggtggcgca ccaggtgaga    2400
gctctgagag aaggacttac cacattccgg acaagcatag ggcttctccc cggtgtgagt    2460
acgttggtgc ctcgcaagat cacgacaatc actgaaagac ttgccacatt ctggacattt    2520
gtatggcttc tcgccagtat gagtgcgttg atgacgccta agatcccccg actgactaaa    2580
agatttgccg cactctgggc atttatacgg ttttcaccc gtgtgggtac gctggtgcct    2640
cacaagcgaa tccttcctac tgaaggactt accacattcc ggacaagcat agggcttctc    2700
cccgggctcg agggccgcct gggccatggt ggcggatcc                          2739

<210> SEQ ID NO 45
<211> LENGTH: 558
<212> TYPE: DNA
<213> ORGANISM: Unknown
<220> FEATURE:
<223> OTHER INFORMATION: Synthesized
<220> FEATURE:
<221> NAME/KEY: misc_feature
<222> LOCATION: 1, 2, 557, 558
<223> OTHER INFORMATION: n = A,T,C or G

<400> SEQUENCE: 45
nnggccggcc tggccactag tttttttacc ggtgtgagta cgttggtggc gaaccaggtg      60
gctagactgg gagaaagact tgccacattc tggacatttg tatggcttct cgccagtatg    120
agtgcgttga tggcgcacca gtttatcgga gcgactaaaa gatttgccgc actctgggca    180
tttatacggt ttttcacccg tgtgggtacg ctggtggcga accaggttgc caggatcact    240
gaaggactta ccacattccg gacaagcata gggcttctcc ccggtgtgag tacgttggtg    300
acggaccaag tcgtctgaac gtgagaaaga cttgccacat tctggacatt tgtatggctt    360
ctcgccagta tgagtgcgtt gatggcgcac cagcacatcg ctgcgactaa agatttgcc    420 gcactctggg catttatacg ttttttcacc cgtgtgggta cgctggtggc gaccaggtg    480 gccactggtg ctgaaggact taccacattc cggacaagca tagggcttct ccccgggctc    540
gagggccgcc tgggccnn                                                  558

<210> SEQ ID NO 46
<211> LENGTH: 567
<212> TYPE: DNA
<213> ORGANISM: Unknown
<220> FEATURE:
<223> OTHER INFORMATION: Synthesized
<220> FEATURE:
<221> NAME/KEY: misc_feature
<222> LOCATION: 1, 2, 566, 567
<223> OTHER INFORMATION: n = A,T,C or G

<400> SEQUENCE: 46
nnggccggcc tggccactag ttctagagtc cttctgtctt aaatggattt tggtatgcct      60
cttgcgttca tcactcctgg caaacttcct cccacaaatg tcacaggcaa aaggcttctc    120
gcctgtgtgg gtgcggatgt gggtggtaag gtggtcacta cgactgaagt tacgcatgca    180
tattcgacac tggaagggct tctggcctgt gtggatgcgg atatgcgcct tcagatcagc    240
cgacttagaa aagcggcgat cgcaggactc gacagggcaa gcatagggct tctcaccggt    300
atggattttg gtatgcctct tgcgttcatc actcctggca aacttcctcc cacaaatgtc    360
acaggcaaaa ggcttctcgc ctgtgtgggt gcggatgtgg gtggtaaggt ggtcactacg    420
actgaagtta cgcatgcata ttcgacactg gaagggcttc tggcctgtgt ggatgcggat    480
atggcgcttc agatcagccg acttagaaaa gcggcgatcg caggactcga cagggcaagc    540
``` ataggctcg agggccgcct gggccnn 567

<210> SEQ ID NO 47
<211> LENGTH: 558
<212> TYPE: DNA
<213> ORGANISM: Unknown
<220> FEATURE:
<223> OTHER INFORMATION: Synthesized
<220> FEATURE:
<221> NAME/KEY: misc_feature
<222> LOCATION: 1, 2, 557, 558
<223> OTHER INFORMATION: n = A,T,C or G

<400> SEQUENCE: 47
nnggccggcc tggccactag ttttttttacc ggtgtgagta cgttggtgcc tcgcaagatc      60
acgacaatca ctgaaaagact tgccacattc tggacatttg tatggcttct cgccagtatg    120
agtgcgttga tggctggcca ggtggccggc ctggctaaaa gatttgccgc actctgggca    180
tttatacggt ttttcacccg tgtgggtacg ctggtggcgc accaggttat cgctgcggct    240
gaaggactta ccacattccg acaagcata gggcttctcc ccggtgtgag tacgttggtg    300
gcgaaccagg tggctagact gggagaaaga cttgccacat tctggacatt tgtatggctt    360
ctcgccagta tgagtgcgtt gatggcgaac cagatcatcg ctgcggctaa aagatttgcc    420
gcactctggg catttatacg gttttttcacc cgtgtgggta cgctggtggc gcaccagcac    480
atcgctgcga ctgaaggact taccacattc cggacaagca tagggcttct ccccgggctc    540
gagggccgcc tgggccnn                                                              558

<210> SEQ ID NO 48
<211> LENGTH: 38
<212> TYPE: PRT
<213> ORGANISM: Unknown
<220> FEATURE:
<223> OTHER INFORMATION: Synthesized

<400> SEQUENCE: 48

Ala Gln Ala Ala Leu Glu Pro Lys Glu Lys Pro Tyr Ala Cys Pro Glu
 1               5                  10                  15

Cys Gly Lys Ser Phe Ser Asp Pro Gly Asn Leu Val Arg His Gln Arg
            20                  25                  30

Thr His Thr Gly Glu Lys
        35

<210> SEQ ID NO 49
<211> LENGTH: 28
<212> TYPE: PRT
<213> ORGANISM: Unknown
<220> FEATURE:
<223> OTHER INFORMATION: Synthesized

<400> SEQUENCE: 49

Pro Tyr Lys Cys Pro Glu Cys Gly Lys Ser Phe Ser Arg Ser Asp Lys
 1               5                  10                  15

Leu Val Arg His Gln Arg Thr His Thr Gly Glu Lys
            20                  25

<210> SEQ ID NO 50
<211> LENGTH: 34
<212> TYPE: PRT
<213> ORGANISM: Unknown
<220> FEATURE:
<223> OTHER INFORMATION: Synthesized

<400> SEQUENCE: 50

Pro Tyr Lys Cys Pro Glu Cys Gly Lys Ser Phe Ser Gln Ser Ser His
1               5                   10                  15

Leu Val Arg His Gln Arg Thr His Thr Gly Lys Lys Thr Ser Gly Gln
            20                  25                  30

Ala Gly

<210> SEQ ID NO 51
<211> LENGTH: 38
<212> TYPE: PRT
<213> ORGANISM: Unknown
<220> FEATURE:
<223> OTHER INFORMATION: Synthesized

<400> SEQUENCE: 51

Ala Gln Ala Ala Leu Glu Pro Lys Glu Lys Pro Tyr Ala Cys Pro Glu
1               5                   10                  15

Cys Gly Lys Ser Phe Ser Gln Ser Ser Leu Val Arg His Gln Arg
            20                  25                  30

Thr His Thr Gly Glu Lys
        35

<210> SEQ ID NO 52
<211> LENGTH: 28
<212> TYPE: PRT
<213> ORGANISM: Unknown
<220> FEATURE:
<223> OTHER INFORMATION: Synthesized

<400> SEQUENCE: 52

Pro Tyr Lys Cys Pro Glu Cys Gly Lys Ser Phe Ser Gln Ser Ser Asn
1               5                   10                  15

Leu Val Arg His Gln Arg Thr His Thr Gly Glu Lys
            20                  25

<210> SEQ ID NO 53
<211> LENGTH: 34
<212> TYPE: PRT
<213> ORGANISM: Unknown
<220> FEATURE:
<223> OTHER INFORMATION: Synthesized

<400> SEQUENCE: 53

Pro Tyr Lys Cys Pro Glu Cys Gly Lys Ser Phe Ser Arg Ser Asp Lys
1               5                   10                  15

Leu Val Arg His Gln Arg Thr His Thr Gly Lys Lys Thr Ser Gly Gln
            20                  25                  30

Ala Gly

US 7,741,110 B2

REGULATION OF GENE EXPRESSION USING SINGLE-CHAIN, MONOMERIC, LIGAND DEPENDENT POLYPEPTIDE SWITCHES

RELATED APPLICATIONS

This application is a continuation application of U.S. patent application Ser. No. 09/908,153, filed Jul. 18, 2001, now U.S. Pat. No. 7,011,972, issued Mar. 14, 2006, which claims the benefit of the filing date of U.S. Provisional Patent Application Ser. No. 60/325,747, filed Jul. 18, 2000 now abandoned.

TECHNICAL FIELD OF THE INVENTION

The field of this invention is regulation of transcription. More particularly, the present invention pertains to polypeptides that can activate or repress transcription in a small molecule ligand-dependent manner.

BACKGROUND OF THE INVENTION

Designed transcription factors with defined target specificity and regulatory function provide invaluable tools for basic and applied research, and for gene therapy. Accordingly, the design of sequence-specific DNA binding domains has been the subject of intense interest for the last two decades. Of the many classes of DNA binding proteins studied, the modular $Cys_2$-$His_2$ zinc finger DNA binding motif has shown the most promise for the production of proteins with tailored DNA binding specificity. The novel architecture of this class of proteins provides for the rapid construction of gene-specific targeting devices. Polydactyl zinc finger proteins are most readily prepared by assembly of modular zinc finger domains recognizing predefined three-nucleotide sequences (See, e.g., Segal, D. J., Dreier, B., Beerli, R. R., and Barbas, C. F., III (1999) *Proc. Natl. Acad. Sci. USA* 96, 2758-2763; Beerli, R. R., Segal, D. J., Dreier, B., and Barbas, C. F., III (1998) *Proc. Natl. Acad. Sci. USA* 95, 14628-14633; and Beerli, R. R., Dreier, B., and Barbas, C. F., III (2000) *Proc. Natl. Acad. Sci. USA* 97, 1495-1500). Polydactyl proteins can be assembled using variable numbers of zinc finger domains of varied specificity providing DNA binding proteins that not only recognize novel sequences but also sequences of varied length. By combining six zinc finger domains, proteins have been produced that recognize 18 contiguous base pairs of DNA sequence, a DNA address sufficiently complex to specify any locus in the 4 billion-base pair human genome (or any other genome). Fusion of polydactyl zinc finger proteins of this type to activation or repression domains provides transcription factors that efficiently and specifically modulate the expression of both transgenes and endogenous genes (Beerli, R. R., Segal, D. J., Dreier, B., and Barbas, C. F., III (1998) *Proc. Natl. Acad. Sci. USA* 95, 14628-14633; and Beerli, R. R., Dreier, B., and Barbas, C. F., III (2000) *Proc. Natl. Acad. Sci. USA* 97, 1495-1500).

While the availability of designed transcription factors with tailored DNA binding specificities provides novel opportunities in transcriptional regulation, additional applications would be available to ligand-dependent transcription factors. Designer zinc finger proteins dependent on small molecule inducers would have a number of applications, both for the regulation of endogenous genes, and for the development of inducible expression systems for the regulation of transgenes. Natural transcription factors are regulated by a number of different mechanisms, including postranslational modification such as phosphorylation (Janknecht, R., and Hunter, T. (1997) *EMBO J* 16, 1620-1627; Darnell, J. E., Jr. (1997) *Science* 277, 1630-1635), or by ligand binding. The prototype ligand-activated transcription factors are members of the nuclear hormone receptor family, including the receptors for sex steroids or adrenocorticoids (Carson-Jurica, M. A., Schrader, W. T., and O'Malley, W. (1990) *Endocrine Reviews* 11, 201-220; Evans, R. M. (1988) *Science* 240, 889-895). These receptors are held inactive in the absence of hormone, by association with a number of inactivating factors including hsp90 (Pratt, W. B., and Toft, D. O. (1997) *Endocrine Rev.* 18, 306-360). Upon ligand binding, nuclear hormone receptors dissociate from the inactivating complex, dimerize, and become able to bind DNA and activate transcription (Carson-Jurica, M. A., Schrader, W. T., and O'Malley, W. (1990) *Endocrine Reviews* 11, 201-220; Evans, R. M. (1988) *Science* 240, 889-89512-14; and Pratt, W. B., and Toft, D. O. (1997) *Endocrine Rev.* 18, 306-360). Significantly, not only hormone binding but also inactivation and dimerization functions reside within the ligand binding domain (LBD) of these proteins (Beato, M. (1989) *Cell* 56, 335-344). This fact has been exploited experimentally and steroid hormone receptor LBDs have found wide use as tools to render heterologous proteins hormone-dependent.

In particular, the estrogen receptor (ER) LBD has been used to render the functions of c-Myc (Eilers, M., Picard, D., Yamamoto, K. R., and Bishop, J. M. (1989) *Nature* 340, 66-68), c-Fos (Superti-Furga, G., Bergers, G., Picard, D., and Busslinger, M. (1991) *Proc. Natl. Acad. Sci. USA* 88, 5114-5118), and even the cytoplasmic kinase c-Raf (. Samuels, M. L., Weber, M. J., Bishop, J. M., and McMahon, M. (1993) *Mol. Cell. Biol.* 13, 6241-6252) hormone-dependent. To develop an inducible expression system for use in basic research and gene therapy, the availability of ligand-dependent transcriptional regulators is a prerequisite. Preferentially, these regulators would be activated by a small molecule inducer with no other biological activity, bind specific sequences present only in the target promoter, and have low immunogenicity. A number of ligand-regulated artificial transcription factors have been generated by various means, using functional domains derived from either prokaryotes (Gossen, M., and Bujard, H. (1992) *Proc. Natl. Acad. Sci. USA* 89, 5547-5551 20. Gossen, M., Freundlieb, S., Bender, G., Muller, G., Hillen, W., and Bujard, H. (1995) *Science* 268, 1766-1769 21. Labow, M. A., Baim, S. B., Shenk, T., and Levine, A. J. (1990) *Mol. Cell. Biol.* 10, 3343-3356 22. Baim, S. B., Labow, M. A., Levine, A. J., and Shenk, T. (1991) *Proc. Natl. Acad. Sci. USA* 88, 5072-5076) or eukaryotes (Christopherson, K. S., Mark, M. R., Bajaj, V., and Godowski, P. J. (1992) *Proc. Natl. Acad. Sci. USA* 89, 6314-6318 24. No, D., Yao, T.-P., and Evans, R. M. (1996) *Proc. Natl. Acad. Sci. USA* 93, 3346-3351 25. Wang, Y., O'Malley, B. W., Jr., Tsai, S., and O'Malley, B. W. (1994) *Proc. Natl. Acad. Sci. USA* 91, 8180-8184 Beerli et al. -35-26. Wang, Y., Xu, J., Pierson, T., O'Malley, B. W., and Tsai, S. Y. (1997) *Gene Therapy* 4, 432-441 27. Braselmann, S., Graninger, P., and Busslinger, M. (1993) *Proc. Natl. Acad Sci. USA* 90, 1657-1661 28. Louvion, J. F., Havaux-Copf, B., and Picard, D. (1993) *Gene* 131, 129-134 29. Rivera, V. M., Clackson, T., Natesan, S., Pollock, R., Amara, J. F., Keenan, T., Magari, S. R., Phillips, T., Courage, N. L., Cerasoli, F., Jr., Holt, D. A., and Gilman, M. (1996) *Nature. Med.* 2, 1028-1032).

Of the functional domains derived from eukaryotic proteins, nuclear hormone receptor LBDs have been the most widely used. In particular, regulators based on the Gal4 DNA binding domain (DBD) fused to a human ER (Braselmann, S., Graninger, P., and Busslinger, M. (1993) *Proc. Natl. Acad. Sci. USA* 90, 1657-1661; Louvion, J. F., Havaux-Copf, B., and Picard, D. (1993) *Gene* 131, 129-134) or progesterone receptor (PR) LBD; (Wang, Y., O'Malley, B. W., Jr., Tsai, S., and O'Malley, B. W. (1994) *Proc. Natl. Acad. Sci. USA* 91, 8180-8184; Wang, Y., Xu, J., Pierson, T., O'Malley, B. W., and Tsai, S. Y. (1997) *Gene Therapy* 4, 432-441), as well as the ecdysone-inducible system based on the Drosophila ecdysone receptor-(EcR) and the mammalian retinoid X receptor (RXR) (Christopherson, K. S., Mark, M. R., Bajaj, V., and Godowski, P. J. (1992) *Proc. Natl. Acad. Sci. USA* 89, 6314-6318; No, D., Yao, T.-P., and Evans, R. M. (1996) *Proc. Natl. Acad. Sci. USA* 93, 3346-3351) have been described. Compared to the heterodimeric EcR/RXR system, regulators based on the ER and PR LBDs have the important advantage that they function as homodimers and require the delivery of only one cDNA. However, while ecdysone has no known biological effect on mammalian cells, estrogen and progesterone will elicit a biological response in cells or tissues that express the endogenous steroid receptors. With the availability of a mutated ER and a truncated PR LBDs that have lost responsiveness to their natural ligands but not to synthetic antagonists such as 4-hydroxytamoxifen (4-OHT) (Littlewood, T. D., Hancock, D. C., Danielian, P. S., Parker, M. G., and Evan, G. I. (1995) *Nucl. Acids Res.* 23, 1686-1690) or RU486 (Vegeto, E., Allan, G. F., Schrader, W. T., Tsai, M.-J., McDonnell, D. P., and O'Malley, B. W. (1992) *Cell* 69, 703-713), respectively, this is no longer of great concern. Thus, steroid hormone receptor LBD-based inducible expression systems can be developed that function independently of the endogenous steroid receptors. To date, this has been shown for the PR LBD through the development of an RU486-inducible expression system based on the Gal4 DBD (Wang, Y., O'Malley, B. W., Jr., Tsai, S., and O'Malley, B. W. (1994) *Proc. Natl. Acad. Sci. USA* 91, 8180-8184; Wang, Y., Xu, J., Pierson, T., O'Malley, B. W., and Tsai, S. Y. (1997) *Gene Therapy* 4, 432-441). An inducible expression system based on a point-mutated (G525R) ER LBD (Littlewood, T. D., Hancock, D. C., Danielian, P. S., Parker, M. G., and Evan, G. I. (1995) *Nucl. Acids Res.* 23, 1686-1690) that has lost the responsiveness to estrogen but not the antagonist 4-OHT has not been described to date. Designed zinc finger proteins have a number of advantages as compared to other DBDs, including the one derived from Gal4, since the ability to engineer DNA binding specificities allows ligand-dependent regulators to be directed to any desired artificial or natural promoter. Here we explore the utility of fusion proteins between designed zinc finger proteins and nuclear hormone receptor LBDs for the inducible control of gene expression.

BRIEF SUMMARY OF THE INVENTION

In one embodiment, the present invention provides a non-naturally occurring polypeptide that contains two ligand binding domains operatively linked to each other and a first functional domain operatively linked to one of the ligand binding domains. The ligand binding domains are preferably covalently linked to each other. More preferably, the two binding domains are covalently linked by means of a peptide linker that contains from about 10 to about 40 amino acid residues, preferably from about 15 to about 35 amino acid residues and, more preferably from about 18 to about 30 amino acid residues.

In one embodiment, the ligand-binding domains are derived from nuclear hormone receptors. The ligand binding domains can be derived from the same or different nuclear hormone receptors. Exemplary and preferred nuclear hormone receptors are steroid hormone receptors such as an estrogen receptor, a progesterone receptor, an ecdysone receptor and a retinoid X receptor.

The first functional domain can be any domain that alters the function or activity of a target nucleotide. In one embodiment, the first functional domain is a nucleotide binding domain. Preferably, the nucleotide binding domain is a DNA binding domain. The DNA binding domain preferably contains at least one zinc finger DNA binding motif, more preferably from two to twelve zinc finger DNA binding motifs and, even more preferably from three to six zinc finger DNA binding motifs. In one embodiment, the zinc finger DNA binding motifs specifically bind to a nucleotide sequence of the formula $(GNN)_{1-6}$, where G is guanidine and N is any nucleotide. In another embodiment, the first functional domain is a transcriptional regulating domain such as a transcription activation domain or a transcription repression domain.

In still another embodiment, the polypeptide gene switch contains a second functional domain. In accordance with this embodiment, a preferred first functional domain is a nucleotide binding domain and the second functional domain is a transcriptional regulating domain.

In one embodiment, a polypeptide of this invention includes (a) a DNA binding domain having from three to six zinc finger DNA binding motifs; (b) a first ligand binding domain derived from a retinoid X receptor operative linked to the DNA binding domain, a second ligand binding domain derived from an ecdyzone receptor linked to the first ligand binding domain with a peptide spacer of from 18 to 36 amino acid residues; and (c) a transcription regulating domain operatively linked to the second binding domain.

In still another embodiment, a polypeptide gene switch includes (a) a DNA binding domain having from three to six zinc finger DNA binding motifs; (b) a first ligand binding domain derived from a progesterone receptor operatively linked to the DNA binding domain, a second ligand binding domain derived from a progesterone receptor linked to the first ligand binding domain with a peptide spacer of from 18 to 36 amino acid residues; and (c) a transcription regulating domain operatively linked to the second ligand binding domain.

In another aspect, the present invention provides polynucleotides that encode a polypeptide gene switch of the invention, expression vectors containing such polynucleotides and cells containing such nucleotides.

Another aspect of this invention provides a process of regulating the function of a target nucleotide that contains a defined sequence. The process includes the step of exposing the target nucleotide to a polypeptide of this invention in the presence of a ligand that binds at least one of the ligand binding domains of the polypeptide. In a related aspect, the present invention provides a process for regulating transcription (e.g., expression) of a target nucleotide (e.g., gene). In accordance with that process a target nucleotide that contains a defined sequence is exposed to a polypeptide of this invention in the presence of a ligand that binds to at least one of the ligand binding domains of that polypeptide. The polypeptide contains a nucleotide binding domain that specifically binds to the defined sequence in the target nucleotide. Where the polypeptide gene switch contains a transcription repression domain, regulating is repression. Where the polypeptide gene switch contains a transcription activation domain, regulating is activation.

BRIEF DESCRIPTION OF THE DRAWINGS

In the drawings that form a portion of the specification

FIG. 3 shows regulation of gene expression by hormone-dependent, single-chain RXR/EcR fusion constructs. A, structure of single-chain RXR/EcR fusion proteins. B, regulation of transcription through a single binding site. HeLa cells were cotransfected with the indicated expression vectors and the E2C-TATA-luciferase reporter plasmid, carrying a single E2C binding site. 24 h after transfection, cells were either left untreated (−), or 5 μM Ponasterone A was added (+). Luciferase activity in total cell extracts was measured 48 h after transfection. Each bar represents the mean value (+/−SD) of duplicate measurements. pcDNA3.1, control plasmid that does not express a fusion protein.

FIG. 4 shows the nucleotide (SEQ ID NO: 31) and amino acid residue sequence (SEQ ID NO: 32) of zinc finger binding domain B3B.

FIG. 5 shows the nucleotide (SEQ ID NO: 33) and amino acid residue sequence (SEQ ID NO: 34) of zinc finger binding domain 2C7.

FIG. 6 shows the nucleotide (SEQ ID NO: 35) and amino acid residue sequence (SEQ ID NO: 36) of zinc finger binding domain B3C2.

FIG. 7 shows the nucleotide (SEQ ID NO: 37) sequence of repression domain (KRAB-A)$_2$.

FIG. 8 shows the nucleotide (SEQ ID NO: 38) sequence of repression domain (SID)$_2$.

FIG. 9 shows the nucleotide (SEQ ID NO: 39) and amino acid residue sequence (SEQ ID NO: 40) of polypeptide E2C-ER-L-ER-VP64.

FIG. 10 shows the nucleotide (SEQ ID NO: 41) and amino acid residue sequence (SEQ ID NO: 42) of polypeptide E2C-ER-LL-ER-VP64.

DETAILED DESCRIPTION OF THE INVENTION

I. The Invention

Figure 1B:
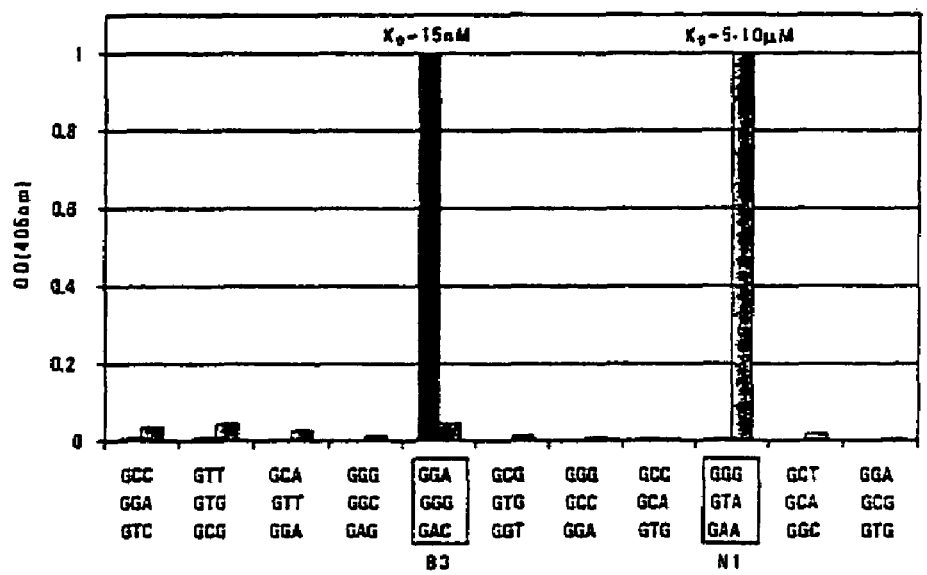
FIG. 1 shows generation of designed zinc finger proteins-with novel DNA binding specificity. A, amino acid sequence of the three-finger proteins B3 and N1. DNA recognition helix positions −2 to 6, shown in bold print, were grafted into the framework of the three finger protein Sp1C. The location of the antiparallel β sheets and the α helices, structural hallmarks of zinc finger domains, are as indicated. DNA binding specificity of each finger is shown on the left. F1-3, Finger 1-3. B, ELISA analysis of DNA binding specificity. Zinc finger proteins were expressed in E. coli as MBP fusions and purified. Specificity of binding was analyzed by measuring binding to immobilized biotinylated hairpin oligonucleotides containing the indicated 5'-(GNN)$_3$-3' sequences. Black bars, B3; gray bars, N1. The maximal signals were normalized to 1. The $K_D$ value for binding to the specific target sequence was measured by electrophoretic mobility shift assay and is labeled on top of the corresponding bars.

The present invention provides polypeptide gene switches, polynucleotides that encode such polypeptides, expression vectors that contain such polynucleotides, cells that contain such expression vectors or polynucleotides and processes for regulating target nucleotide function using such polypeptides, polynucleotides and expression vectors. Unlike existing gene switches that contain a single ligand binding domain together with a DNA binding domain and/or a transcriptional regulating domain, polypeptide gene switches of the present invention contain two ligand binding domains. Upon binding of the ligand, an intramolecular configuration change occurs that allows for alignment of the functional domains to the target gene of interest. An advantage of the present gene switches, therefore, over existing gene switches is the need for only a single molecular switch and a single expression vector for production of that switch.

II. Polypeptides

A polypeptide gene switch of the present invention includes at least three components: two ligand binding domains (LBDs) and a first functional domain (FD-1). The ligand binding domains are operatively linked to the first functional domain such that the polypeptide, in the presence of a defined ligand that binds to at least one of the ligand binding domains, can alter the function of nucleotide. The domains can be arranged in any order. As shown below, the ligand binding domains can be situated in either the amino-or carboxyl-terminal direction from the first functional domain.

A polypeptide of this invention is non-naturally occurring. As used herein, the term "non-naturally occurring" means, for example, one or more of the following: (a) a peptide comprised of a non-naturally occurring amino acid sequence; (b) a peptide having a non-naturally occurring secondary structure not associated with the peptide as it occurs in nature; (c) a peptide which includes one or more amino acids not normally associated with the species of organism in which that peptide occurs in nature; (d) a peptide which includes a stereoisomer of one or more of the amino acids comprising the peptide, which stereoisomer is not associated with the peptide as it occurs in nature; (e) a peptide which includes one or more chemical moieties other than one of the natural amino acids; or (f) an isolated portion of a naturally occurring amino acid sequence (e.g., a truncated sequence). A polypeptide of this invention exists in an isolated form and purified to be substantially free of contaminating substances. A polypeptide is synthetic in nature. That is, the polypeptide is isolated and purified from natural sources or made de novo using techniques well known in the art.

A. Ligand Binding Domain (LBD)

Each LBD is an amino acid residue sequence that is capable of and binds a particular ligand. Binding of the ligand to the LBD alters the conformation/function of the polypeptide and allows for regulating a function of a target nucleotide. In the absence of ligand, the gene switch does not work to alter nucleotide function. At least one of the LBDs is capable of binding and binds a particular ligand. Both LBDs can bind a particular ligand. Thus, the LBDs can be the same or different. Preferred LBDs are derived from nuclear hormone receptors such as steroid hormone receptors.

Exemplary and preferred steroid receptors that can serve as the source of ligand binding domains include the estrogen receptor (ER), progesterone receptor (PR), glucocorticoid-α receptor, glucocorticoid-β receptor, mineralocorticoid receptor, androgen receptor, thyroid hormone receptor, retinoic acid receptor (RAR), retinoid X receptor (RXR), Vitamin D receptor, COUP-TF receptor, ecdysone receptor (EcR), Nurr-1 receptor and orphan receptors. A preferred EcR is derived either from *Drosophila melanogaster* (DE) or *Bombyx* (BE).

As is well known in the art, steroid hormone are composed of a DNA binding domain and a ligand binding domain. The DNA binding domain contains the receptor regulating sequence and binds DNA and the ligand binding domain binds the specific biological compound (ligand) to activate the receptor. The term "ligand" refers to any compound which activates the receptor, usually by interaction with (binding) the ligand binding domain of the receptor. However, ligands also include compounds that activate the receptor without binding. Where used in a polypeptide gene switch of the present invention, it is preferred that the ligand receptor domain be modified from its naturally occurring ligand, a ligand other than the naturally occurring ligand (e.g. steroid hormone). Means of altering or derivatizing naturally occurring nuclear hormone receptor ligand binding domains to alter the binding specificity are well known in the art (See e.g. U.S. Pat. Nos. 5,874,534 and 5,599,904 the disclosures of which are incorporated herein by reference). Similarly, means for altering the estrogen receptor to change its bind affinity have reported [See, e.g. Littlewood et al., *Nucleic Acids Res.*, 3(10):1686-1690, 1995].

The term "naturally occurring ligand" refers to compounds that are normally not found in animals or humans and which bind to the ligand binding domain of a receptor. The ligand can also be a "non-native ligand", a ligand that is not naturally found in the specific organism (man or animal) in which gene therapy is contemplated. For example, certain insect hormones such as ecdysone are not found in humans. This is an example of a non-native hormone to the animal or human.

Examples of non-natural ligands, anti-hormones and non-native ligands include the following: 11 β-(4-dimethylaminophenyl)-17β-hydroxy-17β-propinyl-4,9-estradiene-3-one (Ru38486 or Mifepestone); 11β-(4-dimethylaminophenyl)-17α-hydroxy-17β-(3-hydroxypropyl)-13α-methyl-4,9-gonadiene-3-one (ZK98299 or Onapristone); 11β-(4-acetylphenyl)-17β-hydroxy-17β-(1-propinyl)-4,9-estradiene-3-one(ZK112993); 11β-(4-dimenthylaminophenyl)-17β-hydroxy-17α-(3-hydroxy-1 (Z)-propenyl-estra-4,9-diene-3-one (ZK98734); (7β11β17β)-11-(4-dimethylaminophenyl)-7-methyl-4',5' dihydrospiroy'ester-4,9-diene-17,2'(3'H)-furan!-3-one (Org31806); (11β,14β,17β)-4',5'-dihydro-11-(4-dimethy-laminophenyl)y'spirostra-4,9-diene-17,2'(3'H)-furan!-3-one (Org31376); 5-alpha-pregnane-3,2-dione. Additional non-natural ligands include, in general, synthetic non-steroidal estrogenic or anti-estrogenic compounds, broadly defined as selective estrogen receptor modulators (SERMS). Exemplary compounds include, but are not limited to, tamoxifen and raloxifen, Exemplary and preferred ligands for use with various ligand binding domains are (1) EcR: Ponasterone a, Muristerone A, GS-E (Invitrogen), Tebufenocide; (2) ER: estrogen antagonists such as 4-hydroxy-tamoxifen, ICI 164384, RU 54876, Raloxifene; and (3) PR: progesterone antagonists such as RU 486, RU 38486, and Onapristone.

An especially preferred LBD derived from a progesterone receptor comprises amino acid residues 645-914 from the human progesterone receptor. An exemplary LBD derived from an estrogen receptor comprises amino acid residues 282-599 from the mouse G225R mutant.

The two LBDs are separated by an amino acid residue sequence linker that contains from about 10 to about 50 amino acid residues. Preferably, the spacer contains from about 15 to about 40 amino acid residues and, more preferably, from about 18 to about 35 amino acid residues. Exemplary and preferred spacers contain 18 (L), 30 (LL), or 36 (LLL) amino acid residues.

B. Functional Domains

A second component of a present polypeptide is a functional domain. As used herein, the term "functional domain" and it's grammatical equivalents, means an amino acid residue sequence that binds to, alter the structure of, and/or alters the function of, a nucleotide. Exemplary such functional domains include nucleotide binding domains, transcriptional regulating domains (e.g. transcription activation domains and transcription repression domains) and domains having nuclease activity. Such domains are well known in the art.

1. Nucleotide Binding Domains

A functional domain of a polypeptide can be a nucleotide binding domain: a sequence of amino acid residues that recognize and bind to a defined nucleotide sequence. The target nucleotide sequence can be an RNA sequence or, preferably, a DNA sequence. Amino acid residue sequences that recognize and bind to defined DNA sequences are well known in the art (e.g., GAL4). Any such DNA binding peptide can be used as a DNA binding domain of a polypeptide gene switch of this invention. It is preferred, however, that the DNA binding domain of a present gene switch be one or more DNA binding zinc finger motifs. Such zinc finger DNA binding motifs are well known in the art (See, e.g., PCT Patent Application Nos. WO95/19421 and WO 98/54311, the disclosures of which are incorporated herein by reference). A DNA binding domain of a polypeptide gene switch of this invention, thus, preferably includes a multiple finger, polydactyl, zinc finger peptide that is designed to bind specific nucleotide target sequences.

The present disclosure is based on the recognition of the structural features unique to the $Cys_2$-$His_2$ zinc finger domain consist of a simple ββα fold of approximately 30 amino acids in length. Structural stability of this fold is achieved by hydrophobic interactions and by chelation of a single zinc ion by the conserved $Cys_2$-$His_2$ residues (Lee, M. S., Gippert, G. P., Soman, K. V., Case, D. A. & Wright, P. E. (1989) *Science* 245, 635-637). Nucleic acid recognition is achieved through specific amino acid side chain contacts originating from the α-helix of the domain, which typically binds three base pairs of DNA sequence (Pavletich, N. P. & Pabo, C. O. (1991) *Science* 252, 809-17, Elrod-Erickson, M., Rould, M. A., Nekludova, L. & Pabo, C. O. (1996) *Structure* 4, 1171-1180). Unlike other nucleic acid recognition motifs, simple covalent linkage of multiple zinc finger domains allows the recognition of extended asymmetric sequences of DNA.

Studies of natural zinc finger proteins have shown that three zinc finger domains can bind 9 bp of contiguous DNA sequence (Pavletich, N. P. & Pabo, C. O. (1991) *Science* 252, 809-17., Swirnoff, A. H. & Milbrandt, J. (1995) *Mol. Cell. Biol.* 15, 2275-87). Whereas recognition of 9 bp of sequence is insufficient to specify a unique site within even the small genome of *E. coli*, polydactyl proteins containing six zinc fingers domains can specify 18-bp recognition (Liu, Q., Segal, D. J., Ghiara, J. B. & Barbas III, C. F. (1997) *Proc. Natl. Acad. Sci. USA* 94, 5525-5530). With respect to the development of a universal system for gene control, and 18-bp address can be sufficient to specify a single site within all known genomes. And their efficacy in gene activation and repression within living human cells has recently been shown (Liu, Q., Segal, D. J., Ghiara, J. B. & Barbas III, C. F. (1997) *Proc. Natl. Acad. Sci. USA* 94, 5525-5530).

The zinc finger-nucleotide binding peptide domain can be derived or produced from a wild type zinc finger protein by truncation or expansion, or as a variant of the wild type-derived polypeptide by a process of site directed mutagenesis, or by a combination of the procedures. The term "truncated" refers to a zinc finger-nucleotide binding polypeptide that contains less that the full number of zinc fingers found in the native zinc finger binding protein or that has been deleted of non-desired sequences. For example, truncation of the zinc finger-nucleotide binding protein TFIIIA, which naturally contains nine zinc fingers, might be a polypeptide with only zinc fingers one through three. Expansion refers to a zinc finger polypeptide to which additional zinc finger modules have been added. For example, TFIIIA may be extended to 12 fingers by adding 3 zinc finger modules from more than one wild type polypeptide, thus resulting in a "hybrid" zinc finger-nucleotide binding polypeptide.

The term "mutagenized" refers to a zinc finger derived-nucleotide binding polypeptide that has been obtained by performing any of the known methods for accomplishing random or site-directed mutagenesis of the DNA encoding proteins. For instance, in TFIIIA, mutagenesis can be preformed to replace non-conserved residues in one or more of the repeats of the consensus sequence. Truncated zinc finger-nucleotide binding proteins can also be mutagenized. Examples of known zinc finger-nucleotide binding proteins can also be mutagenized. Examples of known zinc finger-nucleotide binding polypeptides that can be truncated, expanded, and/or mutagenized according to the present invention in order to inhibit the function of a nucleotide sequence containing a zinc finger-nucleotide binding motif includes TFIIIA and zif268. Other zinc finger-nucleotide binding proteins will be known to those of skill in the art.

A zinc finger DNA binding domain can be make using a variety of standard techniques well known in the art. Phage display libraries of zinc finger proteins were created and selected under conditions that favored enrichment of sequence specific proteins. Zinc finger domains recognizing a number of sequences required refinement by site-directed mutagenesis that was guided by both phage selection data and structural information.

A DNA binding domain used in a polypeptide of this invention is preferably a zinc finger-nucleotide binding peptide that binds to a $(GNN)_{1-6}$ nucleotide sequence. Zinc fingers that bind specifically to $(GNN)_{1-6}$ have been described in U.S. patent application Ser. No. 09/173,941, filed Oct. 16, 1998 (the disclosure of which is incorporated herein by reference).

Exemplary and preferred zinc finger DNA binding domains are designated herein as E2C, C7, B3B, 2C7, B3C2 and N1. A detailed description of the preparation of polypeptide gene switches containing zinc finger DNA binding domains can be found hereinafter in the Examples. The amino acid residue and encoding nucleotide sequences for B3B, 2C7 and B3C2 are shown in FIGS. 4-6, respectively.

2. Transcription Regulating Domains

A transcription regulating domain refers to a peptide, which acts to activate or repress transcription of a target nucleotide (e.g., gene). Transcriptional activation domains are well known in the art (See, e.g., Seipel et al., (1992) *EMBO J.*, 11:4961-4968). Exemplary and preferred transcription activation domains include VP16, TA2, VP64, STAT6, relA, TAF-1, TAF-2, TAU-1 and TAU-2. Especially preferred activation domains for use in the present invention are VP16 and VP64. Means for linking VP16 and VP64 to ligand binding domains are set forth hereinafter in the Examples.

Transcriptional repressor domains are also well known in the art. Exemplary and preferred such transcriptional repressors are ERD, KRAB, SID, histone deacetylase, DNA, methylase, and derivatives, multimers and combinations thereof such as KRAB-ERD, SID-ERD, $(KRAB)_2$, $(KRAB)_3$, KRAB-A, $(KRAB-A)_2$, $(SID)_2$, (KRAB-A)-SID and SID-(KRAB-A). A first repressor domain can be prepared using the Krüppel-associated box (KRAB) domain (Margolin et al., 1994). This repressor domain is commonly found at the N-terminus of zinc finger proteins and presumably exerts its repressive activity on TATA-dependent transcription in a distance- and orientation-independent manner, by interacting with the RING finger protein KAP-1. One can utilize the KRAB domain found between amino acids 1 and 97 of the zinc finger protein KOX1. Finally, to explore the utility of histone deacetylation for repression, amino acids 1 to 36 of the Mad mSIN2 interaction domain (SID) can be fused to another domain (Ayer et al., 1996). This small domain is found at the N-terminus of the transcription factor Mad and is responsible for mediating its transcriptional repression by interacting with mSIN3, which in turn interacts the co-repressor N-CoR and with the histone deacetylase mRPD1.

The amino acid residue and nucleotide encoding sequences of preferred transcriptional repression domains $(KRAB-A)_2$ and $(SID)_2$ are shown in FIGS. 7 and 8, respectively. Means for linking repression domains to ligand binding domains as well as exemplary polypeptide gene switches containing repression domains are set forth hereinafter in the Examples.

3. Polypeptide Gene Switches

A polypeptide of this invention, in one embodiment, comprises two ligand binding domains and a first functional domain. In another embodiment, a polypeptide gene switch comprises two ligand binding domains, a first functional domain and a second functional domain. These domains can exist in any order as shown below.

In a preferred embodiment the two ligand binding domains (LBDs) are located directly adjacent to one another, i.e., they are "serially connected" within the monomeric polypeptide gene switch of the invention and are not separated by a functional domain of the invention. The serially connected LBDs may be separated from one another by a linker molecule, such as for example a polypeptide linker molecule.

In a preferred embodiment the two LBDs are located between two functional domains (FDs) of the invention, wherein one functional domain is a Transcription Regulating Domain (TRD) and the other functional domain is a Nucleotide Binding Domain (NBD).

In one particularly preferred embodiment the monomeric polypeptide gene switch of the invention consists of two FDs and two LBDs in the sequential order FD-1/LBD-1/LBD-2/FD-2. Preferredly, in this embodiment, one functional domain is a TRD and the other functional domain is a NBD.

Preferredly, the NBD employed in the monomeric polypeptide gene switch of the invention includes 6 zinc finger binding motifs. As further described in the examples herein below, a 6 zinc finger NBD employed in a monomeric polypeptide gene switch allows for the recognition of a unique 18 bp nucleic acid sequence, which may be symmetric or asymmetric.

| LBDs | FD-1 | FD-2 |
|------|------|------|
| FD-1 | FD-2 | LBDs |

| FD-1 | LBDs | FD-2 |

| FD-2 | LBDs | FD-1 |

| FD-2 | FD-1 | LBDs |

A wide variety of polypeptide gene switches have been made. Exemplary such gene switches include (see above for definition of terms):

Gene Switches Using RXR, E2C. and Activation Domains
E2C-RXR-L-DE-VP64, E2C-RXR-LL-DE-VP64, E2C-RXR-LLL-DE-VP64, E2C-RXR-L-BE-VP64, E2C-RXR-LL-BE-VP64, E2C-RXR-LLL-BE-VP64, E2C-RXR-L-DE-VP16, E2C-RXR-LL-DE-VP16, E2C-RXR-LLL-DE-VP16, E2C-RXR-L-BE-VP16, E2C-RXR-LL-BE-VP16, E2C-RXR-LLL-BE-VP16;

Gene Switches Using RXR, 2C7, and Activation Domains
2C7-RXR-L-DE-VP64, 2C7-RXR-LL-DE-VP64, 2C7-RXR-LLL-DE-VP64, 2C7-RXR-L-BE-VP64, 2C7-RXR-LL-BE-VP64, 2C7-RXR-LLL-BE-VP64, 2C7-RXR-L-DE-VP16, 2C7-RXR-LL-DE-VP16, 2C7-RXR-LLL-DE-VP16, 2C7-RXR-L-BE-VP16, 2C7-RXR-LL-BE-VP16, E2C-RXR-LLL-BE-VP16;

Gene Switches Using RXR, B3B, and Activation Domains
B3B-RXR-L-DE-VP64, B3B-RXR-LL-DE-VP64, B3B-RXR-LLL-DE-VP64, B3B 7-RXR-L-BE-VP64, B3B 7-RXR-LL-BE-VP64, B3B-RXR-LLL-BE-VP64, B3B-RXR-L-DE-VP16, B3B-RXR-LL-DE-VP16, B3B-RXR-LLL-DE-VP16, B3B-RXR-L-BE-VP16, B3B-RXR-LL-BE-VP16, B3B-RXR-LLL-BE-VP16;

Gene Switches Using RXR, B3C2, and Activation Domains
B3C2-RXR-L-DE-VP64, B3C2-RXR-LL-DE-VP64, B3C2-RXR-LLL-DE-VP64, B3C2-RXR-L-BE-VP64, B3C2-RXR-LL-BE-VP64, B3C2-RXR-LLL-BE-VP64, B3C2-RXR-L-DE-VP16, B3C2-RXR-LL-DE-VP16, B3C2-RXR-LLL-DE-VP16, B3C2-RXR-L-BE-VP16, B3C2 B-RXR-LL-BE-VP16, B3C2-RXR-LLL-BE-VP16;

Gene Switches Using RXR, E2C, and Repression Domains
E2C-RXR-L-DE-(KRAB-A)2, E2C-RXR-LL-DE-(KRAB-A)2, E2C-RXR-LLL-DE-(KRAB-A)2, E2C-RXR-L-BE-(KRAB-A)2, E2C-RXR-LL-BE-(KRAB-A)2, E2C-RXR-LLL-BE-(KRAB-A)2, E2C-RXR-L-DE-(KRAB-A)2, E2C-RXR-LL-DE-(KRAB-A)2, E2C-RXR-LLL-DE-(KRAB-A)2, E2C-RXR-L-BE-(KRAB-A)2, E2C-RXR-LL-BE-(KRAB-A)2, E2C-RXR-LLL-BE-(KRAB-A)2, E2C-RXR-L-DE-(SID)2, E2C-RXR-LL-DE-(SID)2, E2C-RXR-LLL-DE-(SID)2, E2C-RXR-L-BE-(SID)2, E2C-RXR-LL-BE-(SID)2, E2C-RXR-LLL-BE-(SID)2, E2C-RXR-L-DE-(SID)2, E2C-RXR-LL-DE-(SID)2, E2C-RXR-LLL-DE-(SID)2, E2C-RXR-L-BE-(SID)2, E2C-RXR-LL-BE-(SID)2, E2C-RXR-LLL-BE-(SID)2;

Gene Switches Using RXR, 2C7, and Repression Domains
2C7-RXR-L-DE-(KRAB-A)2, 2C7-RXR-LL-DE-(KRAB-A)2, 2C7-RXR-LLL-DE-(KRAB-A)2, 2C7-RXR-L-BE-(KRAB-A)2, 2C7-RXR-LL-BE-(KRAB-A)2, 2C7-RXR-LLL-BE-(KRAB-A)2, 2C7-RXR-L-DE-(KRAB-A)2, 2C7-RXR-LL-DE-(KRAB-A)2, 2C7-RXR-LLL-DE-(KRAB-A)2, 2C7-RXR-L-BE-(KRAB-A)2, 2C7-RXR-LL-BE-(KRAB-A)2, 2C7-RXR-LLL-BE-(KRAB-A)2, 2C7-RXR-L-DE-(SID)2, 2C7-RXR-LL-DE-(SID)2, 2C7-RXR-LLL-DE-(SID)2, 2C7-RXR-L-BE-(SID)2, 2C7-RXR-LL-BE-(SID)2, 2C7-RXR-LLL-BE-(SID)2, 2C7-RXR-L-DE-(SID)2, 2C7-RXR-LL-DE-(SID)2, 2C7-RXR-LLL-DE-(SID)2, 2C7-RXR-L-BE-(SID)2, 2C7-RXR-LL-BE-(SID)2, E2C-RXR-LLL-BE-(SID)2,n;

Gene Switches Using RXR, B3B, and Repression Domains
B3B-RXR-L-DE-(KRAB-A)2, B3B-RXR-LL-DE-(KRAB-A)2, B3B-RXR-LLL-DE-(KRAB-A)2, B3B 7-RXR-L-BE-(KRAB-A)2, B3B 7-RXR-LL-BE-(KRAB-A)2, B3B-RXR-LLL-BE-(KRAB-A)2, B3B-RXR-L-DE-(KRAB-A)2, B3B-RXR-LL-DE-(KRAB-A)2, B3B-RXR-LLL-DE-(KRAB-A)2, B3B-RXR-L-BE-(KRAB-A)2, B3B-RXR-LL-BE-(KRAB-A)2, B3B-RXR-LLL-BE-(KRAB-A)2, B3B-RXR-L-DE-(SID)2, B3B-RXR-LL-DE-(SID)2, B3B-RXR-LLL-DE-(SID)2, B3B 7-RXR-L-BE-(SID)2, B3B 7-RXR-LL-BE-(SID)2, B3B-RXR-LLL-BE-(SID)2, B3B-RXR-L-DE-(SID)2, B3B-RXR-LL-DE-(SID)2, B3B-RXR-LLL-DE-(SID)2, B3B-RXR-L-BE-(SID)2, B3B-RXR-LL-BE-(SID)2, B3B-RXR-LLL-BE-(SID)2;

Gene Switches Using RXR, B3C2, and Repression Domains
B3C2-RXR-L-DE-(KRAB-A)2, B3C2-RXR-LL-DE-(KRAB-A)2, B3C2-RXR-LLL-DE-(KRAB-A)2, B3C2-RXR-L-BE-(KRAB-A)2, B3C2-RXR-LL-BE-(KRAB-A)2, B3C2-RXR-LLL-BE-(KRAB-A)2, B3C2-RXR-L-DE-(KRAB-A)2, B3C2-RXR-LL-DE-(KRAB-A)2, B3C2-RXR-LLL-DE-(KRAB-A)2, B3C2-RXR-L-BE-(KRAB-A)2, B3C2B-RXR-LL-BE-(KRAB-A)2, B3C2-RXR-LLL-BE-(KRAB-A)2, B3C2-RXR-L-DE-(SID)2, B3C2-RXR-LL-DE-(SID)2, B3C2-RXR-LLL-DE-(SID)2, B3C2-RXR-L-BE-(SID)2, B3C2-RXR-LL-BE-(SID)2, B3C2-RXR-LLL-BE-(SID)2, B3C2-RXR-L-DE-(SID)2, B3C2-RXR-LL-DE-(SID)2, B3C2-RXR-LLL-DE-(SID)2, B3C2-RXR-L-BE-(SID)2, B3C2 B-RXR-LL-BE-(SID)2, B3C2-RXR-LLL-BE-(SID)2;

Gene Switches Using PR, E2C, and Activation Domains
E2C-PR-L-PR-VP64, E2C-PR-LL-PR-VP64, E2C-PR-LLL-PR-VP64, E2C-PR-L-PR-VP64, E2C-PR-LL-PR-VP64, E2C-PR-LLL-PR-VP64, E2C-PR-L-PR-VP16, E2C-PR-LL-PR-VP16, E2C-PR-LLL-PR-VP16, E2C-PR-L-PR-VP16, E2C-PR-LL-PR-VP16, E2C-PR-LLL-PR-VP16;

Gene Switches Using PR, 2C7, and Activation Domains
2C7-PR-L-PR-VP64, 2C7-PR-LL-PR-VP64, 2C7-PR-LLL-PR-VP64, 2C7-PR-L-PR-VP64, 2C7-PR-LL-PR-VP64, 2C7-PR-LLL-PR-VP64, 2C7-PR-L-PR-VP16, 2C7-PR-LL-PR-VP16, 2C7-PR-LLL-PR-VP16, 2C7-PR-L-PR-VP16, 2C7-PR-LL-PR-VP16, E2C-PR-LLL-PR-VP16;

Gene Switches Using PR, B3B, and Activation Domains
B3B-PR-L-PR-VP64, B3B-PR-LL-PR-VP64, B3B-PR-LLL-PR-VP64, B3B 7-PR-L-PR-VP64, B3B 7-PR-LL-PR-VP64, B3B-PR-LLL-PR-VP64, B3B-PR-L-PR-VP16, B3B-PR-LL-PR-VP16, B3B-PR-LLL-PR-VP16, B3B-PR-L-PR-VP16, B3B-PR-LL-PR-VP16, B3B-PR-LLL-PR-VP16;

Gene Switches Using PR, B3C2, and Activation Domains
B3C2-PR-L-PR-VP64, B3C2-PR-LL-PR-VP64, B3C2-PR-LLL-PR-VP64, B3C2-PR-L-PR-VP64, B3C2-PR-LL-PR-VP64, B3C2-PR-LLL-PR-VP64, B3C2-PR-L-PR-VP16, B3C2-PR-LL-PR-VP16, B3C2-PR-LLL-PR-VP16, B3C2-PR-L-PR-VP16, B3C2 B-PR-LL-PR-VP16, B3C2-PR-LLL-PR-VP16;

Gene Switches Using PR, E2C, and Repression Domains
E2C-PR-L-PR-(KRAB-A)2, E2C-PR-LL-PR-(KRAB-A)2, E2C-PR-LLL-PR-(KRAB-A)2, E2C-PR-L-PR-(KRAB-A)2, E2C-PR-LL-PR-(KRAB-A)2, E2C-PR-LLL-PR-(KRAB-A)2, E2C-PR-L-PR-(KRAB-A)2, E2C-PR-LL-PR-(KRAB-A)2, E2C-PR-LLL-PR-(KRAB-A)2, E2C-PR-L-PR-(KRAB-A)2, E2C-PR-LL-PR-(KRAB-A)2, E2C-PR- LLL-PR-(KRAB-A)2, E2C-PR-L-PR-(SID)2, E2C-PR-LL-PR-(SID)2, E2C-PR-LLL-PR-(SID)2, E2C-PR-L-PR-(SID)2, E2C-PR-LL-PR-(SID)2, E2C-PR-LLL-PR-(SID)2, E2C-PR-L-PR-(SID)2, E2C-PR-LL-PR-(SID)2, E2C-PR-LLL-PR-(SID)2, E2C-PR-L-PR-(SID)2, E2C-PR-LL-PR-(SID)2, E2C-PR-LLL-PR-(SID)2;

Gene Switches Using PR, 2C7, and Repression Domains

2C7-PR-L-PR-(KRAB-A)2, 2C7-PR-LL-PR-(KRAB-A)2, 2C7-PR-LLL-PR-(KRAB-A)2, 2C7-PR-L-PR-(KRAB-A)2, 2C7-PR-LL-PR-(KRAB-A)2, 2C7-PR-LLL-PR-(KRAB-A)2, 2C7-PR-L-PR-(KRAB-A)2, 2C7-PR-LL-PR-(KRAB-A)2, 2C7-PR-LLL-PR-(KRAB-A)2, 2C7-PR-L-PR-(KRAB-A)2, 2C7-PR-LL-PR-(KRAB-A)2, E2C-PR-LLL-PR-(KRAB-A)2, 2C7-PR-L-PR-(SID)2, 2C7-PR-LL-PR-(SID)2, 2C7-PR-LLL-PR-(SID)2, 2C7-PR-L-PR-(SID)2, 2C7-PR-LL-PR-(SID)2, 2C7-PR-LLL-PR-(SID)2, 2C7-PR-L-PR-(SID)2, 2C7-PR-LL-PR-(SID)2, 2C7-PR-LLL-PR-(SID)2, 2C7-PR-L-PR-(SID)2, 2C7-PR-LL-PR-(SID)2, E2C-PR-LLL-PR-(SID)2,n;

Gene Switches Using PR, B3B, and Repression Domains

B3B-PR-L-PR-(KRAB-A)2, B3B-PR-LL-PR-(KRAB-A)2, B3B-PR-LLL-PR-(KRAB-A)2, B3B 7-PR-L-PR-(KRAB-A)2, B3B 7-PR-LL-PR-(KRAB-A)2, B3B-PR-LLL-PR-(KRAB-A)2, B3B-PR-L-PR-(KRAB-A)2, B3B-PR-LL-PR-(KRAB-A)2, B3B-PR-LLL-PR-(KRAB-A)2, B3B-PR-L-PR-(KRAB-A)2, B3B-PR-LL-PR-(KRAB-A)2, B3B-PR-LLL-PR-(KRAB-A)2, B3B-PR-L-PR-(SID)2, B3B-PR-LL-PR-(SID)2, B3B-PR-LLL-PR-(SID)2, B3B 7-PR-L-PR-(SID)2, B3B 7-PR-LL-PR-(SID)2, B3B-PR-LLL-PR-(SID)2, B3B-PR-L-PR-(SID)2, B3B-PR-LL-PR-(SID)2, B3B-PR-LLL-PR-(SID)2, B3B-PR-L-PR-(SID)2, B3B-PR-LL-PR-(SID)2, B3B-PR-LLL-PR-(SID)2;

Gene Switches Using PR, B3C2, and Repression Domains

B3C2-PR-L-PR(KRAB-A)2, B3 C2-PR-LL-PR-(KRAB-A)2, B3C2-PR-LLL-PR-( KRAB-A)2, B3C2-PR-L-PR-(KRAB-A)2, B3C2-PR-LL-PR-(KRAB-A)2, B3C2-PR-LLL-PR-(KRAB-A)2, B3C2-PR-L-PR-(KRAB-A)2, B3C2-PR-LL-PR-(KRAB-A)2, B3C2-PR-LLL-PR-( KRAB-A)2, B3C2-PR-L-PR-(KRAB-A)2, B3C2 B-PR-LL-PR-(KRAB-A)2, B3C2-PR-LLL-PR-(KRAB-A)2, B3C2-PR-L-PR-(SID)2, B3 C2-PR-LL-PR-(SID)2, B3C2-PR-LLL-PR-(SID)2, B3C2-PR-L-PR-(SID)2, B3C2-PR-LL-PR-(SID)2, B3C2-PR-LLL-PR-(SID)2, B3C2-PR-L-PR-(SID)2, B3C2-PR-LL-PR-(SID)2, B3C2-PR-LLL-PR-(SID)2, B3C2-PR-L-PR-(SID)2, B3C2 B-PR-LL-PR-(SID)2, B3C2-PR-LLL-PR-(SID)2;

Gene Switches Using ER, E2C, and Activation Domains

E2C-ER-L-ER-VP64, E2C-ER-LL-ER-VP64, E2C-ER-LLL-ER-VP64, E2C-ER-L-ER-VP64, E2C-ER-LL-ER-VP64, E2C-ER-LLL-ER-VP64, E2C-ER-L-ER-VP16, E2C-ER-LL-ER-VP16, E2C-ER-LLL-ER-VP16, E2C-ER-L-ER-VP16, E2C-ER-LL-ER-VP16, E2C-ER-LLL-ER-VP16;

Gene Switches Using ER, 2C7, and Activation Domains

2C7-ER-L-ER-VP64, 2C7-ER-LL-ER-VP64, 2C7-ER-LLL-ER-VP64, 2C7-ER-L-ER-VP64, 2C7-ER-LL-ER-VP64, 2C7-ER-LLL-ER-VP64, 2C7-ER-L-ER-VP16, 2C7-ER-LL-ER-VP16, 2C7-ER-LLL-ER-VP16, 2C7-ER-L-ER-VP16, 2C7-ER-LL-ER-VP16, E2C-ER-LLL-ER-VP16;

Gene Switches Using ER, B3B, and Activation Domains

B3B-ER-L-ER-VP64, B3B-ER-LL-ER-VP64, B3B-ER-LLL-ER-VP64, B3B 7-ER-L-ER-VP64, B3B 7-ER-LL-ER-VP64, B3B-ER-LLL-ER-VP64, B3B-ER-L-ER-VP16, B3B-ER-LL-ER-VP16, B3B-ER-LLL-ER-VP16, B3B-ER-L-ER-VP16, B3B-ER-LL-ER-VP16, B3B-ER-LLL-ER-VP16;

Gene Switches Using ER, B3C2, and Activation Domains

B3C2-ER-L-ER-VP64, B3C2-ER-LL-ER-VP64, B3C2-ER-LLL-ER-VP64, B3C2-ER-L-ER-VP64, B3C2-ER-LL-ER-VP64, B3C2-ER-LLL-ER-VP64, B3C2-ER-L-ER-VP16, B3C2-ER-LL-ER-VP16, B3C2-ER-LLL-ER-VP16, B3C2-ER-L-ER-VP16, B3C2 B-ER-LL-ER-VP16, B3C2-ER-LLL-ER-VP16;

Gene Switches Using ER, E2C, and Repression Domains

E2C-ER-L-ER-(KRAB-A)2, E2C-ER-LL-ER-(KRAB-A)2, E2C-ER-LLL-ER-(KRAB-A)2, E2C-ER-L-ER-(KRAB-A)2, E2C-ER-LL-ER-(KRAB-A)2, E2C-ER-LLL-ER-(KRAB-A)2, E2C-ER-L-ER-(KRAB-A)2, E2C-ER-LL-ER-(KRAB-A)2, E2C-ER-LLL-ER-(KRAB-A)2, E2C-ER-L-ER-(KRAB-A)2, E2C-ER-LL-ER-(KRAB-A)2, E2C-ER-LLL-ER-(KRAB-A)2, E2C-ER-L-ER-(SID)2, E2C-ER-LL-ER-(SID)2, E2C-ER-LLL-ER-(SID)2, E2C-ER-L-ER-(SID)2, E2C-ER-LL-ER-(SID)2, E2C-ER-LLL-ER-(SID)2, E2C-ER-L-ER-(SID)2, E2C-ER-LL-ER-(SID)2, E2C-ER-LLL-ER-(SID)2, E2C-ER-L-ER-(SID)2, E2C-ER-LL-ER-(SID)2, E2C-ER-LLL-ER-(SID)2;

Gene Switches Using ER, 2C7, and Repression Domains

2C7-ER-L-ER-(KRAB-A)2, 2C7-ER-LL-ER-(KRAB-A)2, 2C7-ER-LLL-ER-(KRAB-A)2, 2C7-ER-L-ER-(KRAB-A)2, 2C7-ER-LL-ER-(KRAB-A)2, 2C7-ER-LLL-ER-(KRAB-A)2, 2C7-ER-L-ER-(KRAB-A)2, 2C7-ER-LL-ER-(KRAB-A)2, 2C7-ER-LLL-ER-(KRAB-A)2, 2C7-ER-L-ER-(KRAB-A)2, 2C7-ER-LL-ER-(KRAB-A)2, E2C-ER-LLL-ER-(KRAB-A)2, 2C7-ER-L-ER-(SID)2, 2C7-ER-LL-ER-(SID)2, 2C7-ER-LLL-ER-(SID)2, 2C7-ER-L-ER-(SID)2, 2C7-ER-LL-ER-(SID)2, 2C7-ER-LLL-ER-(SID)2, 2C7-ER-L-ER-(SID)2, 2C7-ER-LL-ER-(SID)2, 2C7-ER-LLL-ER-(SID)2, 2C7-ER-L-ER-(SID)2, 2C7-ER-LL-ER-(SID)2, E2C-ER-LLL-ER-(SID)2,n;

Gene Switches Using ER, B3B, and Repression Domains

B3B-ER-L-ER-(KRAB-A)2, B3B-ER-LL-ER-(KRAB-A)2, B3B-ER-LLL-ER-(KRAB-A)2, B3B 7-ER-L-ER-(KRAB-A)2, B3B 7-ER-LL-ER-(KRAB-A)2, B3B-ER-LLL-ER-(KRAB-A)2, B3B-ER-L-ER-(KRAB-A)2, B3B-ER-LL-ER-(KRAB-A)2, B3B-ER-LLL-ER-(KRAB-A)2, B3B-ER-L-ER-(KRAB-A)2, B3B-ER-LL-ER-(KRAB-A)2, B3B-ER-LLL-ER-(KRAB-A)2, B3B-ER-L-ER-(SID)2, B3B-ER-LL-ER-(SID)2, B3B-ER-LLL-ER-(SID)2, B3B 7-ER-L-ER-(SID)2, B3B 7-ER-LL-ER-(SID)2, B3B-ER-LLL-ER-(SID)2, B3B-ER-L-ER-(SID)2, B3B-ER-LL-ER-(SID)2, B3B-ER-LLL-ER-(SID)2, B3B-ER-L-ER-(SID)2, B3B-ER-LL-ER-(SID)2, B3B-ER-LLL-ER-(SID)2;

Gene Switches Using ER, B3C2, and Repression Domains

B3C2-ER-L-ER-(KRAB-A)2, B3C2-ER-LL-ER-(KRAB-A)2, B3C2-ER-LLL-ER-(KRAB-A)2, B3C2-ER-L-ER-(KRAB-A)2, B3C2-ER-LL-ER-(KRAB-A)2, B3C2-ER-LLL-ER-(KRAB-A)2, B3C2-ER-L-ER-(KRAB-A)2, B3C2-ER-LL-ER-(KRAB-A)2, B3C2-ER-LLL-ER-(KRAB-A)2, B3C2-ER-L-ER-(KRAB-A)2, B3C2 B-ER-LL-ER-(KRAB-A)2, B3C2-ER-LLL-ER-(KRAB-A)2, B3C2-ER-L-ER-(SID)2, B3C2-ER-LL-ER-(SID)2, B3C2-ER-LLL-ER-(SID)2, B3C2-ER-L-ER-(SID)2, B3C2-ER-LL-ER-(SID)2, B3C2-ER-LLL-ER-(SID)2, B3C2-ER-L-ER-(SID)2, B3C2-ER-LL-ER-(SID)2, B3C2-ER-LLL-ER-(SID)2, B3C2-ER-L-ER-(SID)2, B3C2 B-ER-LL-ER-(SID)2, B3C2-ER-LLL-ER-(SID)2.

The nucleotide (SEQ ID NO: 39) and amino acid residue sequence (SEQ ID NO: 40) of polypeptide E2C-ER-L-ER-VP64 are shown in FIG. 9. The nucleotide (SEQ ID NO: 41) and amino acid residue sequence (SEQ ID NO: 42) of polypeptide E2C-ER-LL-ER-VP64 are shown in FIG. 10.

III. Polynucleotides, Expression Vectors and Host Cells

In a related aspect, the present invention provides polynucleotides that encode a polypeptide gene switch of this invention, expression vectors containing those polynucleotides, cells containing those polynucleotides and transformed cells containing those expression vectors. Vectors of primary utility for gene therapy include, but are not limited to human adenovirus vectors, adeno-associated vectors, murine or lenti virus derived retroviral vectors, or a variety of non-viral compositions including liposomes, polymers, and other DNA containing conjugates. Such vector systems can be used o deliver the gene switches either in vitro or in vivo, depending on the vector system. With adenovirus, for instance, vectors can be administered intravenously to transduce the liver and other organs, introduced directly into the lung, or into vascular compartments temporarily localized by ligation or other methods. Methods for constructing such vectors, and methods and uses for the described invention are known to those skilled in the field of gene therapy.

IV. Methods of Regulating Nucleotide Function

The present invention further provides a process for regulating the expression of a desired nucleotide sequence such as a gene. In accordance with the process, the target nucleotide sequence is exposed to an effective amount of a gene switch and a ligand, wherein the nucleotide binding domain of the gene switch binds to a portion of the target nucleotide and wherein the ligand binds to at least one of the ligand binding domains of the gene switch. Exposure can occur in vitro, in situ or in vivo. The term "effective amount" means that amount that regulates transcription of a nucleotide (e.g. structural gene or translation of RNA).

The term "regulating" refers to the suppression, enhancement, or induction of a function. For example, a polypeptide of the invention may modulate a promoter sequence by binding to a motif within the promoter, thereby enhancing or suppressing transcription of a gene operatively linked to the promoter nucleotide sequence. Alternatively, modulation may include inhibition of a gene where the polypeptide binds to the structural gene and blocks DNA dependent RNA polymerase from reading through the gene, thus inhibiting transcription of the gene. Alternatively, modulation may include inhibition of translation of a transcript.

The promoter region of a gene includes the regulatory elements that typically lie 5' to a structural gene. If a gene is to be activated, proteins known as transcription factors attach to the promoter region of the gene. This assembly resembles an "on switch" by enabling an enzyme to transcribe a second genetic segment from DNA to RNA. In most cases the resulting RNA molecule serves as a template for synthesis of a specific protein; sometimes RNA itself is the final product.

Regulation of gene expression or transcription can be accomplished both by exposing the target gene to a polypeptide switch of this invention or, preferably by transforming a cell that contains the target gene with an expression vector that contains a polynucleotide sequence that encodes a gene switch.

The Examples that follow illustrate particular embodiments of the present invention and are not limiting of the specification or claims in any way.

EXAMPLE 1

General Methods

Construction of zinc finger proteins. For the construction of the B3 and N1 zinc finger proteins, DNA recognition helices from the Zif268 Finger 2 variants pmGAA, pmGAC, pmGGA, pmGGG, and pGTA were utilized [Segal, D. J., Dreier, B., Beerli, R. R., and Barbas, C. F., III (1999) *Proc. Natl. Acad. Sci. USA* 96, 2758-2763]. Three finger proteins binding the respective 9-bp target-sites were constructed by grafting the appropriate DNA recognition helices into the framework of the three finger protein Sp1C [Desjarlais, J. R., and Berg, J. M. (1993) *Proc. Natl. Acad. Sci. USA* 90, 2256-2260]; DNA fragments encoding the two 3 finger proteins were assembled from 6 overlapping oligonucleotides as described [Beerli, R. R., Segal, D. J., Dreier, B., and Barbas, C. F., III (1998) *Proc. Natl. Acad. Sci. USA* 95, 14628-14633]. The three finger protein coding regions were then cloned into the bacterial expression vector pMal-CSS via Sfi1 digestion.

Protein purification. Moltose binding protein (MBP) fusion proteins were purified to >90% homogeneity using the Protein Fusion and Purification System (New England Biolabs), except that Zinc Buffer A (ZBA; 10 mM Tris, pH7.5/90 mM KCl, 1 mM $MgCl_2$, 90 µM $ZnCl_2$)/1% BSA /5 mM DTT) was used as the column buffer. Protein purity and concentration were determined from Coomassie blue-stained 15% SDS-PAGE gels by comparison to BSA standards.

ELISA analysis. In 96-well ELISA plates, 0.2 µg of streptavidin (Pierce) was applied to each well for 1 hour at 37° C., then washed twice with water. Biotinylated target oligonucleotide (0.025 µg) was applied in the same manner. ZBA/3% BSA was applied for blocking, but the wells were not washed after incubation. All subsequent incubations were at room temperature. Starting with 2 µg purified MBP fusion protein in the top wells, 2-fold serial dilutions were applied in 1× binding buffer (ZBA/1% BSA/5 mM DTT/0.12 µg/µl sheared herring sperm DNA). The samples were incubated 1 hour at room temperature, followed by 10 washes with water. Mouse anti-maltose binding protein mAb (Sigma) in ZBA/1% BSA was applied to the wells for 30 minutes, followed by 10 washes with water. Goat anti-mouse IgG mAb conjugated to alkaline phosphatase (Sigma) was applied to the wells for 30 minutes, followed by 10 washes with water. Alkaline phosphatase substrate (Sigma) was applied, and the $OD_{405}$ was quantitated with SOFTmax 2.35 (Molecular Devices).

Gel mobility shift assays. Target oligonucleotides were labeled at their 3' ends with [$^{32}$P] and gel purified. Eleven 3-fold serial dilutions of protein were incubated in 20 µl binding reactions (1× Binding Buffer/10% glycerol/≈1 pM target oligonucleotide) for three hours at room temperature, then resolved on a 5% polyacrlyamide gel in 0.5×TBE buffer. Quantitation of dried gels was performed using a PhosphorImager and ImageQuant software (Molecular Dynamics), and the $K_D$ was determined by Scatchard analysis.

Reporter constructs for determining the optimal spacing and orientation of the two half-sites. C7 dimer-TATA fragments were generated by PCR amplification with C7 dimer-TATA primers (5'-GAG GGT ACC <u>GCGTGGGCG</u> $A_{0-5}$ <u>GCGTGGGCG</u> AGT CGA CTC TAG AGG GTA TAT AAT GG-3' (SEQ ID NO: 1) for direct repeats; 5'-GAG GGT ACC <u>GCGTGGGCG</u> $A_{0-5}$ <u>CGCCCACGC</u> AGT CGA CTC TAG AGG GTA TAT AAT GG-3' (SEQ ID NO: 2) for inverted repeats; 5'-GAG GGT ACC <u>CGCCCACGC</u> $A_{0-5}$ <u>GCGTGGGCG</u> AGT CGA CTC TAG AGG GTA TAT AAT GG-3' (SEQ ID NO: 3) for everted repeats) and GLprimer2 (5'-CTT TAT GTT TTT GGC GTC TTC C-3' (SEQ ID NO: 4); Promega), using p17×4TATA-luc (gift from S. Y. Tsai) as a template. PCR products were cloned into pGL3-Basic (Promega) via digestion with the restriction endonucleases Kpn1 and Nco1.

RU486- and Tamoxifen-inducible promoter constructs. 10×C7-TATA, 10×B3-TATA, and 10×N1-TATA fragments were assembled from two pairs of complementary oligonucleotides each and cloned into Sac1-Xma1 linearized pGL3-Basic (Promega), upstream of the firefly luciferase coding region, creating the plasmids 10×C7-TATA-luc, 10×B3-TATA-luc, and 10×N1-TATA-luc. To generate the 10×N1-TATA-lacZ reporter construct, the lacZ coding region was excised from pβgal-Basic (Clontech) and used to replace the luciferase coding region of 10×N1-TATA-luc via Hind3-BamH1 digestion.

Luciferase and β-gal reporter assays. For all transfections, HeLa cells were plated in 24-well dishes and used at a confluency of 40-60%. For luciferase reporter assays, 175 ng reporter plasmid (promotor constructs in pGL3 or, as negative control, pGL3-Basic) and 25 ng effector plasmid (zinc finger-steroid receptor fusions in pcDNA3 or, as negative control, empty pcDNA3) were transfected using the Lipofectamine reagent (Gibco BRL). After approximately 24 h, expression was induced by the addition of 10 nM RU486 (Biomol), 100 nM 4-OHT (Sigma), or 5 mM Ponasterone A (Invitrogen). Cell extracts were prepared approximately 48 hours after transfection and assayed for luciferase activity using the Promega luciferase assay reagent in a MicroLumat LB96P luminometer (EG&G Berthold, Gaithersburg, Md.). For dual reporter assays, 85 ng luciferase reporter plasmid, 85 ng b-gal reporter plasmid, and 15 ng of each of the two effector plasmids were transfected. b-gal activity was measured using the luminescent b-galactosidase detection kit II (Clontech).

Zinc finger-steroid receptor fusion constructs with N-terminal effector domains. The VP16 coding region was PCR amplified from pcDNA3/C7-VP16 using the primers VPNhe-F (5'-GAG GAG GAG GAG GCT AGC GCC ACC ATG GGG CGC GCC GGC GCT CCC CCG ACC GAT GTC AGC CTG-3') (SEQ ID NO: 5), and VPHind-B (5'-GAG GAG GAG GAG AAG CTT GTT AAT TAA ACC GTA CTC GTC AAT TCC AAG GGC ATC G-3') (SEQ ID NO: 6) or VPNLSHind-B (5'-GAG GAG GAG GAG AAG CTT AAC TTT GCG TTT CTT TTT CGG GTT AAT TAA ACC GTA CTC GTC AAT TCC AAG GGC ATC G-3') (SEQ ID NO: 7). The C7 coding region was amplified from the same plasmid, using the primers C7Hind-F (5'-GAG GAG GAG GAG AAG CTT GGG GCC ACG GCG GCC CTC GAG CCC TAT GC-3') (SEQ ID NO: 8), and C7Bam-B (5'-GAG GAG GGA TCC CCC TGG CCG GCC TGG CCA CTA GTT CTA GAG TC-3') (SEQ ID NO: 9) or C7NLSBam-B (5'-GAG GAG GGA TCC CCA ACT TTG CGT TTC TTT TTC GGC TGG CCG GCC TGG CCA CTA GTT CTA GAG TC-3') (SEQ ID NO: 10). The human PR truncated LBD (aa645-914) was amplified from PAPCMVGL914VPc'-SV [Wang, Y., Xu, J., Pierson, T., O'Malley, B. W., and Tsai, S. Y. (1997) Gene Therapy 4, 432-441] using the primers PRBam-F (5'-GAG GAG GAG GAG GGA TCC AGT CAG AGT TGT GAG AGC ACT GGA TGC TG-3') (SEQ ID NO: 11) and PREco-B (5'-GAG GAG GAA TTC TCA AGC AAT AAC TTC AGA CAT CAT TTC TGG AAA TTC-3') (SEQ ID NO: 12). The VP16-C7-PR, VP16-NLS-C7-PR, and VP16-C7-NLS-PR coding regions were then assembled in pcDNA3.1(+)Zeo (Invitrogen) using the Nhe1, Hind3, BamH1, and EcoR1 restriction sites incorporated in the PCR primers. In the resulting constructs, the C7 coding regions were flanked by two Sfi1 sites, and the VP16 coding regions by Asc1 and Pac1 sites. These restriction sites were introduced to facilitate the exchange of DBDs and effector domains, respectively.

To generate the VP16-C7-ER, VP16-NLS-C7-ER, and VP16-C7-NLS-ER constructs, the point-mutated murine ER LBD coding region (aa281-599, G525R) was excised from pBabe/Myc-ER [Littlewood, T. D., Hancock, D. C., Danielian, P. S., Parker, M. G., and Evan, G. I. (1995) Nucl. Acids Res. 23, 1686-1690], and used to replace the PR LBD coding region via BamH1-EcoR1 restriction digestion.

To generate fusion constructs with B3 or N1 DBDs, C7 was replaced by the B3 or N1 coding regions via Sfi1 digestion. Fusion constructs containing a VP64 effector domain were produced by replacing VP16 by the VP64 coding region via Asc1-Pac1 digestion.

Zinc finger-steroid receptor fusion constructs with C-terminal effector domains. The truncated human PR LBD was amplified from PAPCMVGL914VPc'-SV [Wang, Y., Xu, J., Pierson, T., O'Malley, B. W., and Tsai, S. Y. (1997) Gene Therapy 4, 432-441] using the primers PRFse-F (5'-GAG GAG GAG GAG GAG GGC CGG CCG CGT CGA CCA GGT CAG AGT TGT GAG AGC ACT GGA TGC-3') (SEQ ID NO: 13) and PRAsc-B (5'-GAG GAG GAG GAG GAG GGC GCG CCC CGT CGA CCC AGC AAT AAC TTC AGA CAT CAT TTC TGG-3') (SEQ ID NO: 14). The point-mutated mouse ER LBD was amplified from pBabe/Myc-ER [Littlewood, T. D., Hancock, D. C., Danielian, P. S., Parker, M. G., and Evan, G. I. (1995) Nucl. Acids Res. 23, 1686-1690] using the primers ERFse-F (5'-GAG GAG GAG GAG GAG GGC CGG CCG CCG AAA TGA AAT GGG TGC TTC AGG AGA C-3') (SEQ ID NO: 15) and ERAsc-B (5'-GAG GAG GAG GAG GAG GGC GCG CCC GAT CGT GTT GGG GAA GCC CTC TGC TTC-3') (SEQ ID NO: 16). The resulting PCR products were then inserted into pcDNA3/E2C-VP16 [Beerli, R. R., Segal, D. J., Dreier, B., and Barbas, C. F., III (1998) Proc. Natl. Acad. Sci. USA 95, 14628-14633], in between the E2C and VP16 coding regions, via digestion with the restriction endonucleases Fse1 and Asc1.

To generate fusion constructs with B3 or N1 DBDs, E2C was replaced by the B3 or N1 coding regions via Sfi1 digestion. Fusion constructs containing a VP64 effector domain were produced by replacing VP16 by the VP64 coding region via Asc1-Pac1 digestion.

Heterodimeric switch constructs. For construction of the E2C-ER fusion, the point-mutated mouse ER LBD was amplified from pBabe/Myc-ER [Littlewood, T. D., Hancock, D. C., Danielian, P. S., Parker, M. G., and Evan, G. I. (1995) Nucl. Acids Res. 23, 1686-1690] using the primers ERFse-F and ERPac-B (5'-GAG GAG GAG GAG GAG TTA ATT AAG ATC GTG TTG GGG AAG CCC TCT GCT TC-3') (SEQ ID NO: 17). The PCR product was then inserted into the construct pcDNA3/E2C-VP64, replacing the VP64 coding region, via Fse1-Pac1 digestion. To generate the ER-VP64 fusion, the ER LBD was amplified using the primers ERAT-GBam-F (5'-GAG GAG GAG GAG GGA TCC GCC ACC ATG CGA AAT GAA ATG GGT GCT TCA GGA GAC-3') (SEQ ID NO: 18) and ERAsc-B. The PCR product was then inserted into pcDNA3/E2C-VP64, [Beerli, R. R., Segal, D. J., Dreier, B., and Barbas, C. F., III (1998) Proc. Natl. Acad. Sci. USA 95, 14628-14633] replacing the E2C coding region, via BamH1-Asc1 digestion.

Single-chain switch constructs. For construction of single-chain fusions with two ER LBDs, the point-mutated mouse ER LBD was amplified from pBabe/Myc-ER [Littlewood, T. D., Hancock, D. C., Danielian, P. S., Parker, M. G., and Evan, G. I. (1995) Nucl. Acids Res. 23, 1686-1690] either using the primers ERFse-F and ERSpe1-B (5'-GAG GAG GAG GAG GAG GAG ACT AGT GGA ACC ACC CCC ACC ACC GCC CGA GCC ACC GCC ACC AGA GGA GAT CGT GTT GGG GAA GCC CTC TGC-3') (SEQ ID NO: 19), or using the primers ERNhe1-F1 (for 18aa linker construct; 5'-GAG GAG GAG GAG GAG GAG GCT AGC GGC GGT GGC GGT GGC TCC TCT GGT GGC GGT GGC GGT TCT TCC AAT GAA ATG GGT GCT TCA GGA GAC-3') (SEQ ID NO: 20) or ERNhe1-F2 (for 30aa linker construct; 5'-GAG GAG GAG GAG GAG GAG GCT AGC TCT TCC AAT GAA ATG GGT GCT TCA GGA GAC-3') (SEQ ID NO: 21), and ERAsc-B. The PCR products were then digested with, respectively, Fse1 and Spe1, or Nhe1 and Asc1, and inserted into Fse1-Asc1 linearized pcDNA3/E2C-VP64 [Beerli, R. R., Segal, D. J., Dreier, B., and Barbas, C. F., III (1998) Proc. Natl. Acad. Sci. USA 95, 14628-14633].

For construction of RXR-EcR single-chain fusions, the ligand binding domain of the human retinoid X receptor (hRXRα, aa373-654) was PCR amplified from pVgRXR (In-vitrogen) using the primers RXRFse-F (5'-GAG GAG GAG GGC CGG CCG GGA AGC CGT GCA GGA GGA GCG GC-3') (SEQ ID NO: 22) and RXRSpe-B (5'-GAG GAG GAG GAG GAG ACT AGT GGA ACC ACC CCC ACC ACC GCC CGA GCC ACC GCC ACC AGA GGA AGT CAT TTG GTG CGG CGC CTC CAG C-3') (SEQ ID NO: 23). The ligand binding domain of the ecdysone receptor (EcR, aa202-462, drosophila melanogaster) was PCR amplified from pVgRXR using the primers EcRNhe-F1 (for 18aa linker construct; 5'-GAG GAG GAG GAG GCT AGC TCT TCC GGT GGC GGC CAA GAC TTT GTT AAG AAG G-3') (SEQ ID NO: 24), or EcRNhe-F2 (for 30aa linker construct; 5'-GAG GAG GAG GAG GCT AGC GGC GGT GGC GGT GGC TCC TCT GGT GGC GGT GGC GGT TCT TCC GGT GGC GGC CAA GAC TTT GTT AAG AAG G-3') (SEQ ID NO: 25), and EcRAsc-B (5'-GAG GAG GAG GGC GCG CCC GGC ATG AAC GTC CCA GAT CTC CTC GAG-3') (SEQ ID NO: 26). The PCR products were then digested with, respectively, Fse1 and Spe1, or Nhe1 and Asc1, and inserted into Fse1-Asc1 linearized pcDNA3/E2C-VP64 [Beerli, R. R., Segal, D. J., Dreier, B., and Barbas, C. F., III (1998) Proc. Natl. Acad. Sci. USA 95, 14628-14633]. DNA binding domains were exchanged via Sfi1 digestion, effector domains via Asc1-Pac1 digestion.

To generate the 36aa linker, E2C-RLLE-VP64 fusion construct, the RXR LBD was PCR amplified from pcDNA3/E2C-RE-VP64 using the primers RXRFse-F and RXR-SpeLL-B (5'-GAG GAG GAG GAG GAG ACT AGT AGA GCC ACC GCC CCC TTC AGA ACC GCC CGA GCC ACC GCC ACC AGA GG-3') (SEQ ID NO: 27). The EcR LBD was amplified from the same plasmid, using the primers EcRN-heLL-F (5'-GAG GAG GAG GAG GCT AGC GGG GGT TCG GAG GGT GGC GGG TCT GAG GGT GGG GGT GGT TCC ACT AGC TCT TCC-3') (SEQ ID NO: 28) and EcRAsc-B. The PCR products were inserted into pcDNA3/E2C-VP64 as described above.

EXAMPLE 2

Gene Switches

Generation of hormone-regulated zinc finger-steroid receptor fusion proteins. Previous studies have shown the potential of engineered C2-H2 zinc finger proteins for the regulation of target gene expression [. Liu, Q., Segal, D. J., Ghiara, J. B., and Barbas, C. F., III (1997) Proc. Natl. Acad. Sci. USA 94, 5525-5530; Kim, J. S., and Pabo, C. O. (1997) J. Biol Chem 272, 29795-29800; Beerli, R. R., Segal, D. J., Dreier, B., and Barbas, C. F., III (1998) Proc. Natl. Acad. Sci. USA 95, 14628-14633; Beerli, R. R., Dreier, B., and Barbas, C. F., III (2000) Proc. Natl. Acad. Sci. USA 97, 1495-1500]. However, to fully realize the potential of engineered zinc finger proteins, it is desirable that their otherwise constitutive DNA binding activity be rendered ligand-dependent. The ligand binding domains (LBDs) of the human progesterone receptor (hPR) and the murine estrogen receptor (mER) have previously been used for the regulation of heterologous proteins, after having been modified to lack binding to the natural hormones while retaining binding to synthetic antagonists [Littlewood, T. D., Hancock, D. C., Danielian, P. S., Parker, M. G., and Evan, G. I. (1995) Nucl. Acids Res. 23, 1686-1690; Wang, Y., Xu, J., Pierson, T., O'Malley, B. W., and Tsai, S. Y. (1997) Gene Therapy 4, 432-441]. Thus, the Zif268 variant C7 [Wu, H., Yang, W.-P., and Barbas, C. F., III (1995) Proc. Natl. Acad. Sci. USA 92, 344-348] was fused to a transcriptional activation domain plus the LBD of either of the two nuclear hormone receptors. The VP64-C7-PR fusion protein contains an N-terminal VP64 activation domain [Beerli, R. R., Segal, D. J., Dreier, B., and Barbas, C. F., III (1998) Proc. Natl. Acad. Sci. USA 95, 14628-14633], and a C-terminal hPR LBD (aa645-914) lacking amino acids 915-933, responsive to the progesterone-antagonist RU486/Mifepristone but not to progesterone [Wang, Y., Xu, J., Pierson, T., O'Malley, B. W., and Tsai, S. Y. (1997) Gene Therapy 4,432-441]. The VP64-C7-ER fusion protein contains a C-terminal mER LBD (aa282-599) with a single amino acid substitution (G525R), and is responsive to the estrogen antagonist 4-hydroxy-tamoxifen (4-OHT) but not to estrogen [Littlewood, T. D., Hancock, D. C., Danielian, P. S., Parker, M. G., and Evan, G. I. (1995) Nucl. Acids Res. 23, 1686-1690].

Determination of the optimal response element for zinc finger-steroid receptor fusion proteins. Naturally occurring steroid receptors bind DNA as dimers and typically recognize response elements consisting of palindromic sequences [Evans, R. M. (1988) Science 240, 889-895; Carson-Jurica, M. A., Schrader, W. T., and O'Malley, W. (1990) Endocrine Reviews 11, 201-220]. Moreover, it was demonstrated that in some cases also direct repeats can serve as binding sites for receptor dimers [Aumais, J. P., Lee, H. S., DeGannes, C., Horsford, J., and White, J. H. (1996) J. Biol. Chem. 271, 12568-12577]. Given this obvious flexibility in DNA recognition by naturally occurring receptor dimers, the optimal structure of a response element for an artificial, zinc finger based transcriptional switch was not known. However, to develop an efficient, hormone-inducible system for the regulation of target gene expression, a detailed knowledge of the binding site architecture is required.

To determine the optimal orientation and spacing of the two half-sites of a response element for a zinc finger-LBD fusion protein, a series of reporter plasmids was constructed. Each contains two C7 binding sites upstream of a TATA box and a firefly luciferase coding region. The two C7 binding sites were introduced in different orientations (direct, inverted, or everted repeat) and with various spacings (no spacing or 1 to 5 bp spacing). Plasmids directing expression of VP64-C-PR or VP64-C7-ER fusion constructs were then co-transfected with the various reporter plasmids and assayed for hormone-induced luciferase expression. Significantly, each of the C7 dimer binding sites was able to act as a response element for both PR and ER based proteins, albeit at varying efficiency.

In contrast, a reporter plasmid with a single C7 binding site was not activated, indicating that hormone-induced activation of transcription was mediated by dimers.

Optimal spacing depended on the orientation of the two half-sites. In the case of the PR fusion protein, optimal spacing seemed to be at 2-3 bp for inverted repeats and 3 bp for everted repeats. Response elements consisting of direct repeats had no single optimal spacing; the best response was obtained with 4-5 bp, or no spacing at all. For the ER fusion protein, optimal spacing was at 3-4 bp for direct repeats, 1-2 bp for inverted repeats, and 3 bp for everted repeats. It should be noted that there were significant variations in the basal, i.e. ligand-independent activity of PR and ER fusion proteins, depending on the response element tested. Most notably, increasing the spacing of direct repeats from 3 to 4 bp led to a 1.9-fold higher basal activity of VP64-C7-PR, and even a 3.7-fold increase in the case of VP64-C7-ER. High basal activity is extremely undesirable for an inducible promoter system, where tight control over the expression levels of a particular gene of interest is often required, especially if the gene product is toxic. Thus, in choosing appropriate response elements, particular attention must be paid not only to hormone inducibility but also to its basal activity in the presence of the regulatory protein. The response element consisting of direct repeats with a spacing of three nucleotides was considered to be a good choice for use in a hormone-inducible artificial promoter, since it was compatible with both PR and ER fusion proteins. Significantly, its basal activity in the presence of either PR or ER fusion proteins was among the lowest of all response elements tested. Furthermore, good hormone induced activation of transcription was observed with both VP64-C7-PR (3.9-fold) and VP64-C7-ER (9.5-fold).

Generation of novel DNA binding domains. While the use of the C7 DNA binding domain was well suited for the preliminary studies described above, it may not be a good choice for incorporation into an inducible transcriptional regulator. The C7 protein is a variant of the mouse transcription factor Zif268 [Pavletich, N. P., and Pabo, C. O. (1991) *Science* 252, 809-817], with increased affinity but unchanged specificity [Wu, H., Yang, W.-P., and Barbas, C. F., III (1995) *Proc. Natl. Acad. Sci. USA* 92, 344-348]. We reasoned that the use of alternate DNA binding domains would minimize potential pleiotropic effects of the chimeric regulators. Previously, we described a strategy for the rapid assembly of zinc finger proteins from a family of predefined zinc finger domains specific for each of the sixteen 5'-GNN-3' DNA triplets [Beerli, R. R., Segal, D. J., Dreier, B., and Barbas, C. F., III (1998) *Proc. Natl. Acad. Sci. USA* 95, 14628-14633; Segal, D. J., Dreier, B., Beerli, R. R., and Barbas, C. F., III (1999) *Proc. Natl. Acad. Sci. USA* 96, 2758-2763]. Three finger proteins binding any desired 5'-(GNN)$_3$-3' sequence can be rapidly prepared by grafting the amino acid residues involved in base-specific DNA recognition into the framework of the consensus three finger protein Sp1C [Desjarlais, J. R., and Berg, J. M. (1993) *Proc. Natl. Acad. Sci. USA* 90, 2256-2260]. To date, well over 100 three finger proteins have been produced in our laboratory. Two of these, B3 and N1, were chosen to be used in inducible transcriptional regulators (FIG. 1A). The B3 and Ni proteins are designed to bind the sequences 5'-GGA GGG GAC-3' or 5'-GGG GTA GAA-3', respectively. To verify their DNA binding specificity, these proteins were purified as MBP-fusions and tested by ELISA analysis using an arbitrary selection of oligonucleotides containing 5'-(GNN)$_3$-3' sequences (FIG. 1B). Significantly, both proteins recognized their target sequence and showed no crossreactivity to any of the other 5'-(GNN)$_3$-3' sequences tested. However, as judged by ELISA, binding of N1 was much weaker than binding of B3. Therefore, affinities were determined by electrophoretic mobility-shift analysis. The B3 protein bound its target sequence with a $K_D$ value of 15 nM, similar to the $K_D$ values we previously reported for other three finger proteins [Beerli, R. R., Segal, D. J., Dreier, B., and Barbas, C. F., III (1998) *Proc. Natl. Acad. Sci. USA* 95, 14628-14633]. In contrast, N1 affinity for its target was dramatically lower and we estimate its KD value to be in the range of 5-10 µM. The fact that the two proteins had very different affinities for their respective target sequences was considered positive, since it allows to investigate the influence of affinity on the functionality of an inducible expression system.

RU486- and 4-OHT-inducible systems for the control of gene expression. To allow for a comparative analysis, a series of RU486- or 4-OHT-inducible transcriptional regulators were constructed containing either the B3 or the N1 DNA binding domain. The role of placement of the activation domain was investigated, by fusing it either to the N- or the C-terminus of the protein. Two different activation domains were compared: the herpes simplex virus VP16 transactivation domain [Sadowski, I., Ma, J., Triezenberg, S., and Ptashne, M. (1988) *Nature* 335, 563-564], and the synthetic VP64 activation domain, which consists of 4 tandem repeats of VP16's minimal activation domain [Beerli, R. R., Segal, D. J., Dreier, B., and Barbas, C. F., III (1998) *Proc. Natl. Acad. Sci. USA* 95, 14628-14633].

Synthetic promoters were constructed based on the B3 and N1 DNA target sequences, and the optimal response element structure defined above. The 10×B3-TATA-luc and 10×N1-TATA-luc plasmids each contain five response elements, consisting of direct repeats spaced by three nucleotides, upstream of a TATA box and a firefly luciferase coding region. The response elements are separated from each other by six nucleotides, which should allow the concomitant binding of five dimers and thus maximize the promoter activity. The activity of the various fusion constructs was assessed by transient cotransfection studies with the cognate TATA reporter plasmids in HeLa cells (Table 1).

TABLE 1

|  | LBD = PR | | LBD = ER | |
| --- | --- | --- | --- | --- |
|  | exp. 1 | exp. 2 | exp. 1 | exp. 2 |
| VP16-B3-LBD | 34x | 36x | 37x | 26x |
| VP64-B3-LBD | 37x | 24x | 26x | 27x |
| B3-LBD-VP16 | 115x | 116x | 47x | 58x |
| B3-LBD-VP64 | 110x | 85x | 62x | 99x |
| VP16-N1-LBD | 188x | 159x | 101x | 39x |
| VP64-N1-LBD | 206x | 390x | 49x | 58x |
| N1-LBD-VP16 | 282x | 203x | 24x | 30x |
| N1-LBD-VP64 | 151x | 129x | 1319x | 464x |

In general, the ER fusion proteins turned out to be the stronger transactivators, and 4-OHT-induced luciferase activity was usually 3 to 6 times higher than RU486-induced luciferase activity mediated by PR fusion proteins. However, since the basal, i.e. ligand independent, activity of ER chimeras was often somewhat higher, their hormone-induced fold-stimulation was not generally better. Hormone-dependent gene activation in excess of 2 orders of magnitude was commonly observed with both PR and ER fusion proteins, values that are significantly better than what was previously reported for the Gal4-PR fusion protein GLVPc' [Wang, Y., Xu, J., Pierson, T., O'Malley, B. W., and Tsai, S. Y. (1997) *Gene Therapy* 4, 432-441].

The placement of the activation domain had a significant influence on the activity of the chimeric regulators. However, favored placement was dependent on the nature of the activation domain. Whereas the VP16 domain yielded the more potent activators when placed at the C-terminus, the VP64 was more active at the N-terminus. Accordingly, direct comparisons showed that an N-terminal VP64 was more potent than a N-terminal VP16 domain, and a C-terminal VP16 was more potent than a C-terminal VP64 domain. The nature and placement of the activation domain was also found to have an influence on the basal activity of the chimeric regulators. In particular, a relatively high basal activity was observed in the case of regulators with N-terminal VP64 domain.

The nature of the DNA binding domain had a major influence on the extent of ligand-dependence of the chimeras. Use of the N1 protein as DNA binding domain led to more tightly regulated fusion constructs with significantly better fold-stimulation of promoter activities than the use of B3, likely due to the dramatic affinity differences between N1 and B3. In particular, the N1-ER-VP64 regulator had no significant basal activity and was capable of mediating a 464- to 1319-fold 4-OHT-induced activation of the 10×N1-TATA minimal promoter (Table 1). The extent of ligand-induced activation of gene expression over a range of 3 orders of magnitude is particularly remarkable, since it has thus far only been reported for the tetracycline controlled system of gene regulation [Gossen, M., and Bujard, H. (1992) *Proc. Natl. Acad. Sci. USA* 89, 5547-5551; Gossen, M., Freundlieb, S., Bender, G., Müller, G., Hillen, W., and Bujard, H. (1995) *Science* 268, 1766-1769].

Concomitant regulation of multiple promoters. Zinc finger technology has made a large repertoire of DNA binding specificities available for use in protein engineering [Beerli, R. R., Segal, D. J., Dreier, B., and Barbas, C. F., III (1998) *Proc. Natl. Acad. Sci. USA* 95, 14628-14633; Segal, D. J., Dreier, B., Beerli, R. R., and Barbas, C. F., III (1999) *Proc. Natl. Acad. Sci. USA* 96, 2758-2763; Beerli, R. R., Dreier, B., and Barbas, C. F., III (2000) *Proc. Natl. Acad. Sci. USA* 97, 1495-1500]. The availability of different steroid hormone receptor-derived regulatory domains [Littlewood, T. D., Hancock, D. C., Danielian, P. S., Parker, M. G., and Evan, G. I. (1995) *Nucl. Acids Res.* 23, 1686-1690; Wang, Y., Xu, J., Pierson, T., O'Malley, B. W., and Tsai, S. Y. (1997) *Gene Therapy* 4, 432-441], and the ability to redirect chimeric regulators to virtually any desired target sequence should make it possible to independently regulate the expression of multiple genes at the same time. To examine this possibility, a reporter plasmid was constructed directing expression of β-galactosidase (β-gal) under the control of the 10×N1-TATA minimal promoter. The chimeric regulators B3-PR-VP16 and N1-ER-VP64 were then transiently expressed in HeLa cells along with the 10×B3-TATA-luc and 10×N1-TATA-β-gal reporter plasmids. The transfected cells were treated with either RU486 or 4-OHT and the luciferase and β-gal activities were monitored. Significantly, RU486 induced expression of luciferase while having no effect on β-gal reporter gene activity. 4-OHT, on the other hand, did not affect luciferase expression but efficiently activated β-gal expression. These results demonstrate that the two regulator/promoter combinations act independently from one another, and that multiple genes can efficiently and independently regulated by the selective addition of the desired hormone.

Figure 2:
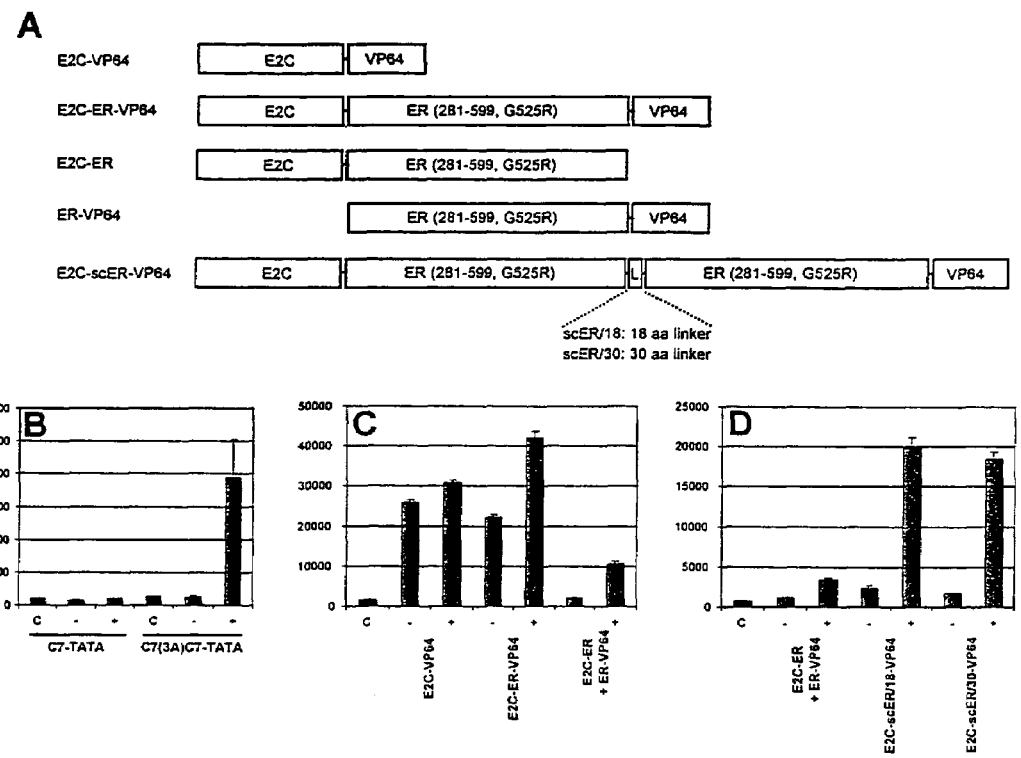
FIG. 2 shows regulation of gene expression by hormone-dependent, single-chain ER fusion constructs. A, structure of ER fusion proteins. E2C, six finger protein; L, flexible peptide linker. B, fusion proteins with a single ER-LBD bind as dimers. HeLa cells were cotransfected with a C7-ER-VP64 expression vector, and the indicated TATA luciferase reporter plasmids carrying either one or two C7 binding sites. 24 h after transfection, cells were either left untreated (−), or 100 nM 4-OHT was added (+). Luciferase activity in total cell extracts was measured 48 h after transfection. Each bar represents the mean value (+/−SD) of duplicate measurements. C, control plasmid pcDNA3 that does not express a fusion protein. C, D, regulation of transcription through a single binding site by fusion proteins with two ER-LBDs. HeLa cells were cotransfected with the indicated expression vectors and the E2C-TATA-luciferase reporter plasmid, carrying a single E2C binding site upstream of a TATA box. 4-OHT induction and measurement of luciferase activity was carried out as described in B.

Development of a monomeric hormone-dependent gene-switch. The ability to engineer DNA binding proteins with desired specificities makes it possible to generate artificial transcription factors capable of imposing dominant regulatory effects on endogenous genes [Beerli, R. R., Dreier, B., and Barbas, C. F., III (2000) *Proc. Natl. Acad. Sci. USA* 97, 1495-1500]. For many applications of this technology it may be desirable that the effect on endogenous gene expression is reversible. The use of steroid hormone receptor LBDs has the potential to render regulation of endogenous gene expression reversible. However, one major drawback is the fact that steroid hormone receptors, as well as the chimeric regulators described herein, bind DNA as dimers. Thus, when the fusion protein C7-ER-VP64 was transiently expressed in HeLa cells it was unable to regulate a reporter construct carrying a single C7 binding site, while it readily regulated a reporter that had two C7 binding sites and therefore accommodated binding of a dimer (FIG. 2B). An additional problem was encountered when the C7 DBD was replaced by E2C, which contains six zinc finger domains and recognizes the 18-bp sequence 5'-GGG GCC GGA GCC GCA GTG-3' (SEQ ID NO; 29) in the 5'-UTR of the proto-oncogene c-erbB-2 [Yamamoto, T., Ikawa, S., Akiyama, T., Semba, K., Nomura, N., Miyajima, N., Saito, T., and Toyoshima, K. (1986) *Nature* 319, 230-234; Beerli, R. R., Segal, D. J., Dreier, B., and Barbas, C. F., III (1998) *Proc. Natl. Acad. Sci. USA* 95, 14628-14633]. The E2C-ER-VP64 fusion protein was constitutively active on a reporter carrying a single E2C binding site, almost as active as an E2C-VP64 fusion without an ER LBD, and did not respond well to hormone. Apparently, the use of a large DNA binding domain recognizing an extended stretch of DNA with high affinity renders the chimera hormone- and dimerization-independent.

To overcome these problems, we produced two types of ER-based chimeric regulators, designed to be capable of regulating gene expression through a single binding site in a hormone-dependent manner. In the first strategy, a heterodimeric regulator was generated consisting of the engineered zinc finger protein E2C fused to an ER LBD, as well as an ER LBD fused to a VP64 activation domain (FIG. 2A). When this heterodimeric regulator was expressed in HeLa cells, it had no significant activity on the E2C-TATA-luc reporter plasmid in the absence of 4-OHT. Addition of hormone led to a 3- to 5-fold stimulation of luciferase expression, indicating the formation of functional heterodimers. However, hormone-induced reporter gene activation was significantly lower than that induced by an E2C-VP64 fusion protein, presumably at least in part due to the formation of E2C-ER and ER-VP64 homodimers. Homodimers were inactive, since neither E2C-ER nor ER-VP64 alone induced luciferase expression. In the second strategy, fusion proteins were generated by combining the dimerization partners E2C-ER and ER-VP64 in one single polypeptide, through a flexible polypeptide linker. Two linkers were tested, 18 and 30 amino acids in length, creating the proteins E2C-scER/18-VP64 and E2C-scER/30-VP64 (FIG. 2A). These proteins were expected to be activated via intramolecular, rather than intermolecular, dimerization and therefore functional as monomers. Combination of two ER LBDs into one single-chain fusion construct should allow a more efficient hormone-induced dimerization and therefore yield more efficient activators. Indeed, when E2C-scER/18-VP64 and E2C-scER/30-VP64 were transiently expressed in HeLa cells, they efficiently activated the E2C-TATA-luc reporter in a largely hormone-dependent manner (FIG. 2B, 2C and 2D). Thus, dimeric regulators requiring response elements similar to those of natural steroid hormone receptors were successfully converted into monomeric, ligand-dependent transcription factors.

Monomeric gene-switch based on EcR and RXR LBDs. To show that the production of a ligand-dependent monomeric gene switch by fusion with two LBDs is a generally applicable strategy, the utility of other nuclear hormone receptors was tested. In particular, utility of the LBDs of the *Drosophila* ecdysone receptor (EcR) was investigated. In *Drosophila*, this receptor functions as a heterodimer between EcR and the product of the ultraspiracle (USP) gene [Yao, T.-P., Forman, B. M., Jiang, Z., Cherbas, L., Chen, J.-D., McKeown, M., Cherbas, P., and Evans, R. M. (1993) *Nature* 366, 476-479]. However, it has been shown that EcR also efficiently heterodimerizes with USP's vertebrate homologue retinoid X receptor (RXR) in response to the ecdysone agonists Muristerone A or Ponasterone A (PonA) [Nakanishi, K. (1992)

*Steroids* 57, 649-657; Yao, T.-P., Forman, B. M., Jiang, Z., Cherbas, L., Chen, J.-D., McKeown, M., Cherbas, P., and Evans, R. M. (1993) *Nature* 366, 476-479; No, D., Yao, T.-P., and Evans, R. M. (1996) *Proc. Natl. Acad. Sci. USA* 93, 3346-3351]. The EcR and RXR LBDs were therefore used to prepare a monomeric gene switch analogous to the scER chimeras described above (FIG. 3A). Thus, the human RXRα LBD (aa373-654) and the *Drosophila* EcR LBD (aa202-462) were inserted in between the E2C DBD and the VP64 activation domain, creating E2C-RE-VP64. In this fusion construct, the two LBDs are connected by an 18 amino acid flexible linker, the same that was used in E2C-scER/18-VP64. When this chimeric regulator was transiently expressed in HeLa cells along with the E2C-TATA-luc reporter plasmid, significant basal activity was observed. However, activity could be increased 3-fold by PonA, showing that this artificial construct was hormone-responsive. To improve the ligand dependence, the length of the linker connecting the RXR and EcR LBDs was increased, a measure that seemed beneficial in the case of the single-chain ER constructs. A longer linker should allow the LBDs to optimize their contact and add to the conformational disorder in the unliganded state. Indeed, when the linker was elongated to 30 aa (in E2C-RLE-VP64) or 36 aa (in E2C-RLLE-VP64), basal activity was significantly reduced and PonA led to a 9- to 10-fold activation, an extent of responsiveness comparable to the one of the single-chain ER fusion constructs (FIG. 3B). Thus, serial connection of pairs of nuclear hormone receptor LBDs appears to be a generally applicable strategy to render monomeric DNA binding proteins ligand-dependent.

The hPR and mER LBDs used for the fusion proteins did not encompass their natural SV40-like nuclear localization signals (NLS), located between amino acids 637 and 644 in hPR, and between amino acids 260 and 267 in mER [Carson-Jurica, M. A., Schrader, W. T., and O'Malley, W. (1990) *Endocrine Reviews* 11, 201-220]. While it has been shown that this NLS is not required for hormone-dependent nuclear localization of hPR, regulation of the subcellular localization of steroid receptors appears to be complex, and it was not a priori clear whether the presence of the SV40-like NLS was required for proper function of the chimeric proteins. Thus, additional constructs were prepared that incorporated an SV40 NLS (PKKKRKV) (SEQ ID NO: 30) in single letter amirio acid code), either between VP16 and C7, or between C7 and LBD.

The chimeric transcriptional regulators were then tested for their ability to regulate the 10×C7-TATA-luc reporter plasmid in a hormone dependent manner. 10×C7-TATA-luc contains ten C7 binding sites [5'-GCG TGG GCG-3'] spaced by 5 nucleotides, and a TATA box, upstream of the firefly luciferase coding region. Each of the fusion proteins upregulated expression of luciferase in a largely hormone dependent manner. RU486 stimulated the activity of VP16-C7-PR 26-fold, while 4-OHT led to a 43-fold activation of VP16-C7-ER. There was no detectable crossreactivity between RU486 and ER, or between 4-OHT and PR. The presence of a NLS in either position was not only not required, but even undesirable, since it led to an increased basal (i.e. hormone-independent) activity of the fusion constructs, presumably through increased nuclear localization. Thus, the hPR (aa645-914) and mER (aa281-599, G525R) LBDs are able to confer hormone-dependence onto the zinc finger protein C7.

The ability to reversibly control the expression of multiple genes, or alleles of a gene, could prove very useful for many basic research applications. In particular, selective and independent expression of one gene, but not another (and vice versa), by small and nontoxic ligands would allow for a comparative analysis of gene function, both in vitro and in vivo. We have shown that our modular system for controlling target gene expression is indeed able to independently control the expression of two genes within the same transfected cell, as evidenced by RU486-dependent luciferase induction and 4-OHT-induced β-gal expression. The lack of β-gal induction by RU486, and luciferase induction by 4-OHT convincingly demonstrates the specificity of the chimeric regulators described here. Not only is the exquisite specificity of the utilized DNA binding domains retained, but also there is no detectable crossreaction between RU486 and the ER LBD, or between 4-OHT and the PR LBD.

What is claimed is:

1. An isolated chimeric polypeptide comprising a first functional domain of a protein which binds a selected DNA sequence, wherein the first functional domain is operatively linked to the N-terminus of two ligand binding domains from nuclear hormone receptors, wherein the DNA binding domain comprises at least one zinc finger DNA binding motif, wherein the chimeric polypeptide binds the ligands bound by the ligand binding domains of the nuclear hormone receptors and binds the selected DNA sequence bound by the first functional domain of the protein.

2. The polypeptide of claim 1 wherein the two ligand binding domains are covalently linked by means of a peptide linker.

3. The polypeptide of claim 2 wherein the linker contains from 10 to about 40 amino acid residues.

4. The polypeptide of claim 2 wherein the linker contains from 15 to about 35 amino acid residues.

5. The polypeptide of claim 2 wherein the linker contains from 18 to about 30 amino acid residues.

6. The polypeptide of claim 1 wherein the first and second ligand binding domains are from different nuclear hormone receptors.

7. The polypeptide of claim 1 wherein the first and second ligand binding domains are from the same nuclear hormone receptor.

8. The polypeptide of claim 7 wherein the nuclear hormone receptor is an estrogen receptor, a progesterone receptor, an ecdysone receptor, a retinoic acid receptor, or a retinoid X receptor.

9. The polypeptide of claim 1 wherein at least one of the ligand binding domains is from a retinoid X receptor.

10. The polypeptide of claim 1 that comprises from two to twelve zinc finger binding motifs.

11. The polypeptide of claim 1 that comprises from two to six zinc finger binding motifs.

12. The polypeptide of claim 1 wherein the zinc finger DNA binding motifs specifically bind to a nucleotide sequence of the formula $(GNN)_{1-6}$, where G is guanine and N is any nucleotide.

13. The polypeptide of claim 1 further comprising a second functional domain operatively linked to either one of the ligand binding domains or the first functional domain.

14. The polypeptide of claim 13 wherein the second functional domain is a transcriptional regulating domain.

15. The polypeptide of claim 14 wherein the DNA binding domain comprises at least one zinc finger DNA binding motif.

16. The polypeptide of claim 15 that comprises from two to twelve zinc finger DNA binding motifs.

17. The polypeptide of claim 15 that comprises from two to six zinc finger DNA binding motifs.

18. The polypeptide of claim 15 wherein the at least one zinc finger DNA binding motif specifically binds to a nucleotide sequence of the formula $(GNN)_{1-6}$, where G is guanine and N is any nucleotide.

19. The polypeptide of claim 14 wherein the transcriptional regulating domain is an activation domain.

20. The polypeptide of claim 14 wherein the transcriptional regulating domain is a repression domain.

21. An isolated chimeric polypeptide comprising: (a) a DNA binding domain having from two to six zinc finger DNA binding motifs which domain binds a selected DNA sequence; (b) a first ligand binding domain from a retinoid X receptor operatively linked to the DNA binding domain, and a second ligand binding domain from an ecdysone receptor operatively linked to the first ligand binding domain with a peptide spacer of from 18 to 36 amino acid residues; and (c) a transcriptional regulating domain operatively linked to the second ligand binding domain, wherein the chimeric polypeptide binds the selected DNA sequence, binds a ligand bound by the retinoid X receptor, binds a ligand bound by the ecdysone receptor, and transcriptionally regulates DNA that is operatively linked to the selected DNA sequence as a result of the presence of the transcriptional regulating domain in the chimeric polypeptide.

22. An isolated chimeric polypeptide comprising: (a) a DNA binding domain having from three to six zinc finger DNA binding motifs which domain binds a selected DNA sequence; (b) a first ligand binding domain from a progesterone receptor operatively linked to the DNA binding domain, and a second ligand binding domain from a progesterone receptor linked to the first ligand binding domain with a peptide spacer of from 18 to 36 amino acid residues; and (c) a transcriptional regulating domain operatively linked to the second ligand binding domain, wherein the chimeric polypeptide binds the selected DNA sequence, binds a ligand bound by progesterone receptor, and transcriptionally regulates DNA that is operatively linked to the selected DNA sequence as a result of the presence of the transcriptional regulating domain in the chimeric polypeptide.

23. A polynucleotide that encodes the polypeptide of claim 1.

24. A polynucleotide that encodes the polypeptide of claim 14.

25. An expression vector comprising the polynucleotide of claim 23.

26. An expression vector comprising the polynucleotide of claim 24.

27. A cell containing the polynucleotide of claim 23.

28. A cell containing the polynucleotide of claim 24.

29. A host cell transformed with the expression vector of claim 25.

30. A host cell transformed with the expression vector of claim 26.

31. An isolated chimeric polypeptide comprising a first functional domain of a protein which binds a selected DNA sequence, wherein the first functional domain is operatively linked to the N-terminus of two ligand binding domains for the same ligand, wherein at least one of the ligand binding domains is from a nuclear hormone receptor, wherein the chimeric polypeptide binds the ligands bound by the ligand binding domains and binds the selected DNA sequence bound by the first functional domain of the protein.

32. The polypeptide of claim 31 wherein the two ligand binding domains are covalently linked by means of a peptide linker.

33. The polypeptide of claim 32 wherein the linker contains from about 10 to about 40 amino acid residues.

34. The polypeptide of claim 32 wherein the linker contains from about 15 to about 35 amino acid residues.

35. The polypeptide of claim 32 wherein the linker contains from about 18 to about 30 amino acid residues.

36. The polypeptide of claim 31 wherein the DNA binding domain comprises at least one zinc finger DNA binding motif.

37. The polypeptide of claim 36 that comprises from two to twelve DNA binding motifs.

38. The polypeptide of claim 36 that comprises from two to six DNA binding motifs.

39. The polypeptide of claim 36 wherein the at least one zinc finger DNA binding motif specifically binds to a nucleotide sequence of the formula $(GNN)_{1-6}$, where G is guanine and N is any nucleotide.

40. The polypeptide of claim 31 further comprising a transcriptional regulating domain.

41. The polypeptide of claim 31 further comprising a second functional domain operatively linked to either one of the ligand binding domains or the first functional domain.

42. The polypeptide of claim 41 wherein the second functional domain is a transcriptional regulating domain.

43. The polypeptide of claim 42 wherein the DNA binding domain comprises at least one zinc finger DNA binding motif.

44. The polypeptide of claim 42 that comprises from two to twelve zinc finger DNA binding motifs.

45. The polypeptide of claim 42 that comprises from two to six zinc finger DNA binding motifs.

46. The polypeptide of claim 43 wherein the at least one zinc finger DNA binding motif specifically binds to a nucleotide sequence of the formula $(GNN)_{1-6}$, where G is guanine and N is any nucleotide.

47. The polypeptide of claim 42 wherein the transcription regulating domain is an activation domain.

48. The polypeptide of claim 27 wherein the transcription regulating domain is a repression domain.

49. The polypeptide of claim 42 wherein the DNA binding domain is a zinc finger nucleotide binding domain and wherein the zinc finger nucleotide binding domain is selected from the group consisting of:
(a) a zinc finger nucleotide binding domain from E2C, C7, B3B (SEQ ID NO:32), 2C7 (SEQ ID NO:34), B3C2 (SEQ ID NO:36), and N1;
(b) a zinc finger nucleotide binding domain derived from a zinc finger nucleotide binding domain selected from the group consisting of E2C, C7, B3B, 2C7, B3C2, and N1 by truncation;
(c) a zinc finger nucleotide binding domain derived from a zinc finger nucleotide binding domain selected from the group consisting of E2C, C7, B3B, 2C7, B3C2, and N1 by expansion; and
(d) a zinc finger nucleotide binding domain derived from a zinc finger nucleotide binding domain selected from the group consisting of E2C, C7, B3B, 2C7, B3C2, and N1 by mutagenesis.

50. The polypeptide of claim 47 wherein the activation domain is from VP16, TA2, VP64 (a tetrameric repeat of the minimal activation domain of VP16), signal transducer and activator of transcription 6 (STAT6), reticuloendotheliosis virus A oncogene (relA), TATA binding protein associated factor-1 (TAF-1), TATA binding protein associated factor-2 (TAF-2), glucocorticoid receptor TAU-1, or glucocorticoid receptor TAU-2.

51. The polypeptide of claim 48 wherein the repression domain is from ETS repressor factor, the ETS repressor factor repressor domain (ERD), Kruppel-associated box (KRAB), human MAD1 protein, mSin3 interaction domain of the human MAD1 protein (SID), histone deacetylase, DNA methylase, or is a derivative or multimer of KRAB, SID, or ERD selected from the group consisting of KRAB-ERD, SID-ERD, (KRAB)$_2$, (KRAB)$_3$, KRAB-A, (KRAB-A)$_2$, (SID)$_2$, (KRAB-A)-SID, and SID-KRAB-A.

52. The polypeptide of claim 31 wherein at least one of the ligand binding domains binds a ligand selected from the group consisting of: 11β-(4-dimethylaminophenyl)-17β-hydroxy-17α-propinyl-4,9-estradiene-3-one; 11β-(4-dimethylaminophenyl)-17α-hydroxy-17β-(3-hydroxypropyl)-13α-methyl-4,9-gonadiene-3-one; 11β-(4-acetylphenyl)-17β-hydroxy-17α-(1-propinyl)-4,9-estradiene-3-one; 11β-(4-dimethylaminophenyl)-17β-hydroxy-17α-(3-hydroxy-1(Z)-propenyl-estra-4,9-diene-3-one ; (7β, 11β, 17β) 11-(4-dimethylaminophenyl)-7-methyl-4',5 '-dihydrospiro {ester-4,9-diene-17,2'(3'H)-furan}-3-one; (11β, 14β, 17α)-4',5'-dihydro-11-(4-dimethylaminophenyl) {spiroestra-4,9-diene-17,2'(3'H)-furan}-3-one; and 5-alpha-pregnane-3,2-dione.

53. The polypeptide of claim 1 wherein at least one of the nuclear hormone receptors is selected from the group consisting of estrogen receptor (ER), progesterone receptor (PR), glucocorticoid-α receptor, glucocorticoid-β receptor, mineralocorticoid receptor, androgen receptor, thyroid hormone receptor, retinoic acid receptor (RAR), retinoid X receptor (RXR), Vitamin D receptor, COUP-TF receptor, ecdysone receptor (EcR), Nurr-1receptor, and orphan receptors.

54. The polypeptide of claim 31 wherein the polypeptide is a gene switch using RXR, E2C, and activation domains wherein the gene switch is selected from the group consisting of E2C-RXR-L-DE-VP64, E2C-RXR-LL-DE-VP64, E2C-RXR-LLL-DE-VP64, E2C-RXR-L-BE-VP64, E2C-RXR-LL-BE-VP64, E2C-RXR-LLL-BE-VP64, E2C-RXR-L-DE-VP16, E2C-RXR-LL-DE-VP16, E2C-RXR-LLL-DE-VP16, E2C-RXR-L-BE-VP16, E2C-RXR-LL-BE-VP16, and E2C-RXR-LLL-BE-VP16, wherein DE is the *Drosophila melanogaster* ecdysone receptor, BE is the *Bombyx* ecdysone receptor, and wherein L is a linker of 18 amino acids, LL is a linker of 30 amino acids or LLL is a linker of 36 amino acids.

55. The polypeptide of claim 31 wherein the polypeptide is a gene switch using RXR, 2C7, and activation domains wherein the gene switch is selected from the group consisting of 2C7-RXR-L-DE-VP64, 2C7-RXR-LL-DE-VP64, 2C7-RXR-LLL-DE-VP64, 2C7-RXR-L-BE-VP64, 2C7-RXR-LL-BE-VP64, 2C7-RXR-LLL-BE-VP64, 2C7-RXR-L-DE-VP16, 2C7-RXR-LL-DE-VP16, 2C7-RXR-LLL-DE-VP16, 2C7-RXR-L-BE-VP16, 2C7-RXR-LL-BE-VP16, and E2C-RXR-LLL-BE-VP16.

56. The polypeptide of claim 31 wherein the polypeptide is a gene switch using RXR, B3B, and activation domains wherein the gene switch is selected from the group consisting of B3B-RXR-L-DE-VP64, B3B-RXR-LL-DE-VP64, B3B-RXR-LLL-DE-VP64, B3B 7-RXR-L-BE-VP64, B3B 7-RXR-LL-BE-VP64, B3B-RXR-LLL-BE-VP64, B3B-RXR-L-DE-VP16, B3B-RXR-LL-DE-VP16, B3B-RXR-LLL-DE-VP16, B3B-RXR-L-BE-VP16, B3B-RXR-LL-BE-VP16, and B3B-RXR-LLL-BE-VP16.

57. The polypeptide of claim 31 wherein the polypeptide is a gene switch using RXR, B3C2, and activation domains wherein the gene switch is selected from the group consisting of B3C2-RXR-L-DE-VP64, B3C2-RXR-LL-DE-VP64, B3C2-RXR-LLL-DE-VP64, B3C2-RXR-L-BE-VP64, B3C2-RXR-LL-BE-VP64, B3C2-RXR-LLL-BE-VP64, B3C2-RXR-L-DE-VP16, B3C2-RXR-LL-DE-VP16, B3C2-RXR-LLL-DE-VP16, B3C2-RXR-L-BE-VP16, B3C2 B-RXR-LL-BE-VP16, and B3C2-RXR-LLL-BE-VP16.

58. The polypeptide of claim 31 wherein the polypeptide is a gene switch using RXR, E2C, and repression domains wherein the gene switch is selected from the group consisting of E2C-RXR-L-DE-(KRAB-A)$_2$, E2C-RXR-LL-DE-(KRAB-A)$_2$, E2C-RXR-LLL-DE-(KRAB-A)$_2$, E2C-RXR-L-BE-(KRAB-A)$_2$, E2C-RXR-LL-BE-(KRAB-A)$_2$, E2C-RXR-LLL-BE-(KRAB-A)$_2$, E2C-RXR-L-DE-(KRAB-A)$_2$, E2C-RXR-LL-DE-(KRAB-A)$_2$, E2C-RXR-LLL-DE-(KRAB-A)$_2$, E2C-RXR-L-BE-(KRAB-A)$_2$, E2C-RXR-LL-BE-(KRAB-A)$_2$, E2C-RXR-LLL-BE-(KRAB-A)$_2$, E2C-RXR-L-DE-(SID)$_2$, E2C-RXR-LL-DE-(SID)$_2$, E2C-RXR-LLL-DE-(SID)$_2$, E2C-RXR-L-BE-(SID)$_2$, E2C-RXR-LL-BE-(SID)$_2$, E2C-RXR-LLL-BE-(SID)$_2$, E2C-RXR-L-DE-(SID)$_2$, E2C-RXR-LL-DE-(SID)$_2$, E2C-RXR-LLL-DE-(SID)$_2$, E2C-RXR-L-BE-(SID)$_2$, E2C-RXR-LL-BE-(SID)$_2$, and E2C-RXR-LLL-BE-(SID)$_2$.

59. The polypeptide of claim 31 wherein the polypeptide is a gene switch using RXR, 2C7, and repression domains wherein the gene switch is selected from the group consisting of 2C7-RXR-L-DE-(KRAB-A)$_2$, 2C7-RXR-LL-DE-(KRAB-A)$_2$, 2C7-RXR-LLL-DE-(KRAB-A)$_2$, 2C7-RXR-L-BE-(KRAB-A)$_2$, 2C7-RXR-LL-BE-(KRAB-A)$_2$, 2C7-RXR-LLL-BE-(KRAB-A)$_2$, 2C7-RXR-L-DE-(KRAB-A)$_2$, 2C7-RXR-LL-DE-(KRAB-A)$_2$, 2C7-RXR-LLL-DE-(KRAB-A)$_2$, 2C7-RXR-L-BE-(KRAB-A)$_2$, 2C7-RXR-LL-BE-(KRAB-A)$_2$, E2C-RXR-LLL-BE-(KRAB-A)$_2$, 2C7-RXR-L-DE-(SID)$_2$, 2C7-RXR-LL-DE-(SID)$_2$, 2C7-RXR-LLL-DE-(SID)$_2$, 2C7-RXR-L-BE-(SID)$_2$, 2C7-RXR-LL-BE-(SID)$_2$, 2C7-RXR-LLL-BE-(SID)$_2$, 2C7-RXR-L-DE-(SID)$_2$, 2C7-RXR-LL-DE-(SID)$_2$, 2C7-RXR-LLL-DE-(SID)$_2$, 2C7-RXR-L-BE-(SID)$_2$, 2C7-RXR-LL-BE-(SID)$_2$, and E2C-RXR-LLL-BE-(SID)$_2$.

60. The polypeptide of claim 31 wherein the polypeptide is a gene switch using RXR, B3B, and repression domains wherein the gene switch is selected from the group consisting of B3B-RXR-L-DE-(KRAB-A)₂, B3B-RXR-LL-DE-(KRAB-A)₂, B3B-RXR-LLL-DE-(KRAB-A)₂, B3B 7-RXR-L-BE-(KRAB-A)₂, B3B 7-RXR-LL-BE-(KRAB-A)₂, B3B-RXR-LLL-BE-(KRAB-A)₂, B3B-RXR-L-DE-(KRAB-A)₂, B3B-RXR-LL-DE-(KRAB-A)₂, B3B-RXR-LLL-DE-(KRAB-A)₂, B3B-RXR-L-BE-(KRAB-A)₂, B3B-RXR-LL-BE-(KRAB-A)₂, B3B-RXR-LLL-BE-(KRAB-A)₂, B3B-RXR-L-DE-(SID)₂, B3B-RXR-LL-DE-(SID)2, B3B-RXR-LLL-DE-(SID)₂, B3B 7-RXR-L-BE-(SID)₂, B3B 7-RXR-LL-BE-(SID)₂, B3B-RXR-LLL-BE-(SID)2, B3B-RXR-L-DE-(SID)₂, B3B-RXR-LL-DE-(SID)2, B3B-RXR-LLL-DE-(SID)₂, B3B-RXR-L-BE-(SID)₂, B3B-RXR-LL-BE-(SID)₂, B3B-RXR-LLL-BE-(SID)₂.

61. The polypeptide of claim 31 wherein the polypeptide is a gene switch using RXR, B3C2, and repression domains wherein the gene switch is selected from the group consisting of B3C2-RXR-L-DE-(KRAB-A)₂, B3C2-RXR-LL-D-(KRAB-A)₂, B3C2-RXR-LLL-DE-(KRAB-A)2, B3C2-RXR-L-BE-(KRAB-A)₂, B3C2-RXR-LL-BE-(KRAB-A)₂, B3C2-RXR-LLL-BE-(KRAB-A)₂, B3C2-RXR-L-DE-(KRAB-A)₂, B3C2-RXR-LL-DE-(KRAB-A)₂, B3C2-RXR-LLL-DE-(KRAB-A)₂, B3C2-RXR-L-BE-(KRAB-A)₂, B3C2B-RXR-LL-BE-(KRAB-A)₂, B3C2-RXR-LLL-BE-(KRAB-A)₂, B3C2-RXR-L-DE-(SID)₂, B3C2-RXR-LL-DE-(SID)₂, B3C2-RXR-LLL-DE-(SID)₂, B3 C2-RXR-L-BE-(SID)₂, B3C2-RXR-LL-BE-(SID)₂, B3C2-RXR-LLL-BE-(SID)₂, B3C2-RXR-L-DE-(SID)₂, B3C2-RXR-LL-DE-(SID)₂, B3C2-RXR-LLL-DE-(SID)₂, B3C2-RXR-L-BE-(SID)₂, B3C2-RXR-LL-BE-(SID)₂, and B3C2-RXR-LLL-BE-(SID)₂.

62. The polypeptide of claim 31 wherein the polypeptide is a gene switch using PR, E2C, and activation domains wherein the gene switch is selected from the group consisting of E2C-PR-L-PR-VP64, E2C-PR-LL-PR-VP64, E2C-PR-LLL-PR-VP64, E2C-PR-L-PR-VP64, E2C-PR-LL-PR-VP64, E2C-PR-LLL-PR-VP64, E2C-PR-L-PR-VP16, E2C-PR-LL-PR-VP16, E2C-PR-LLL-PR-VP16, E2C-PR-L-PR-VP16, E2C-PR-LL-PR-VP16, and E2C-PR-LLL-PR-VP16.

63. The polypeptide of claim 31 wherein the polypeptide is a gene switch using PR, 2C7, and activation domains wherein the gene switch is selected from the group consisting of 2C7-PR-L-PR-VP64, 2C7-PR-LL-PR-VP64, 2C7-PR-LLL-PR-VP64, 2C7-PR-L-PR-VP64, 2C7-PR-LL-PR-VP64, 2C7-PR-LLL-PR-VP64, 2C7-PR-L-PR-VP16, 2C7-PR-LL-PR-VP 16, 2C7-PR-LLL-PR-VP16, 2C7-PR-L-PR-VP16, 2C7-PR-LL-PR-VP16, and E2C-PR-LLL-PR-VP16.

64. The polypeptide of claim 31 wherein the polypeptide is a gene switch using PR, B3B, and activation domains wherein the gene switch is selected from the group consisting of B3B-PR-L-PR-VP64, B3B-PR-LL-PR-VP64, B3B-PR-LLL-PR-VP64, B3B7-PR-L-PR-VP64, B3B 7-PR-LL-PR-VP64, B3B-PR-LLL-PR-VP64, B3B-PR-L-PR-VP16, B3B-PR-LL-PR-VP16, B3B-PR-LLL-PR-VP16, B3B-PR-L-PR-VP16, B3B-PR-LL-PR-VP16, and B3B-PR-LLL-PR-VP16.

65. The polypeptide of claim 31 wherein the polypeptide is a gene switch using PR, B3C2, and activation domains wherein the gene switch is selected from the group consisting of B3C2-PR-L-PR-VP64, B3C2-PR-LL-PR-VP64, B3C2-PR-LLL-PR-VP64, B3C2-PR-L-PR-VP64, B3C2-PR-LL-PR-VP64, B3C2-PR-LLL-PR-VP64, B3C2-PR-L-PR-VP16, B3C2-PR-LL-PR-VP16, B3C2-PR-LLL-PR-VP16, B3C2-PR-L-PR-VP16, B3C2-B-PR-LL-PR-VP16, and B3C2-PR-LLL-PR-VP16.

66. The polypeptide of claim 31 wherein the polypeptide is a gene switch using PR, E2C, and repression domains wherein the gene switch is selected from the group consisting of E2C-PR-L-PR-(KRAB-A)₂, E2C-PR-LL-PR-(KRAB-A)₂, E2C-PR-LLL-PR-(KRAB-A)₂, E2C-PR-L-PR-(KRAB-A)₂, E2C-PR-LL-PR-(KRAB-A)₂, E2C-PR-LLL-PR-(KRAB-A)₂, E2C-PR-L-PR-(KRAB-A)₂, E2C-PR-LL-PR-(KRAB-A)₂, E2C-PR-LLL-PR-(KRAB-A)₂, E2C-PR-L-PR-(KRAB-A)₂, E2C-PR-LL-PR-(KRAB-A)₂, E2C-PR-LLL-PR-(KRAB-A)₂, E2C-PR-L-PR-(SID)₂, E2C-PR-LL-PR-(SID)₂, E2C-PR-LLL-PR-(SID)₂, E2C-PR-L-PR-(SID)₂, E2C-PR-LL-PR-(SID)₂, E2C-PR-LLL-PR-(SID)₂, E2C-PR-L-PR-(SID)₂, E2C-PR-LL-PR-(SID)₂, E2C-PR-LLL-PR-(SID)₂, E2C-PR-L-PR-(SID)₂, E2C-PR-LL-PR-(SID)₂, and E2C-PR-LLL-PR-(SID)₂.

67. The polypeptide of claim 31 wherein the polypeptide is a gene switch using PR, 2C7, and repression domains wherein the gene switch is selected from the group consisting of 2C7-PR-L-PR-(KRAB-A)₂, 2C7-PR-LL-PR-(KRAB-A)₂, 2C7-PR-LLL-PR-(KRAB-A)₂, 2C7-PR-L-PR-(KRAB-A)₂, 2C7-PR-LL-PR-(KRAB-A)₂, 2C7-PR-LLL-PR-(KRAB-A)₂, 2C7-PR-L-PR-(KRAB-A)₂, 2C7-PR-LL-PR-(KRAB-A)₂, 2C7-PR-LLL-PR-(KRAB-A)₂, 2C7-PR-L-PR-(KRAB-A)₂, 2C7-PR-LL-PR-(KRAB-A)₂, E2C-PR-LLL-PR-(KRAB-A)₂, 2C7-PR-L-PR-(SID)₂, 2C7-PR-LL-PR-(SID)₂, 2C7-PR-LLL-PR-(SID)₂, 2C7-PR-L-PR-(SID)₂, 2C7-PR-LL-PR-(SID)₂, 2C7-PR-LLL-PR-(SID)₂, 2C7-PR-L-PR-(SID)₂, 2C7-PR-LL-PR-(SID)₂, 2C7-PR-LLL-PR-(SID)₂, 2C7-PR-L-PR-(SID)₂, 2C7-PR-LL-PR-(SID)₂, and E2C-PR-LLL-PR-(SID)₂.

68. The polypeptide of claim 31 wherein the polypeptide is a gene switch using PR, B3B, and repression domains wherein the gene switch is selected from the group consisting of B3B-PR-L-PR-(KRAB-A)₂, B3B-PR-LL-PR-(KRAB-A)₂, B3B-PR-LLL-PR-(KRAB-A)₂, B3B 7-PR-L-PR-(KRAB-A)₂, B3B 7-PR-LL-PR-(KRAB-A)₂, B3B-PR-LLL-PR-(KRAB-A)₂, B3B-PR-L-PR-(KRAB-A)₂, B3B-PR-LL-PR-(KRAB-A)₂, B3B-PR-LLL-PR-(KRAB-A)₂, B3B-PR-L-PR-(KRAB-A)₂, B3B-PR-LL-PR-(KRAB-A)₂, B3B-PR-LLL-PR-(KRAB-A)₂, B3B-PR-L-PR-(SID)₂, B3B-PR-LL-PR-(SID)₂, B3B-PR-LLL-PR-(SID)₂, B3B 7-PR-L-PR-(SID)₂, B3B7-PR-LL-PR-(SID)₂, B3B-PR-LLL-PR-(SID)₂, B3B-PR-L-PR-(SID)₂, B3B-PR-LL-PR-(SID)₂, B3B-PR-LLL-PR-(SID)₂, B3B-PR-L-PR-(SID)₂, B3B-PR-LL-PR-(SID)₂, and B3B-PR-LLL-PR-(SID)₂.

69. The polypeptide of claim 31 wherein the polypeptide is a gene switch using PR, B3C2, and repression domains wherein the gene switch is selected from the group consisting of B3C2-PR-L-PR-(KRAB-A)₂, B3C2-PR-LL-PR-(KRAB-A)₂, B3C2-PR-LLL-PR-(KRAB-A)₂, B3C2-PR-L-PR-(KRAB-A)₂, B3C2-PR-LL-PR-(KRAB-A)₂, B3C2-PR-LLL-PR-(KRAB-A)₂, B3C2-PR-L-PR-(KRAB-A)₂, B3C2-PR-LL-PR-(KRAB-A)₂, B3C2-PR-LLL-PR-(KRAB-A)₂, B3C2-PR-L-PR-(KRAB-A)₂, B3C2 B-PR-LL-PR-(KRAB-A)₂, B3C2-PR-LLL-PR-(KRAB-A)₂, B3C2-PR-L-PR-(SID)₂, B3C2-PR-LL-PR-(SID)₂, B3C2-PR-LLL-PR-(SID)₂, B3C2-PR-L-PR-(SID)₂, B3C2-PR-LL-PR-(SID)₂, B3C2-PR-LLL-PR-(SID)₂, B3C2-PR-L-PR-(SID)₂, B3C2-PR-LL-PR-(SID)₂, B3C2-PR-LLL-PR-(SID)₂, B3C2-PR-L-PR-(SID)₂, B3C2 B-PR-LL-PR-(SID)₂, and B3C2-PR-LLL-PR-(SID)₂.

70. The polypeptide of claim 31 wherein the polypeptide is a gene switch using ER, E2C, and activation domains wherein the gene switch is selected from the group consisting of E2C-ER-L-ER-VP64, E2C-ER-LL-ER-VP64, E2C-ER-LLL-ER-VP64, E2C-ER-L-ER-VP64, E2C-ER-LL-ER-VP64, E2C-ER-LLL-ER-VP64, E2C-ER-L-ER-VP16, E2C-ER-LL-ER-VP16, E2C-ER-LLL-ER-VP16, E2C-ER-L-ER-VP16, E2C-ER-LL-ER-VP16, and E2C-ER-LLL-ER-VP16.

71. The polypeptide of claim 31 wherein the polypeptide is a gene switch using ER, 2C7, and activation domains wherein the gene switch is selected from the group consisting of 2C7-ER-L-ER-VP64, 2C7-ER-LL-ER-VP64, 2C7-ER-LLL-ER-VP64, 2C7-ER-L-ER-VP64, 2C7-ER-LL-ER-VP64, 2C7-ER-LLL-ER-VP64, 2C7-ER-L-ER-VP16, 2C7-ER-LL-ER-VP16, 2C7-ER-LLL-ER-VP16, 2C7-ER-L-ER-VP16, 2C7-ER-LL-ER-VP16, and E2C-ER-LLL-ER-VP16.

72. The polypeptide of claim 31 wherein the polypeptide is a gene switch using ER, B3B, and activation domains wherein the gene switch is selected from the group consisting of B3B-ER-L-ER-VP64, B3B-ER-LL-ER-VP64, B3B-ER-LL-ER-VP64, B3B 7-ER-L-ER-VP64, B3B 7-ER-LL-ER-VP64, B3B-ER-LLL-ER-VP64, B3B-ER-L-ER-VP16, B3B-ER-LL-ER-VP16, B3B-ER-LLL-ER-VP16, B3B-ER-L-ER-VP16, B3B-ER-LL-ER-VP16, and B3B-ER-LLL-ER-VP16.

73. The polypeptide of claim 31 wherein the polypeptide is a gene switch using ER, B3C2, and activation domains wherein the gene switch is selected from the group consisting of B3C2-ER-L-ER-VP64, B3C2-ER-LL-ER-VP64, B3C2-ER-LLL-ER-VP64, B3C2-ER-L-ER-VP64, B3C2-ER-LL-ER-VP64, B3C2-ER-LLL-ER-VP64, B3C2-ER-L-ER-VP16, B3C2-ER-LL-ER-VP16, B3C2-ER-LLL-ER-VP16, B3C2-ER-L-ER-VP16, B3C2 B-ER-LL-ER-VP16, and B3C2-ER-LLL-ER-VP16.

74. The polypeptide of claim 31 wherein the polypeptide is a gene switch using ER, E2C, and repression domains wherein the gene switch is selected from the group consisting of E2C-ER-L-ER-(KRAB-A)$_2$, E2C-ER-LL-ER-(KRAB-A)$_2$, E2C-ER-LLL-ER-(KRAB-A)$_2$, E2C-ER-L-ER-(KRAB-A)$_2$, E2C-ER-LL-ER-(KRAB-A)$_2$, E2C-ER-LLL-ER-(KRAB-A)$_2$, E2C-ER-L-ER-(KRAB-A)$_2$, E2C-ER-LL-ER-(KRAB-A)$_2$, E2C-ER-LLL-ER-(KRAB-A)$_2$, E2C-ER-L-ER-(KRAB-A)$_2$, E2C-ER-LL-ER-(KRAB-A)$_2$, E2C-ER-LLL-ER-(KRAB-A)$_2$, E2C-ER-L-ER-(SID)$_2$, E2C-ER-LL-ER-(SID)$_2$, E2C-ER-LLL-ER-(SID)$_2$, E2C-ER-L-ER-(SID)$_2$, E2C-ER-LL-ER-(SID)$_2$, E2C-ER-LLL-ER-(SID)$_2$, E2C-ER-L-ER-(SID)$_2$, E2C-ER-LL-ER-(SID)$_2$, E2C-ER-LLL-ER-(SID)$_2$, E2C-ER-L-ER-(SID)$_2$, E2C-ER-LL-ER-(SID)$_2$, and E2C-ER-LLL-ER-(SID)$_2$.

75. The polypeptide of claim 31 wherein the polypeptide is a gene switch using ER, 2C7, and repression domains wherein the gene switch is selected from the group consisting of 2C7-ER-L-ER-(KRAB-A)$_2$, 2C7-ER-LL-ER-(KRAB-A)$_2$, 2C7-ER-LLL-ER-(KRAB-A)$_2$, 2C7-ER-L-ER-(KRAB-A)$_2$, 2C7-ER-LL-ER-(KRAB-A)$_2$, 2C7-ER-LLL-ER-(KRAB-A)$_2$, 2C7-ER-L-ER-(KRAB-A)$_2$, 2C7-ER-LL-ER-(KRAB-A)$_2$, 2C7-ER-LLL-ER-(KRAB-A)$_2$, 2C7-ER-L-ER-(KRAB-A)$_2$, 2C7-ER-LL-ER-(KRAB-A)$_2$, E2C-ER-LLL-ER-(KRAB-A)$_2$, 2C7-ER-L-ER-(SID)$_2$, 2C7-ER-LL-ER-(SID)$_2$, 2C7-ER-LLL-ER-(SID)$_2$, 2C7-ER-L-ER-(SID)$_2$, 2C7-ER-LL-ER-(SID)$_2$, 2C7-ER-LLL-ER-(SID)$_2$, 2C7-ER-L-ER-(SID)$_2$, 2C7-ER-LL-ER-(SID)$_2$, 2C7-ER-LLL-ER-(SID)$_2$, 2C7-ER-L-ER-(SID)$_2$, 2C7-ER-LL-ER-(SID)$_2$, and E2C-ER-LLL-ER-(SID)$_2$.

76. The polypeptide of claim 31 wherein the polypeptide is a gene switch using ER, B3B, and repression domains wherein the gene switch is selected from the group consisting of B3B-ER-L-ER-(KRAB-A)$_2$, B3B-ER-LL-ER-(KRAB-A)$_2$, B3B-ER-LLL-ER-(KRAB-A)$_2$, B3B 7-ER-L-ER-(KRAB-A)$_2$, B3B 7-ER-LL-ER-(KRAB-A)$_2$, B3B-ER-LLL-ER-(KRAB-A)$_2$, B3B-ER-L-ER-(KRAB-A)$_2$, B3B-ER-LL-ER-(KRAB-A)$_2$, B3B-ER-L-ER-(KRAB-A)$_2$, B3B-ER-LL-ER-(KRAB-A)$_2$, B3B-ER-LLL-ER-(KRAB-A)$_2$, B3B-ER-L-ER-(SID)$_2$, B3B-ER-LL-ER-(SID)$_2$, B3B-ER-LLL-ER-(SID)$_2$, B3B 7-ER-L-ER-(SID)$_2$, B3B 7-ER-LL-ER-(SID)$_2$, B3B-ER-LLL-ER-(SID)$_2$, B3B-ER-L-ER-(SID)$_2$, B3B-ER-LL-ER-(SID)$_2$, B3B-ER-LLL-ER-(SID)$_2$, B3B-ER-L-ER-(SID)$_2$, B3B-ER-LL-ER-(SID)$_2$, and B3B-ER-LLL-ER-(SID)$_2$.

77. The polypeptide of claim 31 wherein the polypeptide is a gene switch using ER, B3C2, and repression domains wherein the gene switch is selected from the group consisting of B3C2-ER-L-ER-(KRAB-A)$_2$, B3C2-ER-LL-ER-(KRAB-A)$_2$, B3C2-ER-LLL-ER-(KRAB-A)$_2$, B3C2-ER-L-ER-(KRAB-A)$_2$, B3C2-ER-LL-ER-(KRAB-A)$_2$, B3C2-ER-LLL-ER-(KRAB-A)$_2$, B3C2-ER-L-ER-(KRAB-A)$_2$, B3C2-ER-LL-ER-(KRAB-A)$_2$, B3C2-ER-LLL-ER-(KRAB-A)$_2$, B3C2-ER-L-ER-(KRAB-A)$_2$, B3C2 B-ER-LL-ER-(KRAB-A)$_2$, B3C2-ER-LLL-ER-(KRAB-A)$_2$, B3C2-ER-L-ER-(SID)$_2$, B3C2-ER-LL-ER-(SID)$_2$, B3C2-ER-LLL-ER-(SID)$_2$, B3C2-ER-L-ER-(SID)$_2$, B3C2-ER-LL-ER-(SID)$_2$, B3C2-ER-LLL-ER-(SID)$_2$, B3C2-ER-L-ER-(SID)$_2$, B3C2-ER-LL-ER-(SID)$_2$, B3C2-ER-LLL-ER-(SID)$_2$, B3C2-ER-L-ER-(SID)$_2$, B3C2 B-ER-LL-ER-(SID)$_2$, and B3C2-ER-LLL-ER-(SID)$_2$.

78. The polypeptide of claim 31 wherein the polypeptide has activation or repression activity at multiple promoters.

79. The polypeptide of claim 1 wherein the first ligand binding domain is from an estrogen receptor.

80. The polypeptide of claim 1 wherein the second ligand binding domain is from an estrogen receptor.

81. The polypeptide of claim 79 wherein the second ligand binding domain is from an estrogen receptor.

82. The polypeptide of claim 31 wherein the first ligand binding domain is from an estrogen receptor.

83. The polypeptide of claim 31 wherein the second ligand binding domain is from an estrogen receptor.

84. The polypeptide of claim 82 wherein the second ligand binding domain is from an estrogen receptor.

85. The polypeptide of claim 79 wherein the two ligand binding domains are covalently linked by means of a peptide linker.

86. The polypeptide of claim 80 wherein the two ligand binding domains are covalently linked by means of a peptide linker.

87. The polypeptide of claim 82 wherein the two ligand binding domains are covalently linked by means of a peptide linker.

88. The polypeptide of claim 83 wherein the two ligand binding domains are covalently linked by means of a peptide linker.

89. The polypeptide of claim 85 wherein the linker contains from 10 to about 40 amino acid residues.

90. The polypeptide of claim 86 wherein the linker contains from 10 to about 40 amino acid residues.

91. The polypeptide of claim 87 wherein the linker contains from 10 to about 40 amino acid residues.

92. The polypeptide of claim 88 wherein the linker contains from 10 to about 40 amino acid residues.

93. The polypeptide of claim 79 wherein the DNA binding domain comprises at least one zinc finger binding motif.

94. The polypeptide of claim 80 wherein the DNA binding domain comprises at least one zinc finger binding motif.

95. The polypeptide of claim 82 wherein the DNA binding domain comprises at least one zinc finger binding motif.

96. The polypeptide of claim 83 wherein the DNA binding domain comprises at least one zinc finger binding motif.

97. The polypeptide of claim 93 further comprising a transcriptional regulating domain.

98. The polypeptide of claim 94 further comprising a transcriptional regulating domain.

99. The polypeptide of claim 95 further comprising a transcriptional regulating domain.

100. The polypeptide of claim 96 further comprising a transcriptional regulating domain.

101. The polypeptide of claim 13 wherein the second functional domain is a transcriptional regulating domain and is C-terminal to the ligand binding domains.

102. The polypeptide of claim 13 wherein the second functional domain is a transcriptional regulating domain and is N-terminal to the first functional domain.

* * * * *